(12) United States Patent  
Feinberg et al.

(10) Patent No.: US 7,955,315 B2  
(45) Date of Patent: Jun. 7, 2011

(54) ARTICULATING LAPAROSCOPIC DEVICE AND METHOD FOR DELIVERY OF MEDICAL FLUID

(75) Inventors: Marc Feinberg, Ringoes, NJ (US); Jessica Liberatore, Marlboro, NJ (US); Richard Kocharian, Princeton, NJ (US); Bruce E. Zaborowski, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 686 days.

(21) Appl. No.: 11/491,791

(22) Filed: Jul. 24, 2006

(65) Prior Publication Data

US 2008/0097391 A1    Apr. 24, 2008

(51) Int. Cl.
*A61M 25/00* (2006.01)
*A61F 11/00* (2006.01)

(52) U.S. Cl. .................... 604/528; 604/530; 606/108

(58) Field of Classification Search ............ 604/95.01, 604/158, 164.01, 528, 530, 506–508, 510, 604/198, 525, 531, 532; 606/108, 153; 623/1.11, 623/1.12
See application file for complete search history.

(56) References Cited

U.S. PATENT DOCUMENTS

| | | | | |
|---|---|---|---|---|
| 5,152,749 A | * | 10/1992 | Giesy et al. | 604/164.01 |
| 5,381,782 A | | 1/1995 | DeLaRama et al. | 128/4 |
| 5,454,787 A | | 10/1995 | Lundquist | 604/95 |
| 5,741,225 A | * | 4/1998 | Lax et al. | 604/22 |
| 6,228,051 B1 | | 5/2001 | Trumbull | 604/95 |
| 6,579,279 B1 | * | 6/2003 | Rabiner et al. | 604/528 |
| 6,743,206 B1 | * | 6/2004 | Smith et al. | 604/164.01 |
| 2002/0161114 A1 | * | 10/2002 | Gunatillake et al. | 525/100 |

FOREIGN PATENT DOCUMENTS

WO    WO2004/045672 A2    6/2004
WO    WO 2005/042079 A    5/2005

OTHER PUBLICATIONS

International Search Report dated Apr. 15, 2008.

* cited by examiner

*Primary Examiner* — Kevin C Sirmons
*Assistant Examiner* — Larry R Wilson

(57) ABSTRACT

A laparoscopic medical fluid delivery device includes a catheter having an articulating tip formed with shape memory properties and thus having a pre-shaped curvature. A tubular member is reciprocatingly slidable axially on the catheter to selectively cover and uncover portions of the articulating tip to thereby selectively vary the degree of curvature of the articulating tip. An actuator operatively linked to the tubular member selectively moves the tubular member reciprocatingly on the catheter. The pre-shaped articulating tip of the catheter is constrained by the tubular member from articulating to the pre-shaped curvature when the tubular member covers the articulating tip, and bends to a selected degree of curvature when the articulating tip is at least partially uncovered by the tubular member.

31 Claims, 52 Drawing Sheets

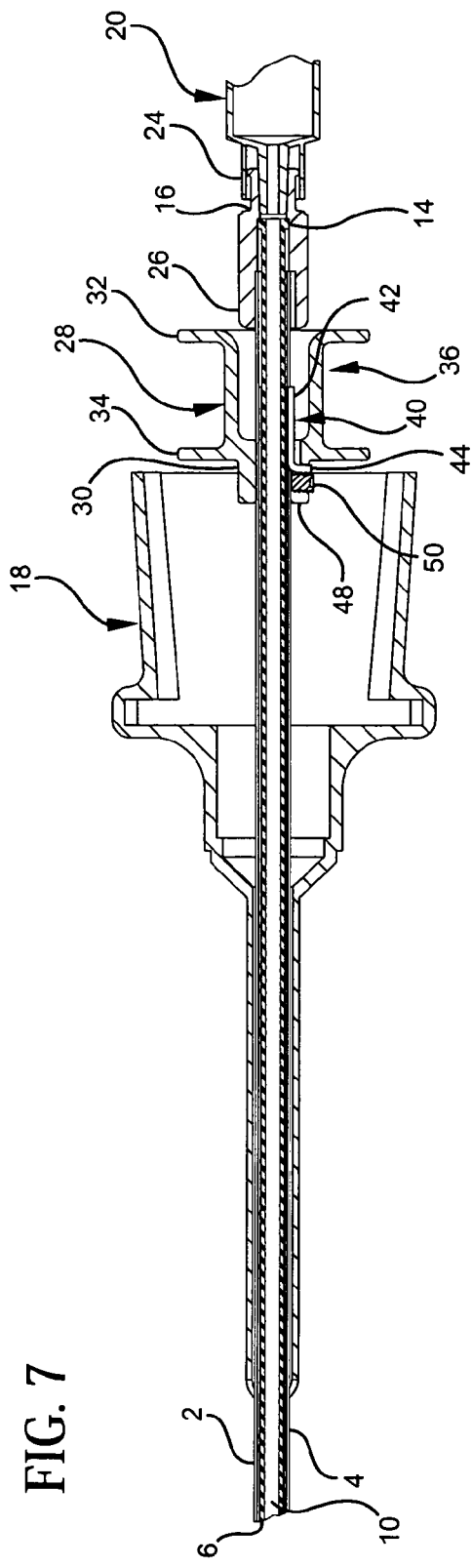
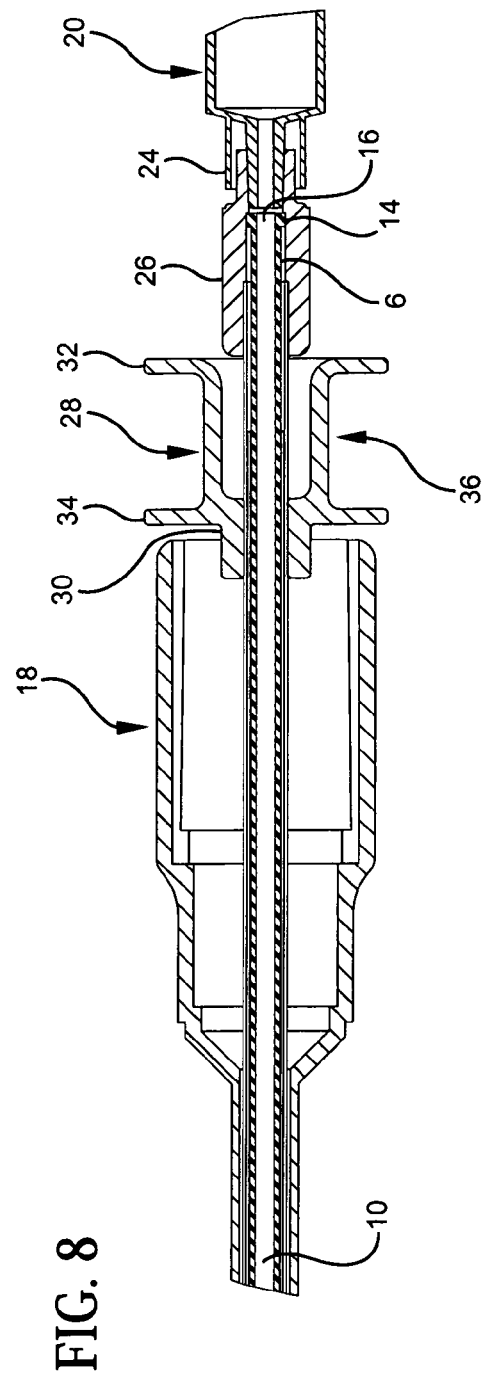
FIG. 7
FIG. 8

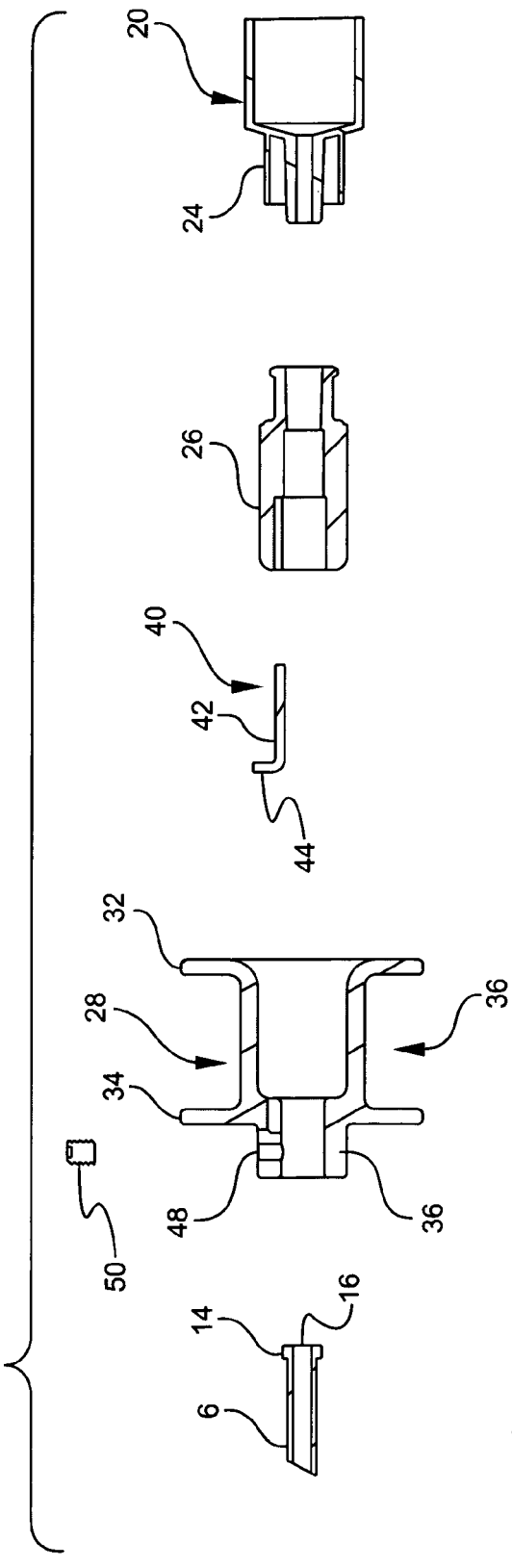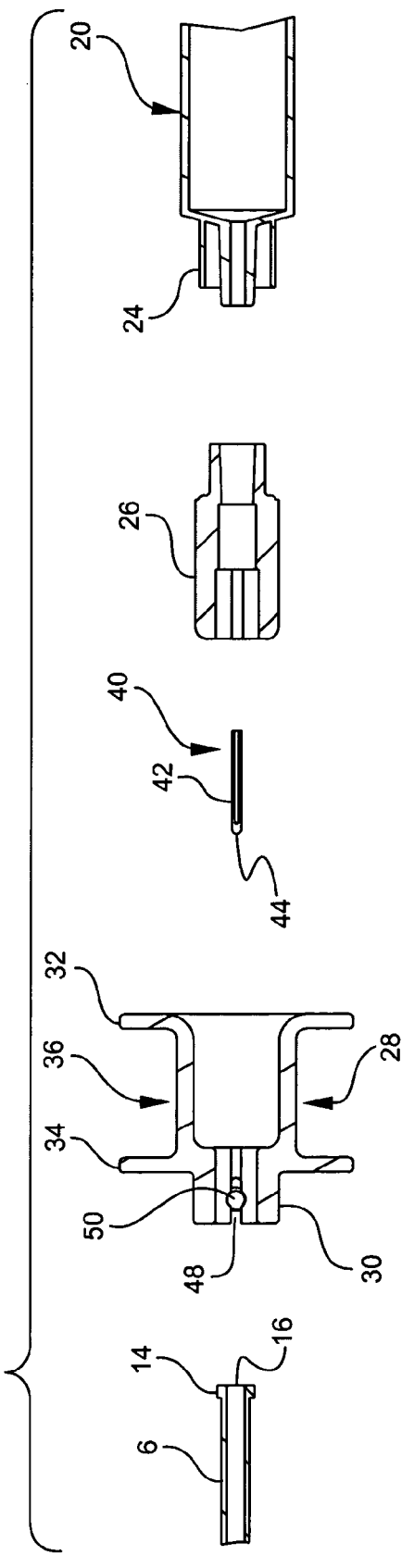

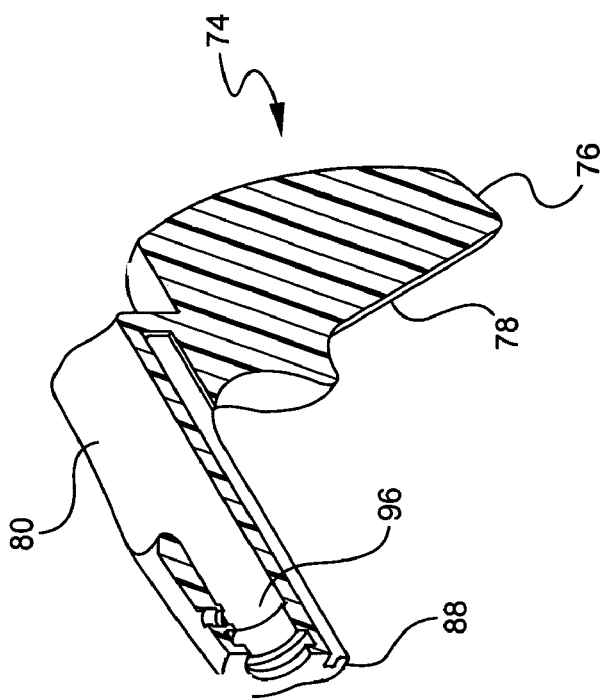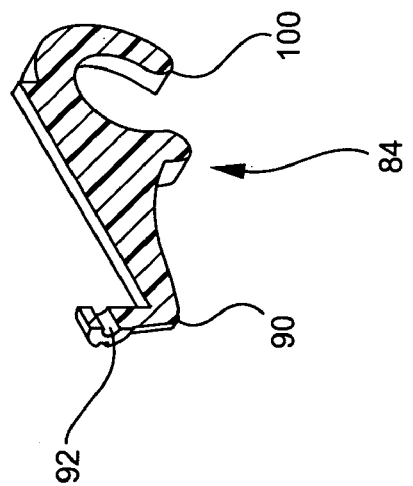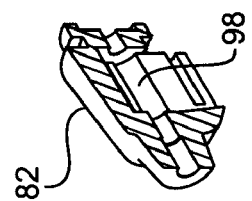
FIG. 26

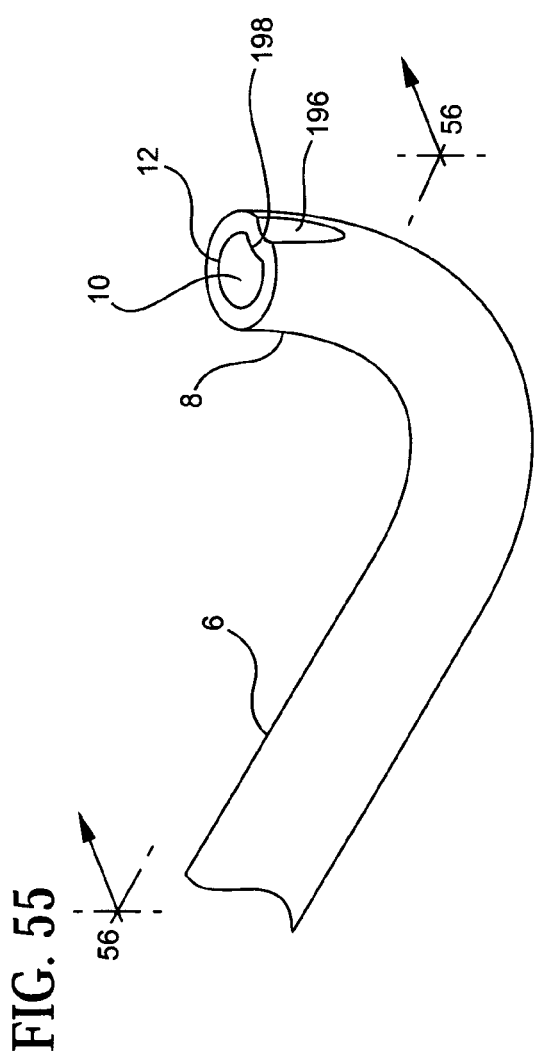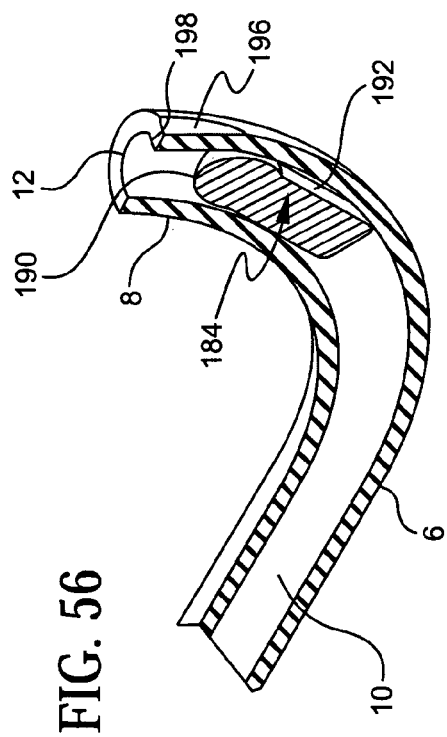
FIG. 55
FIG. 56

ARTICULATING LAPAROSCOPIC DEVICE AND METHOD FOR DELIVERY OF MEDICAL FLUID

BACKGROUND OF THE INVENTION

1. Field of the Invention

The present invention generally relates to laparoscopic devices, and more particularly relates to bendable laparoscopic applicators of medical fluids or agents, such as sealants, adhesives, flowable haemostatic agents and antibiotics. This invention also particularly relates to methods for delivering such medical fluids to a patient.

2. Description of the Prior Art

Certain conventional laparoscopic adhesive or sealant applicators include a straight and rigid elongated tubular member having an internal lumen communicating with a distal opening through which the adhesive or sealant passes. Because of their rigidity, these applicators are difficult to maneuver from the opposite proximal end of the tubular member for precisely directing the adhesive or sealant to the targeted area, without dripping the adhesive or sealant on non-targeted tissue. Oftentimes, laparoscopic delivery of such medical fluids requires the ability to reach behind anatomical structures (e.g., organs, large vessels and the like) to the targeted site, which rigid laparoscopic delivery devices are incapable of reaching.

There are a number of known laparoscopic devices that have been invented which feature a bendable or deflectable distal end. For example, published PCT (Patent Cooperation Treaty) Application Serial No. PCT/US2003/036210 (International Publication No. WO 2004/045672, published on Jun. 3, 2004), having the named inventors Parag Karmarkar and Robert J. Lederman, discloses a variable curved catheter that allows the physician to vary the radius of curvature of the distal catheter tip. The catheter includes a longitudinally extending inner lumen defined by a tubular member which is adapted to deliver a therapeutic agent to a patient. The tubular member is multi-slotted to achieve flexibility of the distal tip. The slots in the tubular member provide collapsible space in order to achieve curvature of the tip. A pull wire attached to a control knob is used to adjust the curvature of the distal tip. The disclosed Karmarkar et al. variable curved catheter is a rather complicated device structurally and operationally. It is complex and labor intensive to manufacture, and requires a two-handed operation.

A torquable catheter having a flexible, steerable distal tip is disclosed in U.S. Pat. No. 5,454,787, which issued to Ingemar H. Lundquist. The torquable catheter includes first and second tubular members, where the second tubular member is disposed axially within the first tubular member. Each tubular member has a plurality of slots formed therein and spaced apart longitudinally. The catheter is covered in a flexible coating, such as heat shrink tubing. Bending of the distal tip is effected by tensioning a pull-ribbon or wire connected to a control knob. This device is primarily utilized for performing RF ablation, and therefore includes a radio-frequency electrode. The operation and structure of the Lundquist torquable catheter is similar in many respects to the operation and structure of the Karmarkar et al. device discussed previously. It, too, is complex structurally, and labor-intensive and costly to manufacture.

U.S. Pat. No. 5,381,782, which issued to Alan DeLaRama et al., discloses bi-directional and multi-directional miniscopes. As can be seen from FIG. 7 of the DeLaRama et al. patent, the miniscope includes a catheter body having a tubular spring frame with a plurality of relief slots formed therein to allow the deflection of the spring frame. Extending longitudinally through the catheter body and spring frame is a pair of activation wires which are encased by a pair of support sleeves. The spring frame is deflected by stressing the activation wires by subjecting either of the wires to a tensile force. The DeLaRama et al. multi-slotted miniscope is another example of a structurally complicated laparoscopic device which is also costly to manufacture.

A laparoscopic sealant applicator is disclosed in U.S. Pat. No. 6,228,051, which issued to Horace R. Trumbull. The Trumbull applicator is used for the selective directional application of one or more liquids, such as a sealant, to a surgical site. As shown in FIGS. 2a and 2b of the Trumbull patent, the applicator includes a flexible shaft having a series of hinges which are interconnected so as to enable the bending of the flexible shaft. The hinges are described as being wedges pivotally interlocked at their tops, with triangular slots separating adjacent wedges. A control or push/pull wire runs through the flexible shaft. When the wire is retracted or withdrawn by a control knob, the wedges of the flexible shaft are allowed to fold down upon themselves, causing articulation of the flexible shaft.

One of the drawbacks of the Trumbull laparoscopic sealant applicator relates to the push/pull wire. The push strength required to straighten the flexible shaft would dictate that the wire would need to be of a relatively substantial diameter in order to resist bulging when actuated.

As with the other devices discussed previously, the Trumbull laparoscopic sealant applicator relies on metal tubing to articulate. Thin wall stainless steel tubing will fracture due to metal fatigue, and cold working increases the hardness as it is flexed. Therefore, the more the device is used, the more difficult it is to operate, and failure is inevitable. Furthermore, the Trumbull laparoscopic sealant applicator, like the other devices previously discussed, is complicated in structure and difficult to operate.

Another problem in the medical profession which must be addressed when using such laparoscopic fluid delivery devices such as described previously is the need to efficiently deliver trapped medical fluids in the laparoscopic instrument. Physicians desire to utilize all of the medical fluid in a delivery device with little waste. A laparoscopic instrument is typically about 28 to about 45 cm long and, depending on the internal lumen diameter, can trap a considerable amount of medical fluid (e.g., sealants, adhesives, haemostatic agents, antibiotics and the like). Such medical fluids are relatively expensive.

At least one laparoscopic fluid delivery device manufactured by Baxter Healthcare Corporation of Deerfield, Ill., uses a ramrod in its device to extract the fluid therein. This solution requires two hands, one to aim the distal tip of the instrument at the targeted site, and the other to feed the ramrod down the catheter. Furthermore, the ramrod has a much different tactile feel to the physician, and can affect his ability to precisely deliver a medical fluid to the targeted site in the patient.

OBJECTS AND SUMMARY OF THE INVENTION

It is an object of the present invention to provide a laparoscopic medical fluid applicator for the selective directional application of a medical fluid to a surgical site.

It is another object of the present invention to provide a laparoscopic fluid delivery device which allows for one-handed operation by the physician.

It is a further object of the present invention to provide a laparoscopic fluid delivery device which has a distal end exhibiting variable degrees of curvature selectable by the physician.

It is still another object of the present invention to provide a laparoscopic fluid delivery device which has the capability for 360° rotation of an articulating distal tip for precise delivery of medical fluids to a targeted tissue.

It is yet a further object of the present invention to provide a laparoscopic fluid delivery device which accepts single or dual syringe systems for delivery of unmixed and mixed medical fluids to a patient.

It is still another object of the present invention to provide a laparoscopic fluid delivery device which is simple in construction and operation.

It is a further object of the present invention to provide a laparoscopic fluid delivery device which overcomes the inherent disadvantages of known laparoscopic devices.

It is another object of the present invention to provide a device and method for dispensing medical fluid trapped in the internal lumen of a laparoscopic device.

It is yet another object of the present invention to provide a method and apparatus for laparoscopically delivering trapped medical fluid in an internal lumen of a fluid delivery device, which apparatus does not affect the tactile feel of the fluid delivery device, thus enabling the physician to precisely deliver a medical fluid to the patient at a targeted site.

It is still a further object of the present invention to provide a method and device for dispensing medical fluid trapped in the internal lumen of a laparoscopic device, which method is a cost effective approach to dispensing such medical fluid, and which device used to dispense such medical fluid is relatively small and simple to operate.

In accordance with one form of the present invention, an articulating laparoscopic device for delivering medical fluids to a patient includes a fixed outer, preferably stainless steel, tube, a moveable inner, preferably stainless steel, tube situated within the fixed outer stainless steel tube, and a flexible catheter made from a material having memory retention properties which is situated within the moveable inner stainless steel tube. The distal end of the flexible catheter is preshaped to preferably a 90° degree and is maintained beneath the inner stainless steel tube.

When the inner tube is moved axially within the outer tube, it covers and uncovers the flexible tubing, allowing variable portions of the distal end of the flexible catheter to be exposed and which, accordingly, allows variable degrees of curvature of the flexible catheter.

The flexible catheter includes a lumen formed axially therein, an opening in its articulating distal tip and an opening in its proximal end opposite the distal end. The openings communicate with the lumen to allow the passage of a medical fluid, such as a sealant, adhesive, haemostatic agent, antibiotic or the like, to be delivered through the opening in the distal end to a targeted tissue site within a patient. The proximal end of the lumen may be fitted with a standard luer lock connector, so that it is matable with a syringe having a luer lock tip and containing a medical fluid. It should be noted here that although the catheter is described as having a single lumen, the catheter may be formed with multiple lumens, and such an embodiment is envisioned to be within the scope of the present invention.

In one embodiment, the laparoscopic medical fluid delivery device includes a lap collar defined by two spaced apart, radially extending flanges. The lap collar is linked to the inner tube axially. The two radially extending flanges define a finger slot therebetween. The surgeon positions two fingers to straddle the finger slot to enable movement of the inner tube in the distal and proximal directions. The surgeon then removes his or her fingers from the finger slot so as not to inadvertently change the selected curvature of the articulating tip, and may then place his or her fingers on the neck of the syringe. With his or her thumb, the surgeon pushes on the plunger of the syringe to dispense medical fluid therefrom, through the lumen of the flexible catheter and out the articulating distal tip thereof to the targeted site, as is done with conventional applicators with which the surgeon is already familiar.

In another form of the present invention, the laparoscopic medical fluid delivery device of the present invention includes a handle with a pivoting trigger attached thereto. The trigger is linked to a collar that is attached to the inner tube to move the tube axially to cover and uncover the flexible catheter and the articulating distal tip thereof.

In yet a further variation of the present invention, the laparoscopic medical fluid delivery device may include a handle with a reciprocating trigger piece that is slidably attached thereto. The trigger piece is operatively coupled to the inner tube. The handle includes a barrel for receiving a syringe filled with a medical fluid. The surgeon grasps the handle with three fingers, the trigger piece with his first finger, and rests his thumb on the plunger of the syringe fitted into the barrel of the handle. The surgeon manipulates the trigger piece back and forth to move the inner tube to cover and uncover the flexible catheter to whatever degree of articulation of the catheter's tip is desired, and he presses the plunger with his thumb to dispense fluid from the syringe, through the movement of the flexible catheter and the distal tip thereof to the targeted tissue site within the patient's body.

In yet a further form of the present invention, the handle of the laparoscopic fluid delivery device may include a rotatable nose piece mounted to the flexible catheter so that the articulating tip of the flexible catheter may be turned clockwise or counterclockwise to any desired position by rotating the nose piece in order to precisely direct medical fluid to a targeted tissue site.

In yet a further variation of the present invention, the handle of the laparoscopic medical fluid delivery device may include an actuator thumb rest which is operatively linked to the plunger of the syringe. The surgeon grasps the handle with three fingers, the trigger piece with his first finger and comfortably rests his thumb on the actuator thumb rest. By pushing forward on the thumb rest, the surgeon will draw the plunger into the syringe to dispense medical fluid therefrom, through the lumen of the flexible catheter and the distal tip opening thereof to the targeted tissue site.

In accordance with another form of the present invention, a device and method for delivering trapped medical fluid in a laparoscopic instrument is described herein. With respect to the various embodiments of the laparoscopic delivery device described previously, a specially constructed syringe having a luer lock connection is mated to the luer lock connection of the flexible catheter. The syringe includes air to dispense low viscosity fluids trapped in the lumen of the flexible catheter, or a non-compressible fluid (e.g., a saline solution) for more viscous medical fluids trapped in the flexible catheter. The syringe has mounted in the luer lock connector thereof a lap seal having an oversized bulbous tip and a smaller diameter rod extending therefrom. The rod may be connected to a suture or other connecting line which is coiled within the syringe. The bulbous tip of the lap seal has a diameter which approximates the inner diameter of the flexible catheter's lumen.

The surgeon loads the specially made syringe into the barrel on the handle of the laparoscopic delivery device, and forces the plunger to move therein. The plunger forces the lap seal out of the luer lock connector of the syringe tip and into the lumen of the flexible catheter. The lap seal, traveling through the lumen, forces the medical fluid trapped therein out of the distal tip of the catheter to the targeted tissue site. The length of the suture or connecting line limits the travel of the lap seal so that the lap seal does not travel beyond the opening in the distal tip of the catheter. Alternatively, the lap seal need not be tethered to the syringe, but rather is blocked from entering the patient's body cavity by a deformation formed at the distal end of the flexible catheter that slightly narrows the inner diameter of the lumen so that the tip diameter is less than the diameter of the bulbous end of the lap seal.

Although the syringe and lap seal combination is described herein as being used with the laparoscopic fluid delivery device of the present invention, it is envisioned to be within the scope of the present invention to employ the syringe and lap seal with any laparoscopic device where medical fluid remains trapped in the lumen thereof.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 7 is an enlarged cross-sectional view of a portion of the laparoscopic medical fluid delivery device of the present invention shown in FIG. 5.

FIG. 8 is an enlarged cross-sectional view of a portion of the laparoscopic medical fluid delivery device of the present invention shown in FIG. 6.

FIG. 12 is an exploded, cross-sectional view of a portion of the laparoscopic medical fluid delivery device of the present invention shown in FIGS. 1-11.

FIG. 13 is an exploded, cross-sectional view of the laparoscopic medical fluid delivery device of the present invention shown in FIGS. 1-12.

FIG. 26 is an exploded, isometric/cross-sectional view of portions of the laparoscopic medical fluid delivery device of the present invention shown in FIGS. 21-25.

FIG. 55 is an isometric view of the distal tip portion of the catheter of a laparoscopic medical fluid delivery device of the present invention shown in FIG. 54.

FIG. 56 is an isometric, cross-sectional view of the distal tip portion of the catheter shown in FIG. 55, taken along line 56-56 of FIG. 55.

DETAILED DESCRIPTION OF THE PREFERRED EMBODIMENTS

Figure 1:
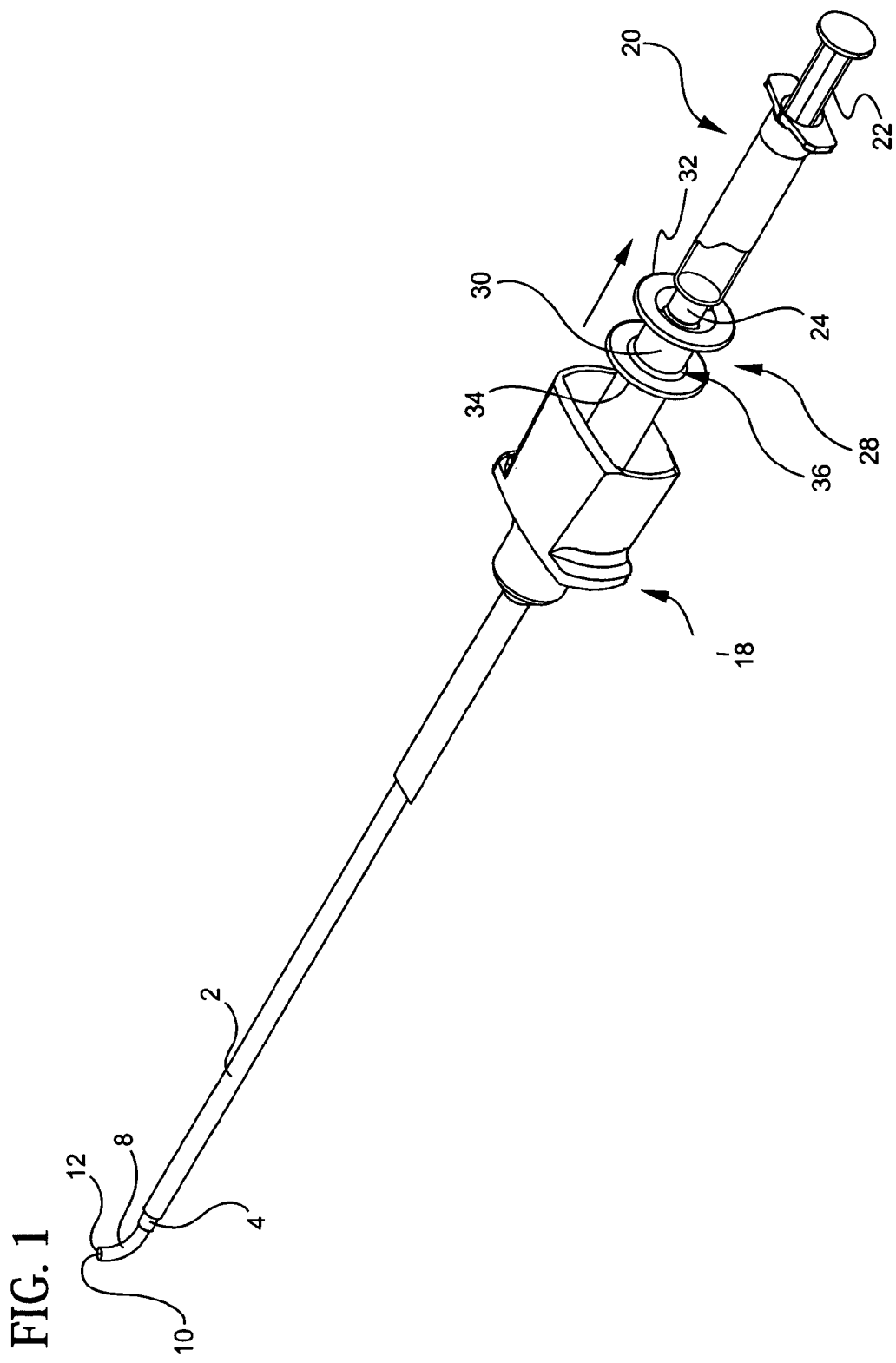
FIG. 1 is a rear isometric view of a laparoscopic medical fluid delivery device constructed in accordance with one form of the present invention.
Figure 2:
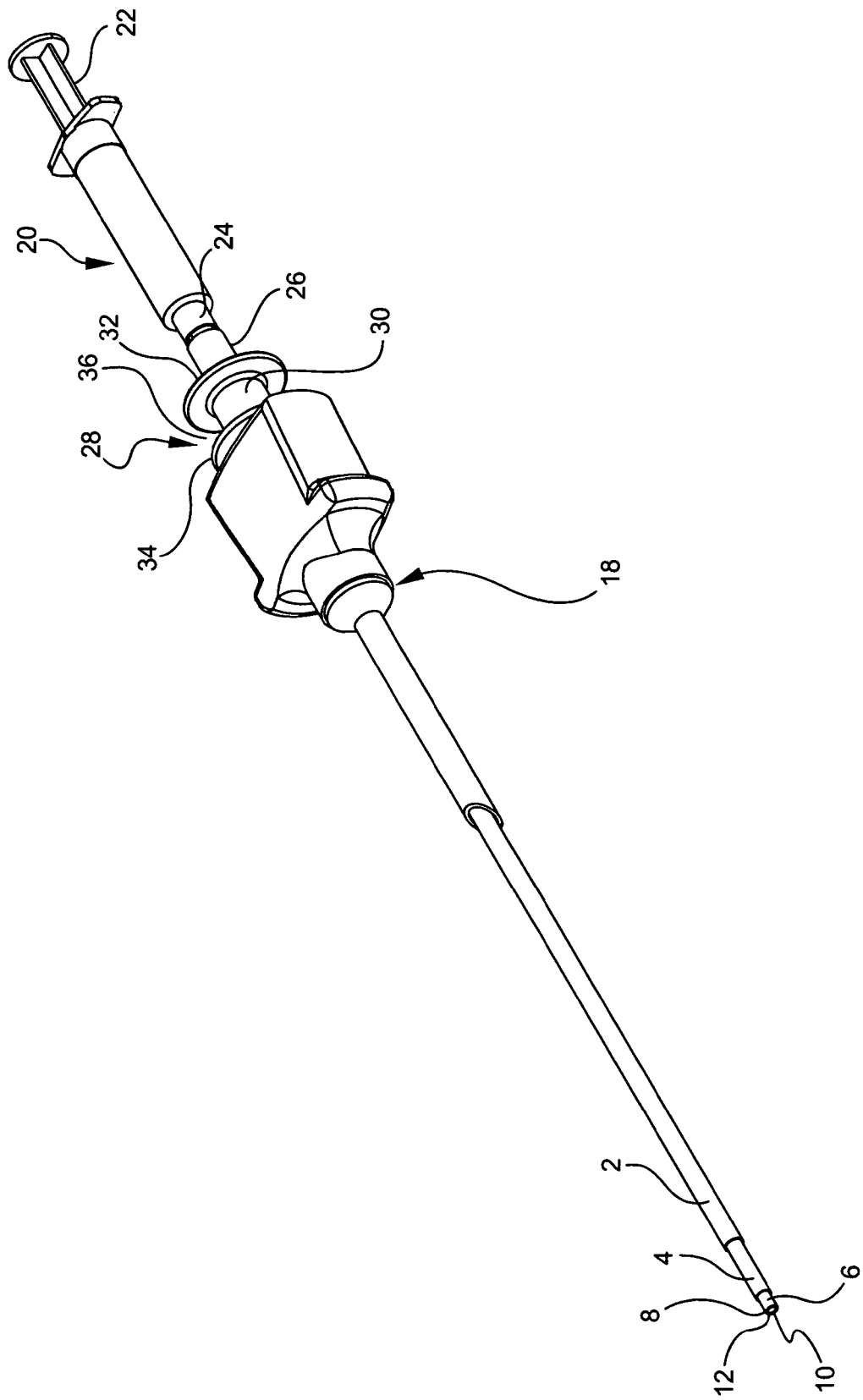
FIG. 2 is a front isometric view of the laparoscopic medical fluid delivery device of the present invention shown in FIG. 1.
Figure 3:
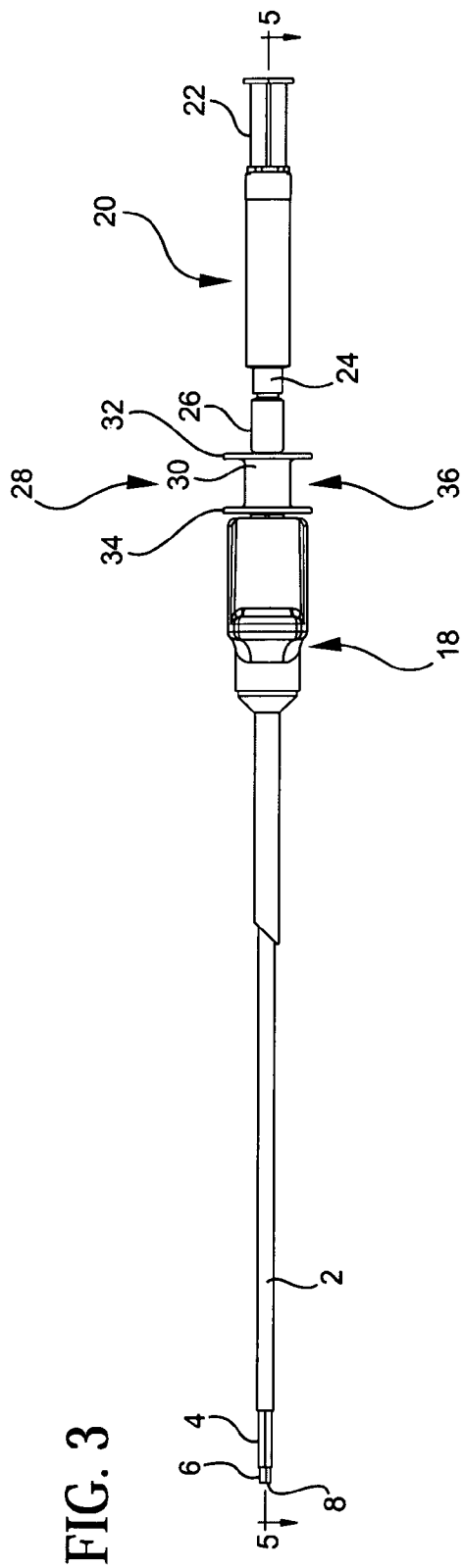
FIG. 3 is a top view of the laparoscopic medical fluid delivery device of the present invention shown in FIGS. 1 and 2.
Figure 4:
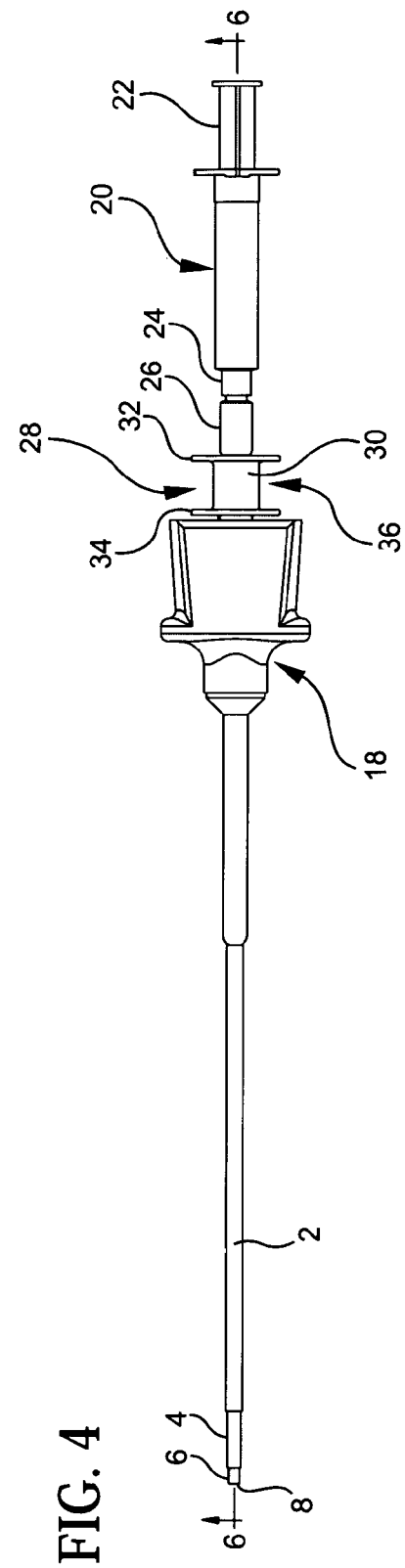
FIG. 4 is a side view of the laparoscopic medical fluid delivery device of the present invention shown in FIGS. 1-3.
Figure 5:
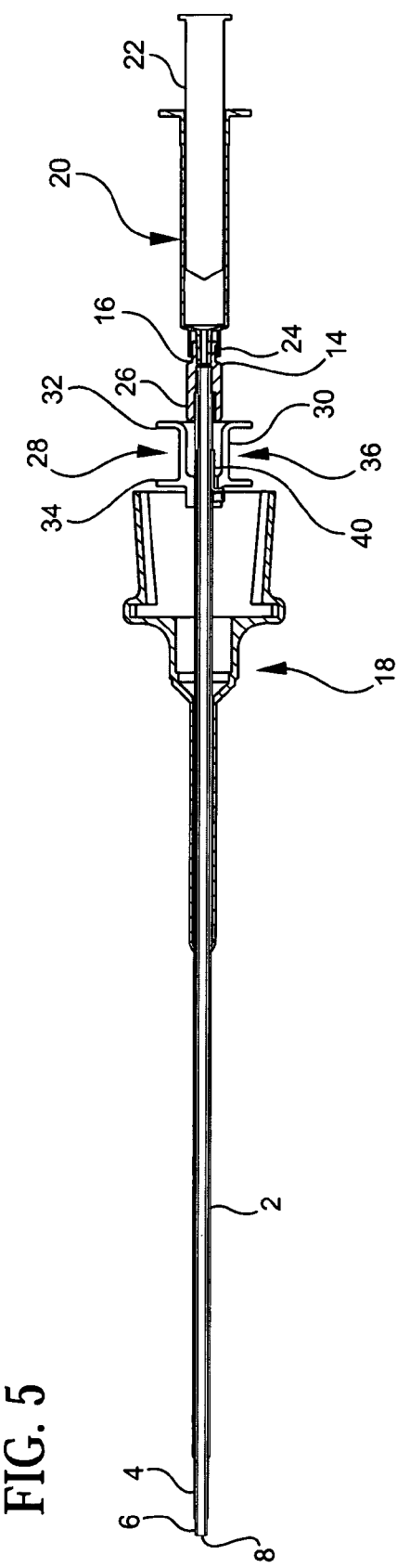
FIG. 5 is a cross-sectional view of the laparoscopic medical fluid delivery device shown in FIGS. 1-4, taken along line 5-5 of FIG. 3.
Figure 6:
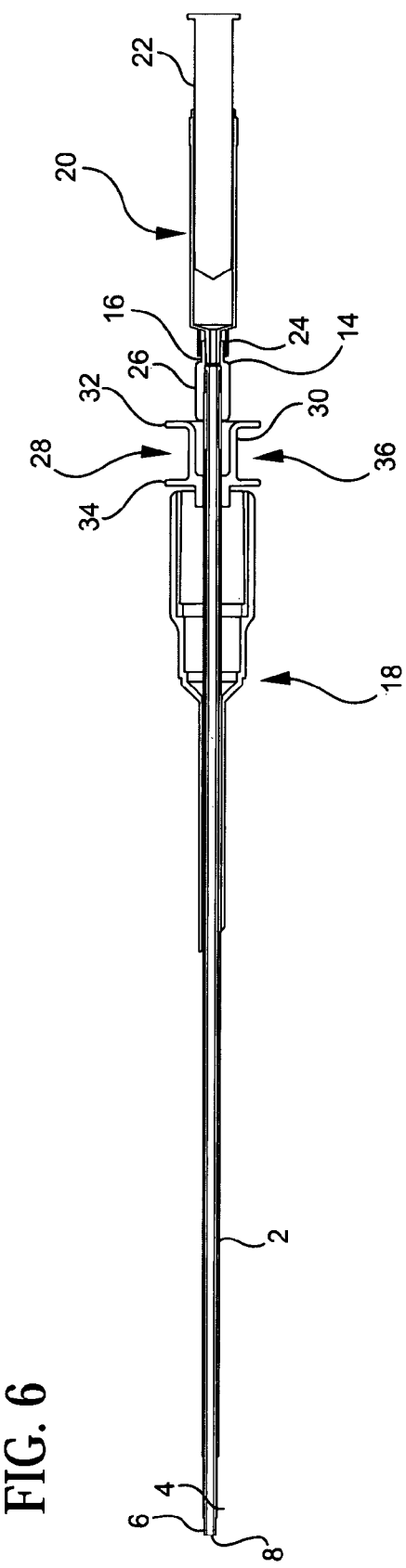
FIG. 6 is a cross-sectional view of the laparoscopic medical fluid delivery device of the present invention shown in FIGS. 1-5, taken along line 6-6 of FIG. 4.
Figure 9:
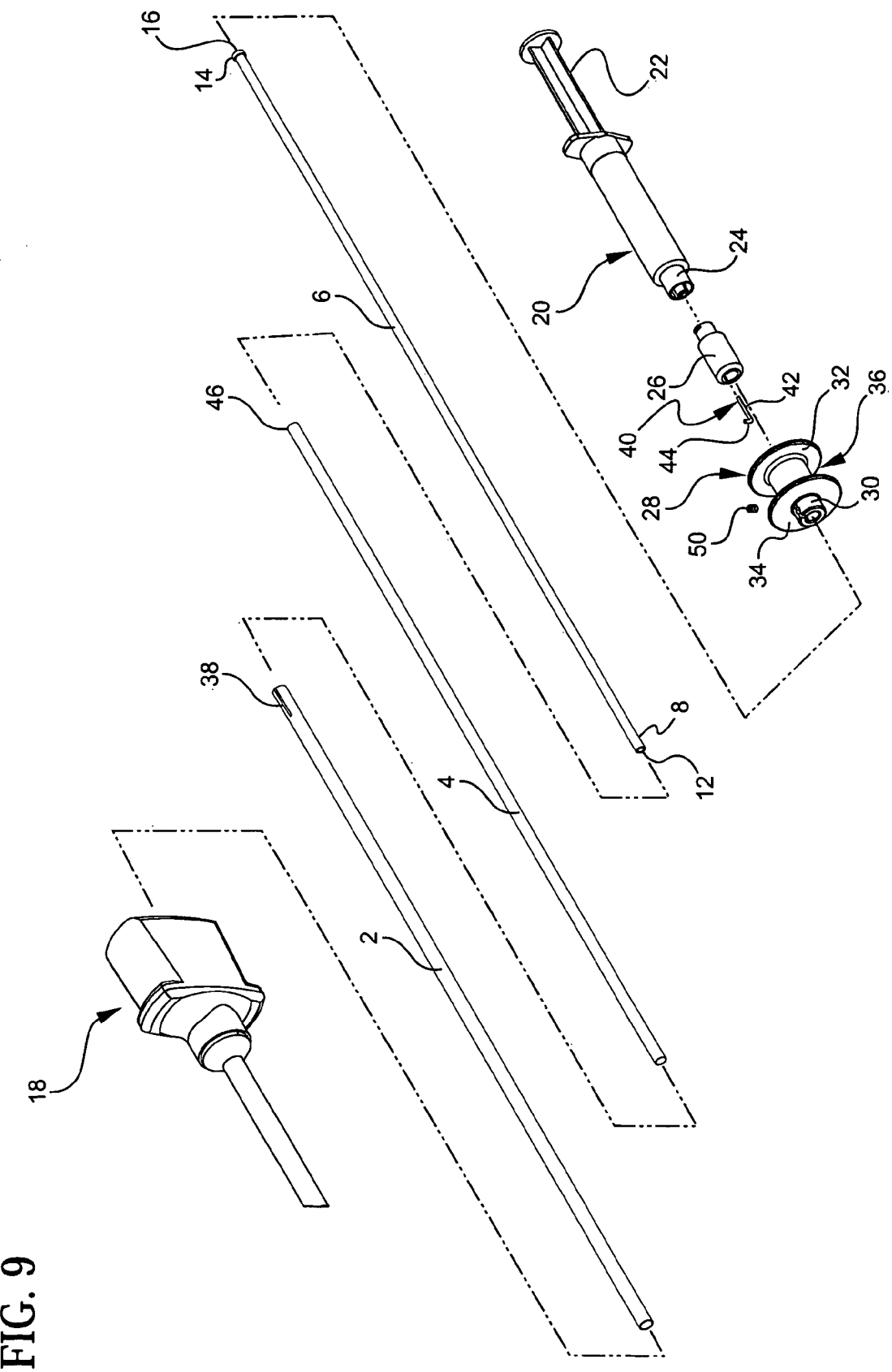
FIG. 9 is an exploded view of the laparoscopic medical fluid delivery device of the present invention shown in FIGS. 1-8.
Figure 10:
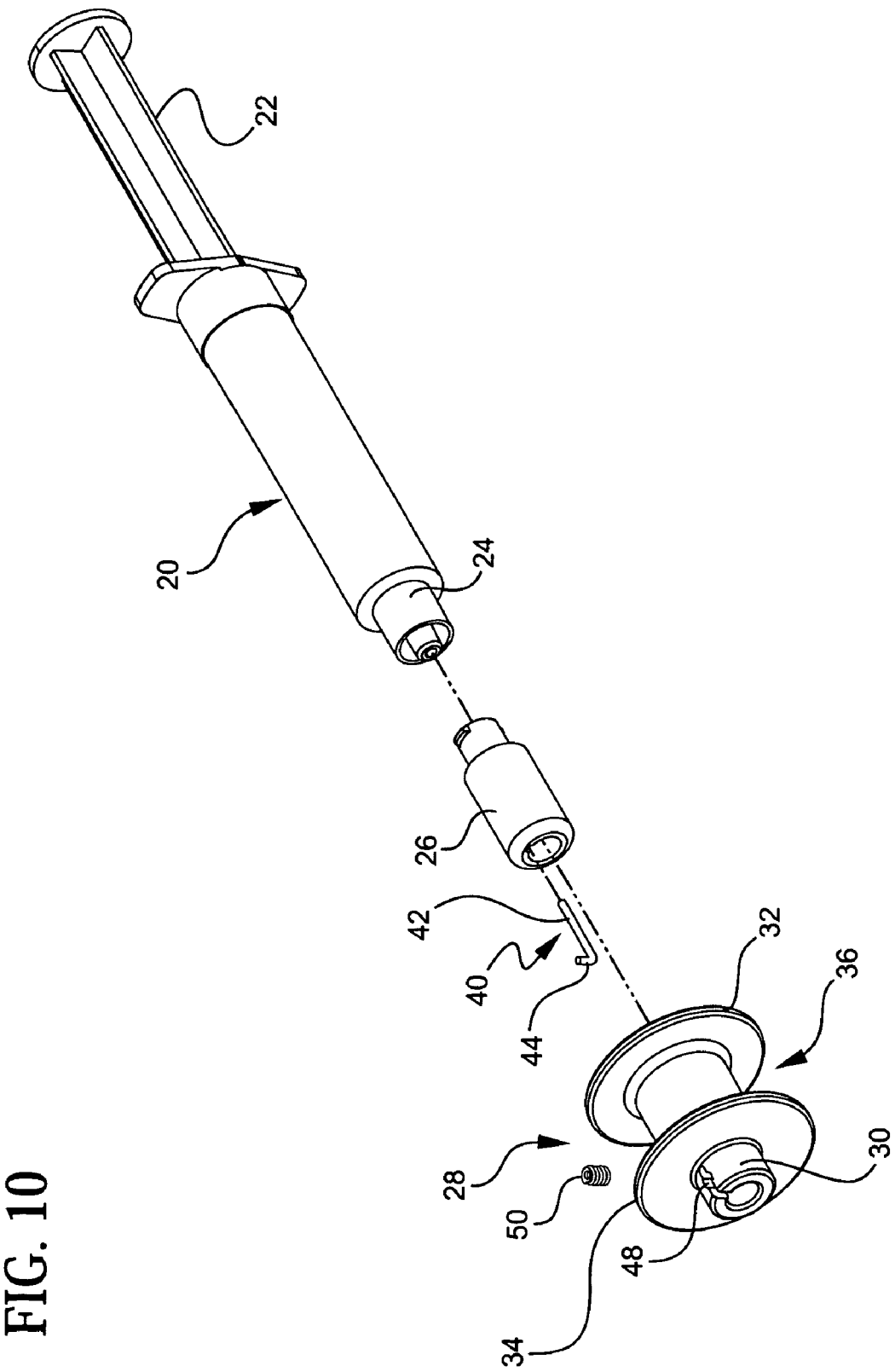
FIG. 10 is an exploded view of a portion of the laparoscopic medical fluid delivery device of the present invention shown in FIGS. 1-9.
Figure 11:
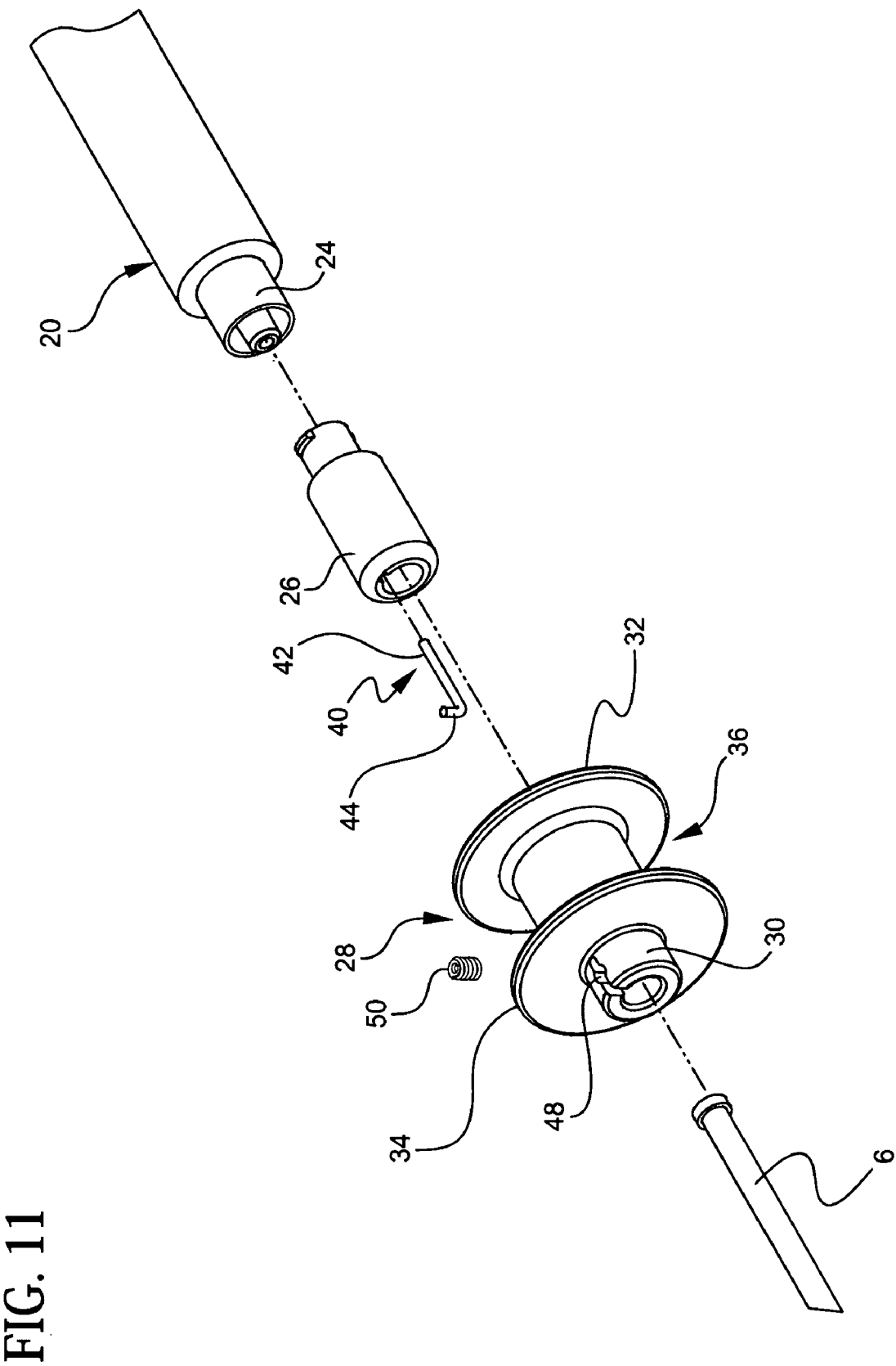
FIG. 11 is an exploded view of a portion of the laparoscopic medical fluid delivery device of the present invention shown in FIGS. 1-10.

Referring initially to FIGS. 1-15 of the drawings, it will be seen that an articulating laparoscopic device for delivering medical fluids to a patient and constructed in accordance with one form of the present invention includes an outer tubular member 2, preferably formed of stainless steel and preferably rigid, and having a bore formed axially therein along the length thereof, and an inner tubular member 4, which is also preferably formed from stainless steel and preferably rigid, and which resides at least along a portion thereof radially within the bore of the outer tubular member 2 and extending along the length thereof. The inner tubular member 4 also includes a bore formed axially therethrough which extends along the length thereof.

The laparoscopic fluid delivery device of the present invention further includes a catheter 6 having at least a flexible distal end tip portion 8 and defining a lumen 10 extending axially along the length thereof for the passage of medical fluids therethrough. The distal tip portion 8 has an opening 12 formed at the axial end of the catheter 6. The catheter 6 also includes a proximal end 14 situated opposite the distal end 8, which also has an opening 16 formed in the axial end thereof. The openings 12, 16 in the distal and proximal ends 8, 14 of the catheter communicate with the catheter lumen 10 to allow the passage of medical fluid through the proximal end opening 16, the lumen 10 and the distal end opening 12 formed in the tip portion to a targeted tissue site within the patient. The inner tubular member 4 is movable axially within the outer tubular member 2 to cover and uncover the tip portion 8 of the catheter 6, as will be described in greater detail.

The internal catheter 6 is preferably an elastomeric flexible catheter that has been pre-shaped to about a ninety degree (90°) angle at its distal end, and is maintained beneath the inner tubular member 4 of the device, with its distal end 8 being covered and uncovered when the inner tubular member is moved in relation to the catheter and the outer tubular member 2. When the inner tubular member 4 is moved axially, it covers and uncovers the tip portion 8 of the flexible catheter 6, allowing selectable lengths of the tip portion 8 of the catheter to be exposed. Since at least the tip portion 8 of the catheter is pre-shaped, exposing selectable lengths of the tip portion provides for a variable degree of curvature of the exposed portion of the catheter 6. Thus, by maneuvering the inner tubular member 4, the physician may select whatever angle, from zero degrees (0°) to ninety degrees (90°), he or she desires as being appropriate for reaching the targeted tissue site to apply the medical fluid (e.g., adhesive, sealant, haemostatic agent, antibiotic or the like) thereat.

It is envisioned to be within the scope of the present invention to have the catheter 6 formed entirely from a flexible elastomeric material, or just the articulating tip portion 8 thereof, where the tip portion 8 is pre-shaped to a ninety degree (90°) angle or some other curvature. A suitable elastomeric material which may be used for the catheter 6, or at least the articulating tip portion 8 thereof, is PEBAX® 7033 polyester block amide, a plasticizer-free thermoplastic polymer elastomer manufactured by Arkema of Puteanx, France. It is also envisioned to be within the scope of the present invention to make the catheter 6 from materials other than a flexible elastomeric material, including those materials having shape memory properties, such as the material commonly referred to as Nitinol, which is a shape-memory alloy being formed from an intermetallic compound of nickel and titanium.

The laparoscopic fluid delivery device of the present invention may be used with or without a trocar 18, such as that shown in FIGS. 1-9 of the drawings, depending of course on the requirements of the surgeon and the surgery being performed.

Figure 14:
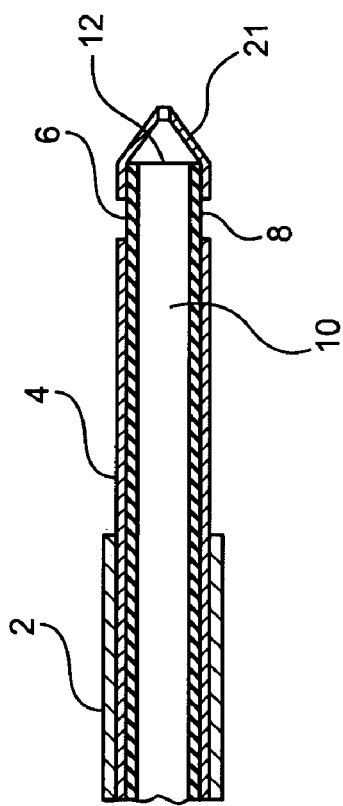
FIG. 14 is a cross-sectional view of the distal tip portion of a laparoscopic medical fluid delivery device of the present invention showing the catheter thereof in a non-articulated state, and also illustrating the use of a one-way seal on the catheter.
Figure 15:
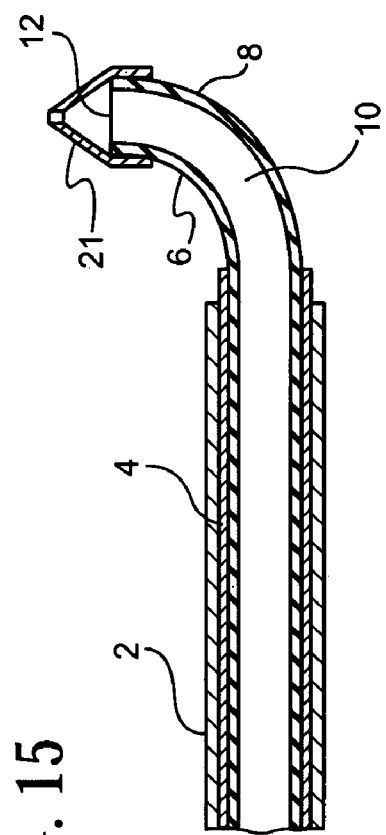
FIG. 15 is a cross-sectional view of the distal tip portion of a laparoscopic medical fluid delivery device of the present invention and showing the catheter in an articulated state, and also illustrating the use of a one-way seal on the catheter.
Figure 16:
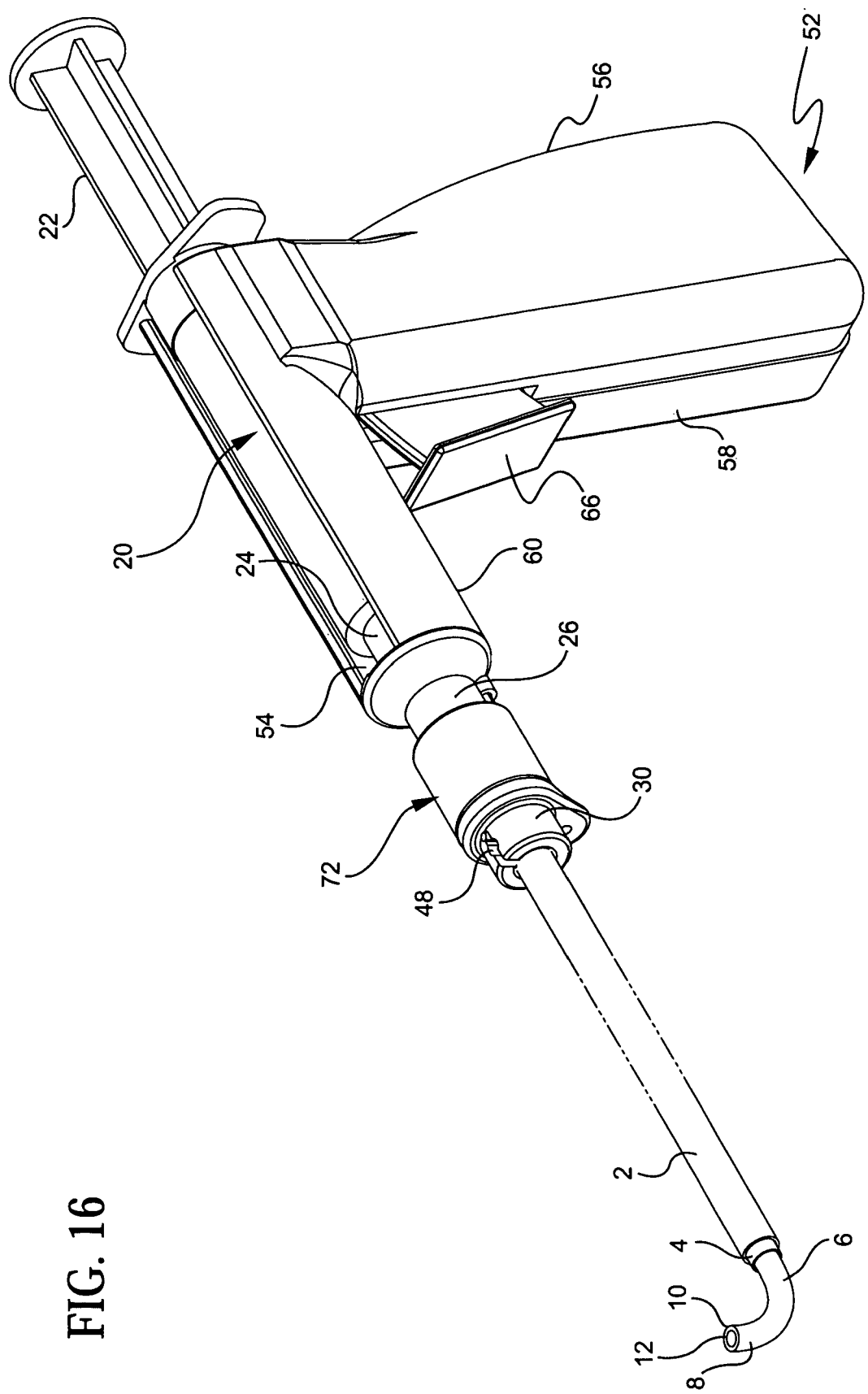
FIG. 16 is a front isometric view of a laparoscopic medical fluid delivery device constructed in accordance with a second form of the present invention.
Figure 17:
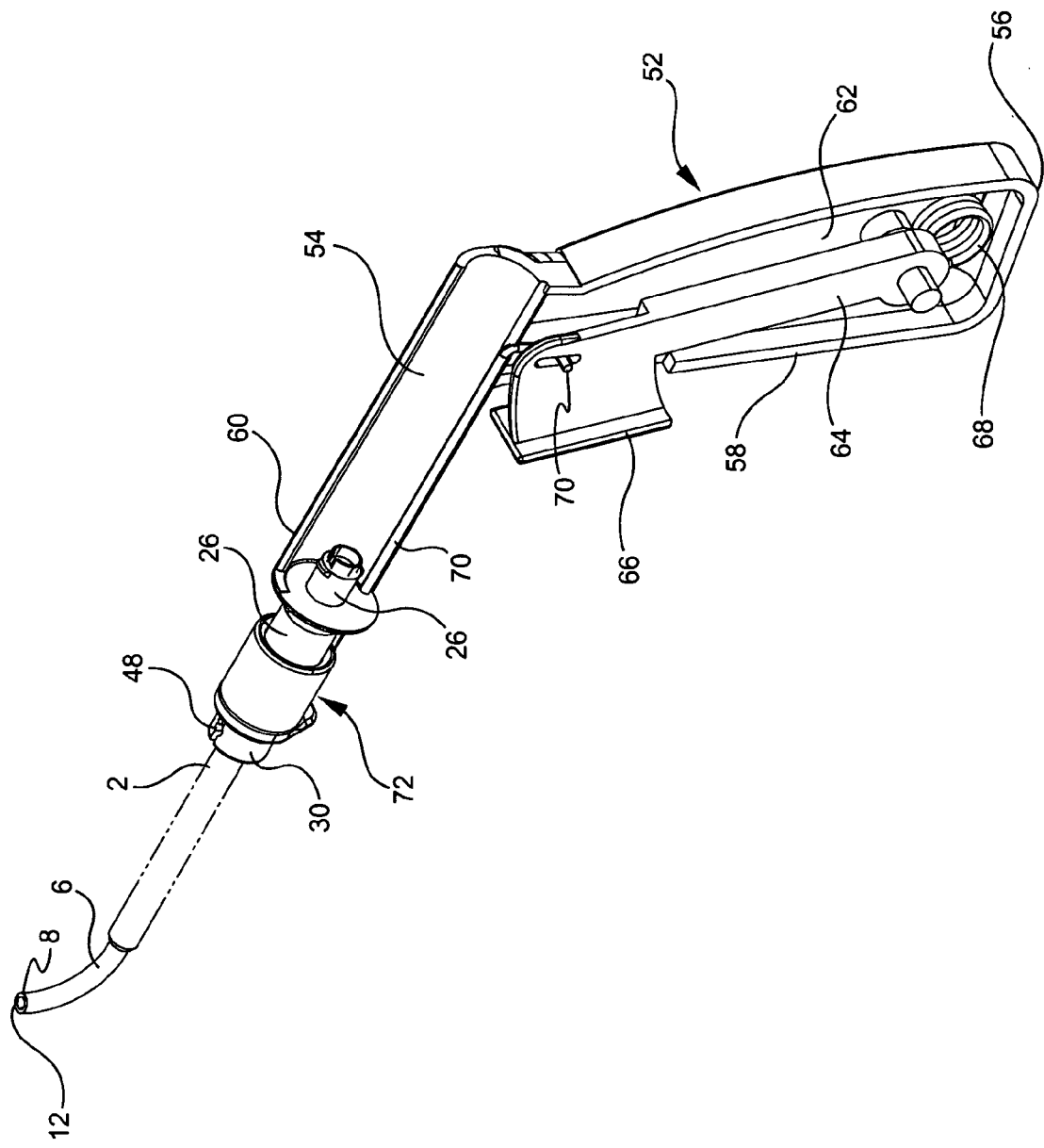
FIG. 17 is a rear isometric view of the laparoscopic medical fluid delivery device of the present invention shown in FIG. 16, with a portion of the housing thereof broken away to illustrate the internal components thereof.
Figure 18:
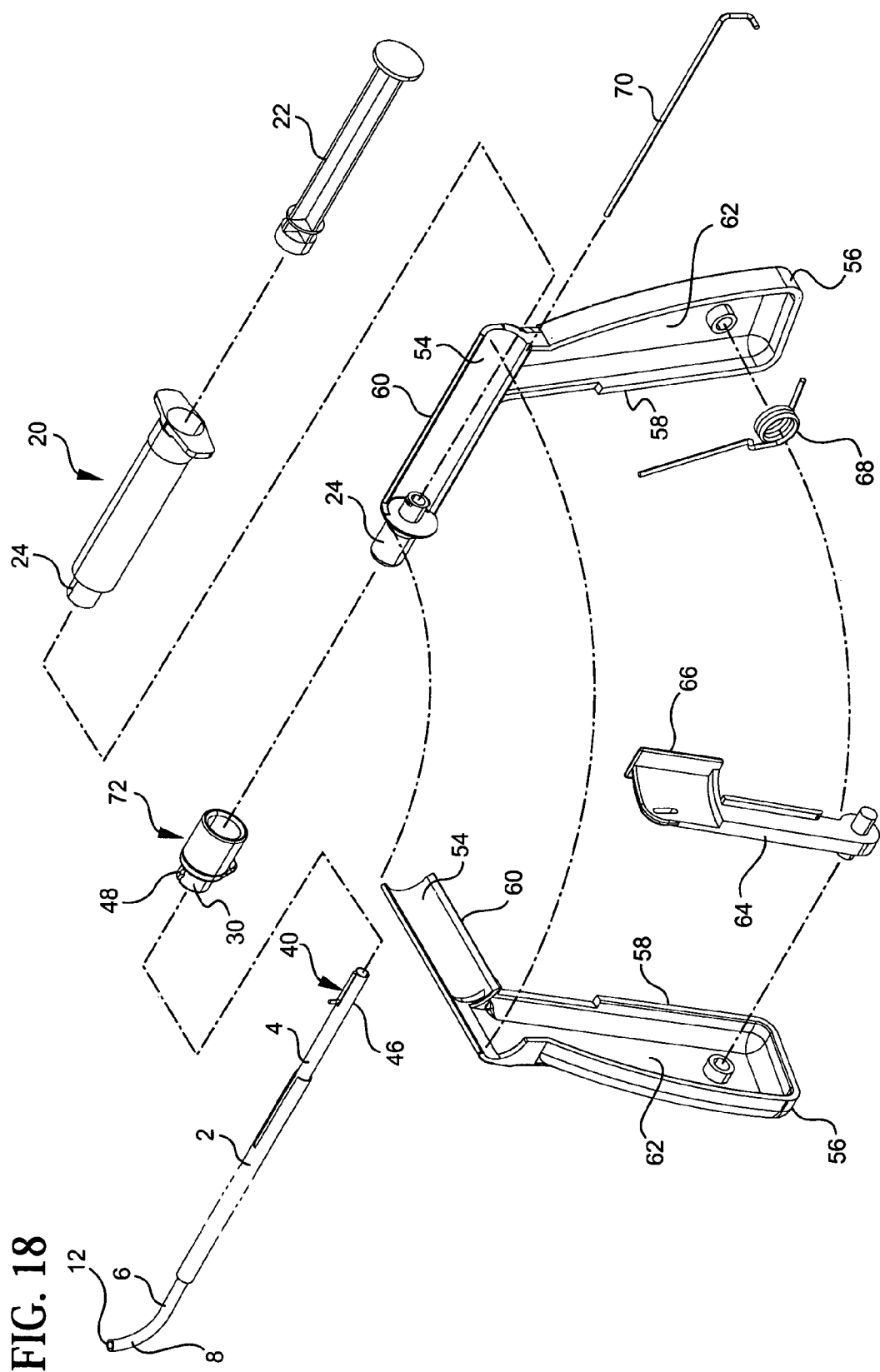
FIG. 18 is an exploded, isometric view of the laparoscopic medical fluid delivery device of the present invention shown in FIGS. 16 and 17.
Figure 19:
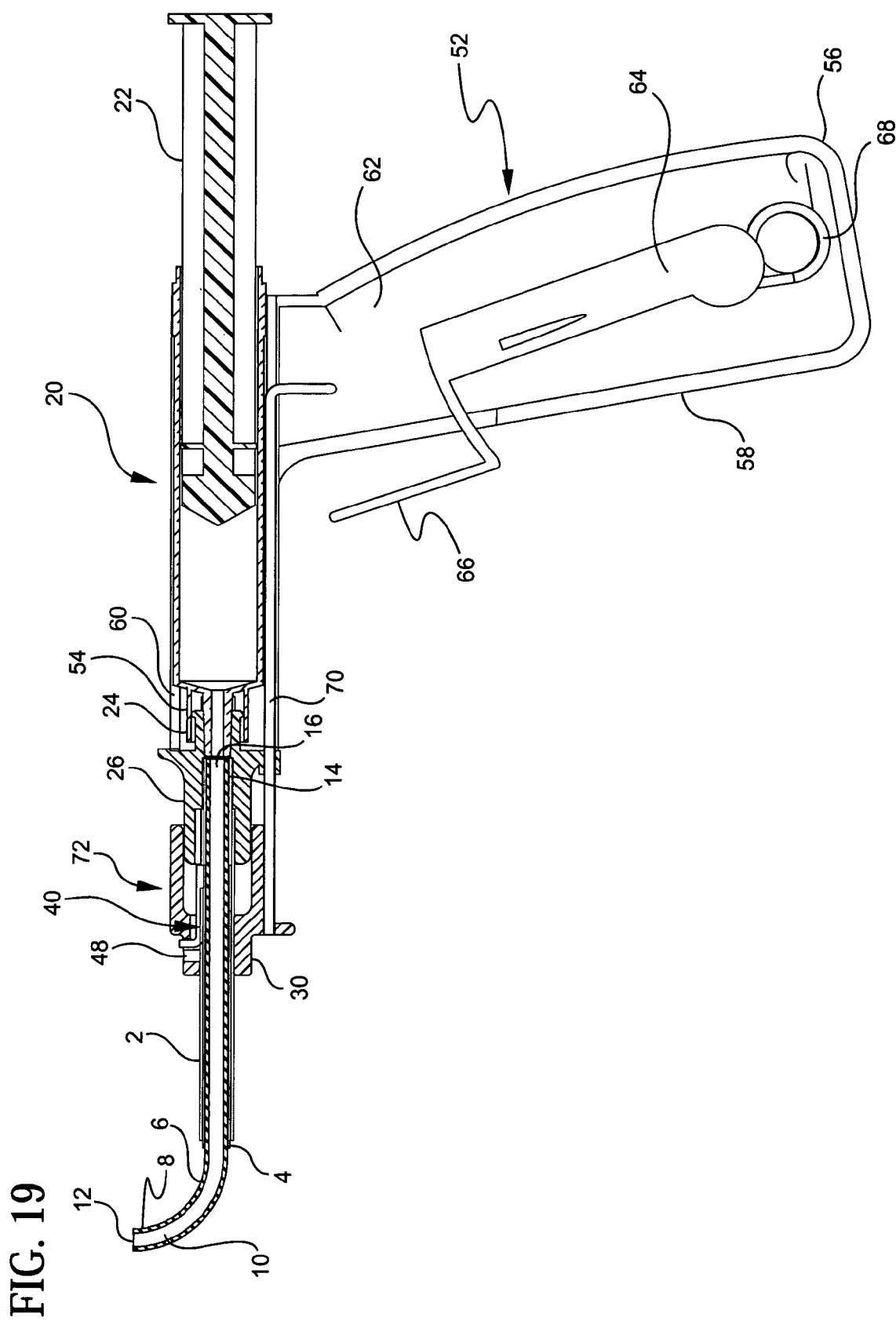
FIG. 19 is a longitudinal cross-sectional view of the laparoscopic medical fluid delivery device of the present invention shown in FIGS. 16-18.
Figure 20:
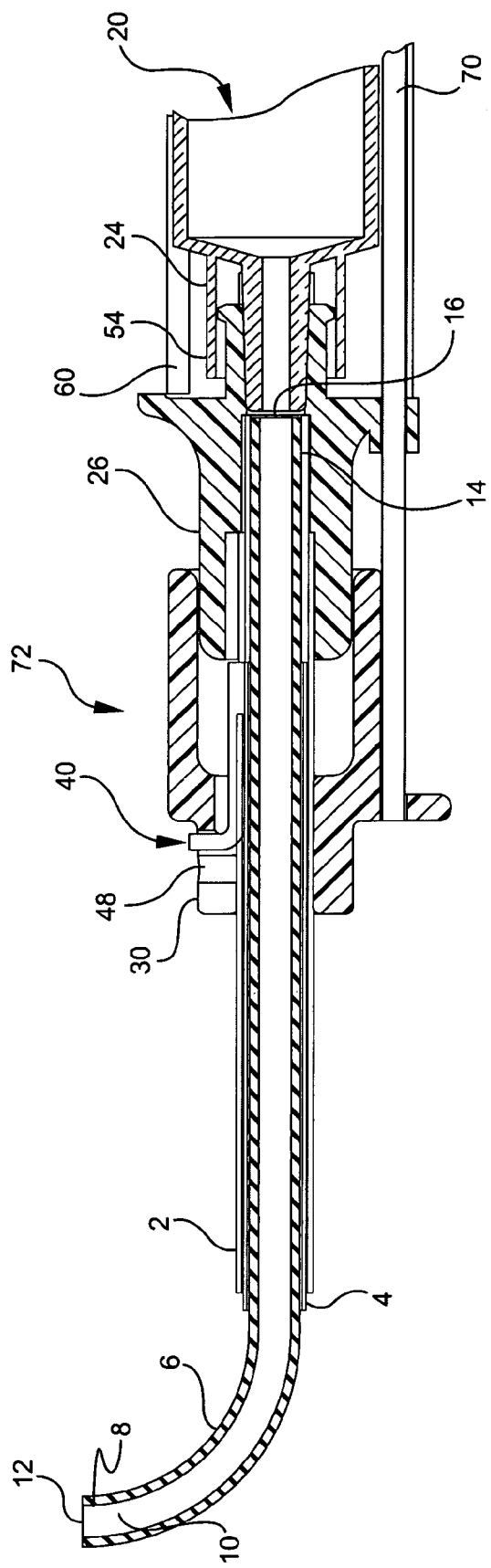
FIG. 20 is an enlarged, cross-sectional view of a portion of the laparoscopic medical fluid delivery device of the present invention shown in FIGS. 16-19.
Figure 21:
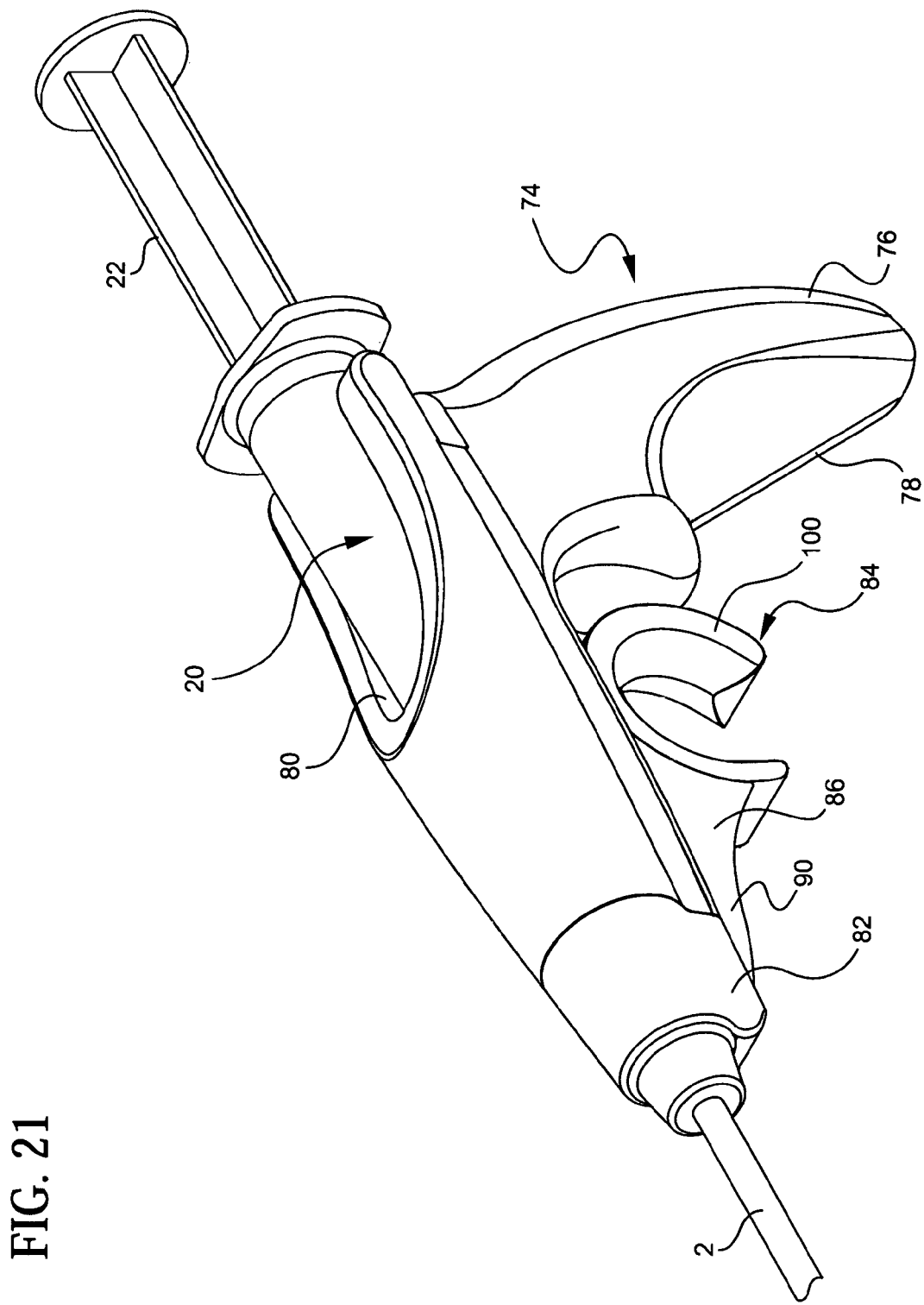
FIG. 21 is a front isometric view of a laparoscopic medical fluid delivery device constructed in accordance with a third embodiment of the present invention.
Figure 22:
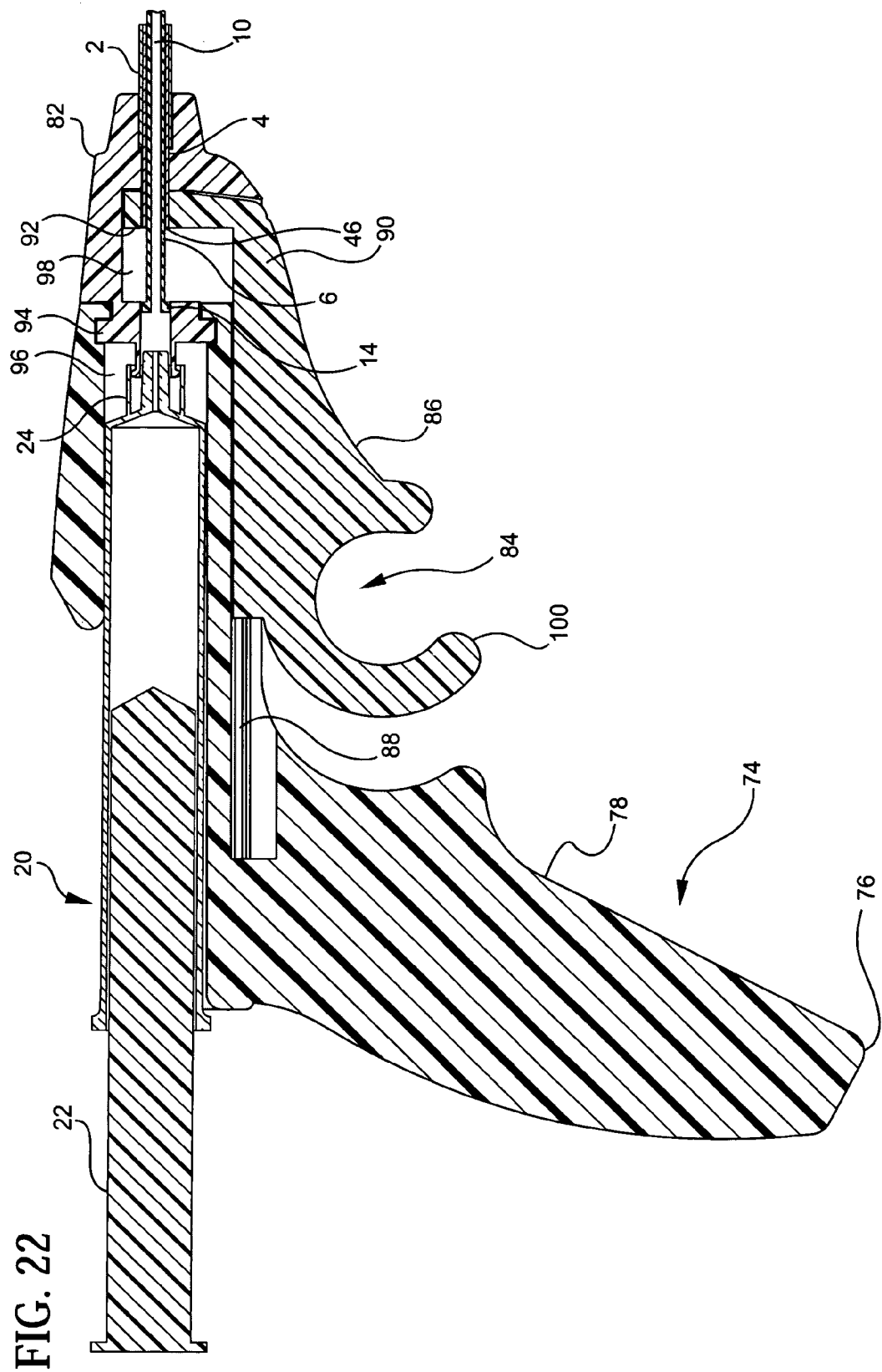
FIG. 22 is a longitudinal, cross-sectional view of the laparoscopic medical fluid delivery device of the present invention shown in FIG. 21, showing the trigger arm thereof in a first position.
Figure 23:
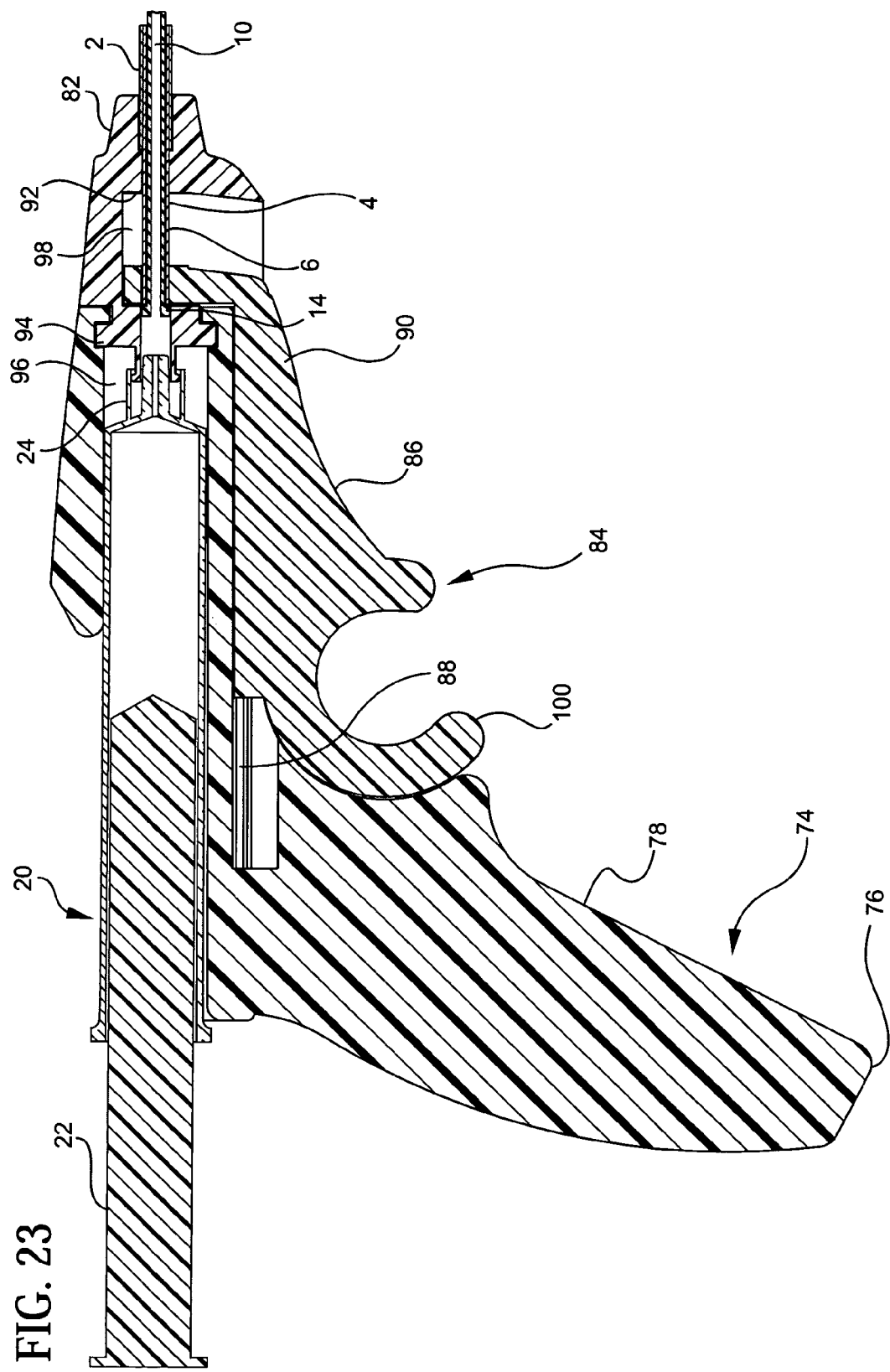
FIG. 23 is a longitudinal, cross-sectional view of the laparoscopic medical fluid delivery device of the present invention shown in FIG. 21, showing the trigger arm thereof in a second position.
Figure 24:
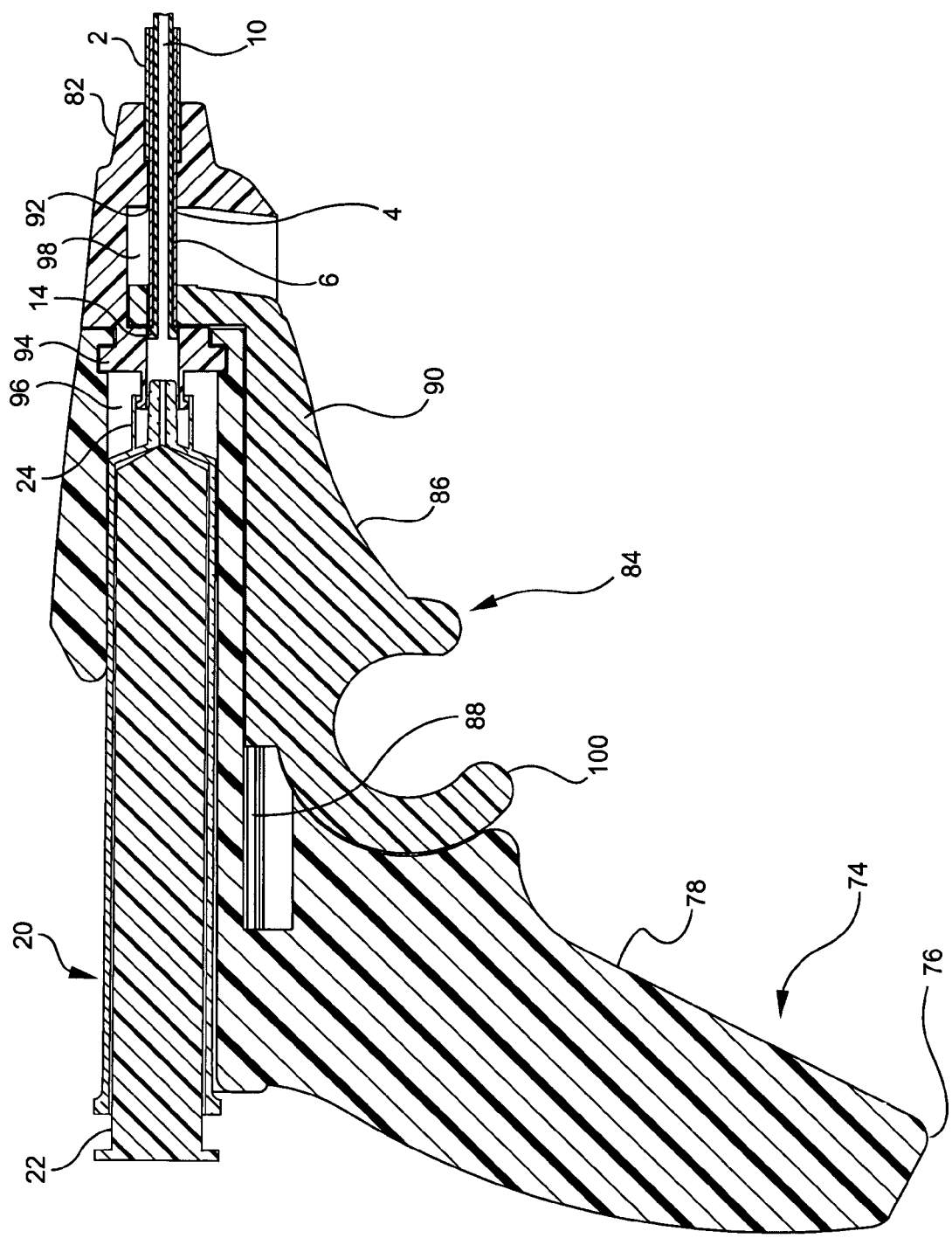
FIG. 24 is a longitudinal, cross-sectional view of the laparoscopic medical fluid delivery device of the present invention shown in FIG. 21, showing the trigger arm thereof in a second position, and further illustrating the plunger of a syringe filled with medical fluid pressed inwardly of the syringe to dispense fluid from the syringe to the laparoscopic medical fluid delivery device of the present invention.
Figure 25:
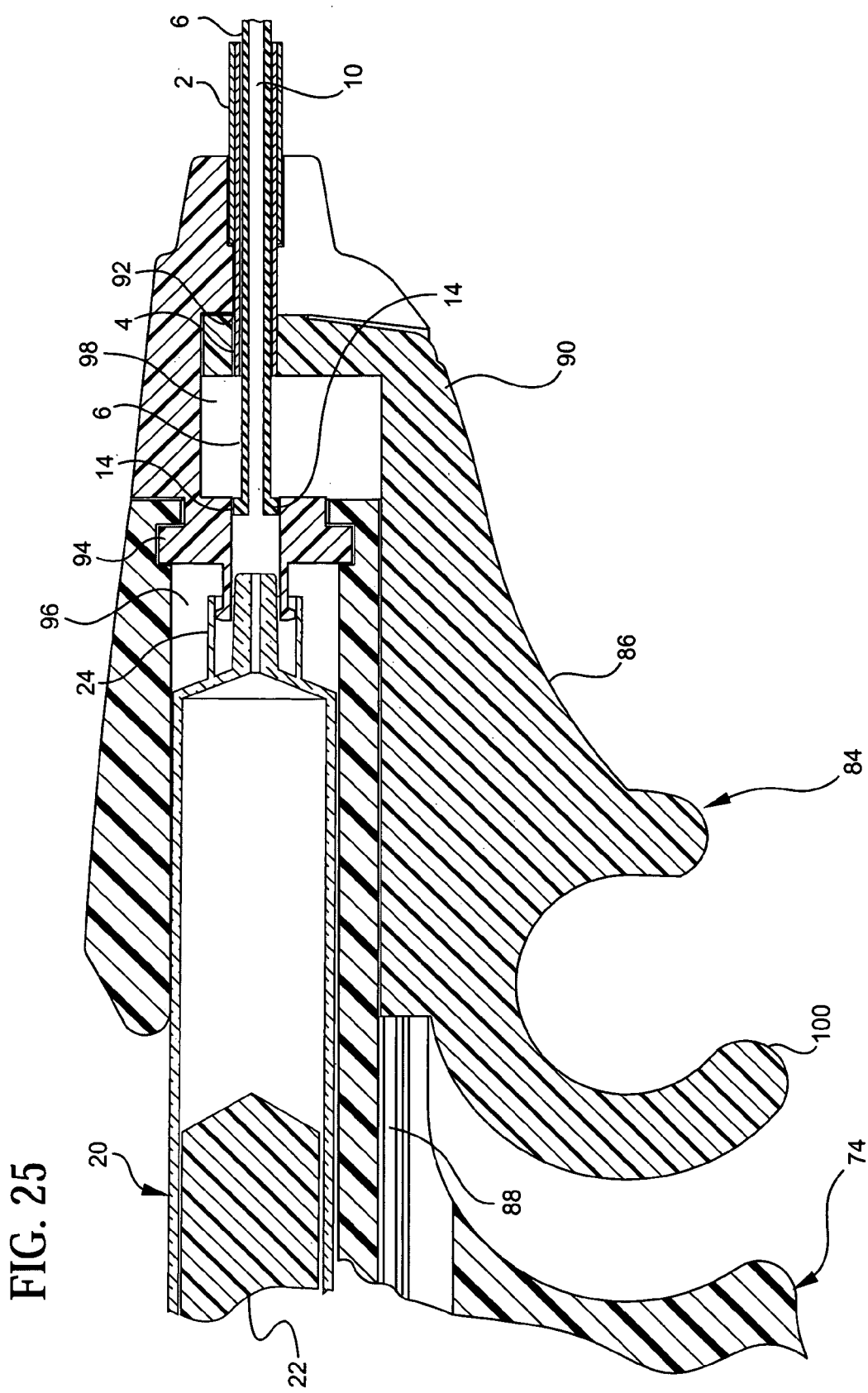
FIG. 25 is an enlarged, longitudinal cross-sectional view of a portion of the laparoscopic medical fluid delivery device of the present invention shown in FIGS. 21-24.
Figure 27:
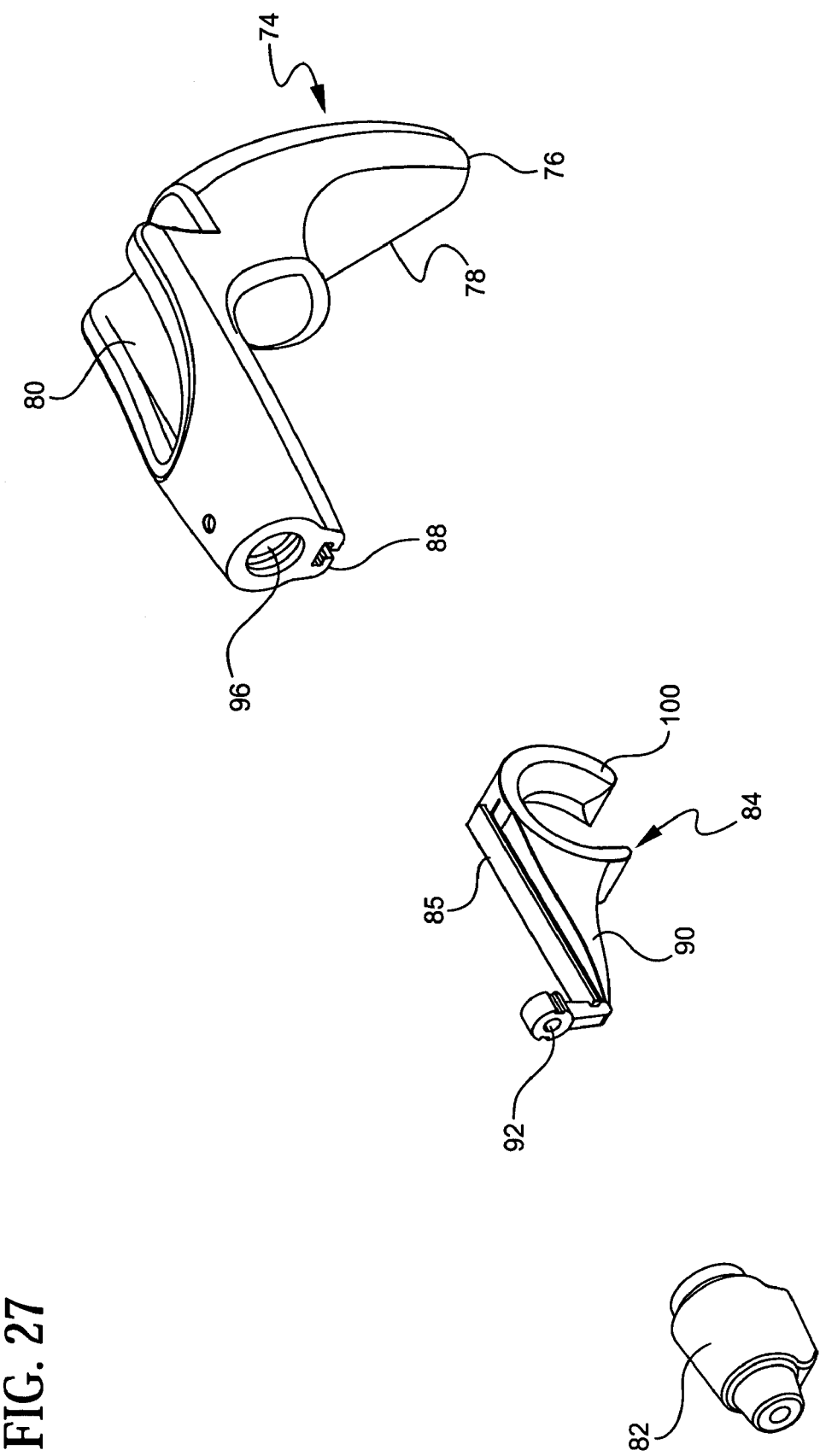
FIG. 27 is a partially exploded, isometric view of portions of the laparoscopic medical fluid delivery device of the present invention shown in FIGS. 21-26.
Figure 28:
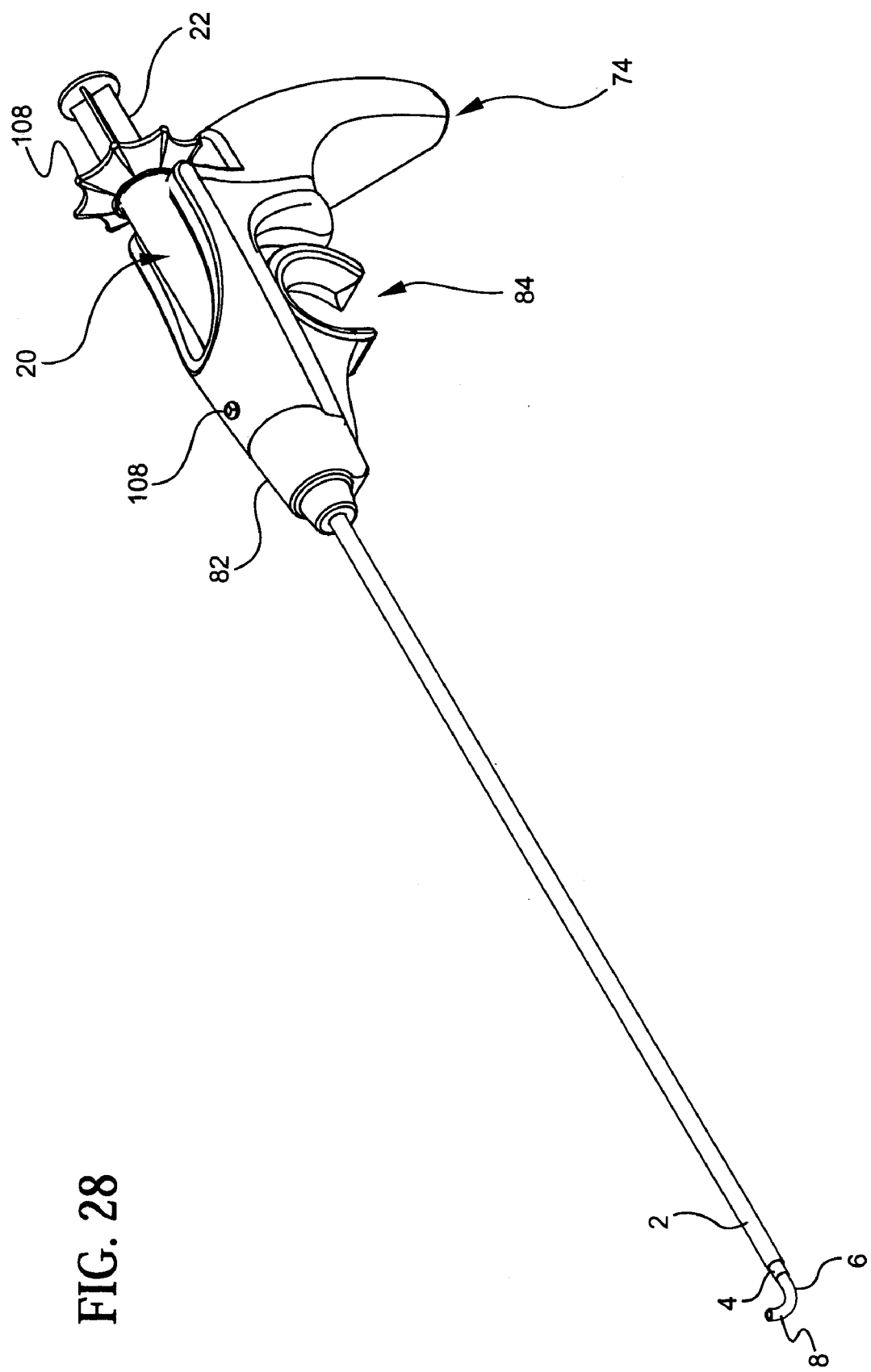
FIG. 28 is a front isometric view of a laparoscopic medical fluid delivery device constructed in accordance with an alternative version of the third embodiment of the present invention.
Figure 29:
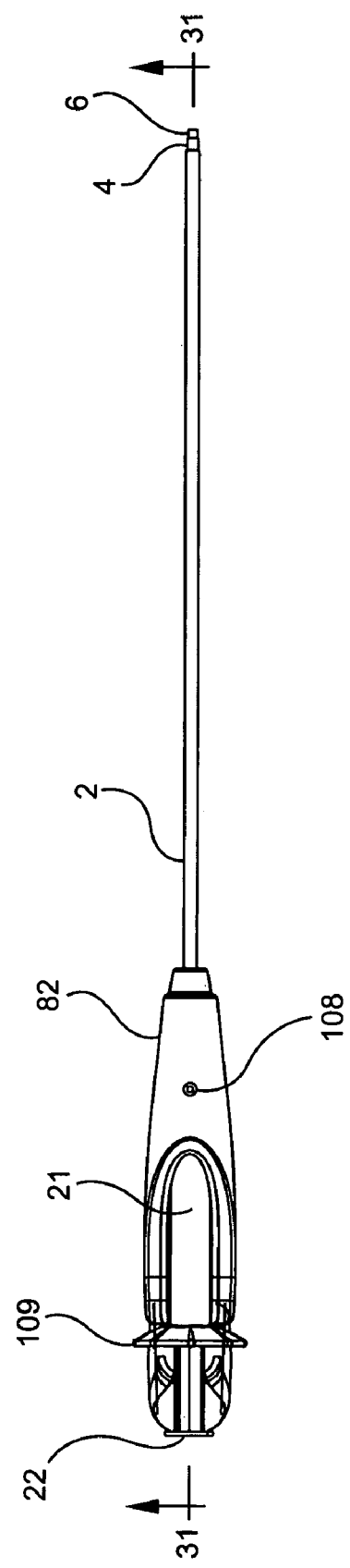
FIG. 29 is a top view of the laparoscopic medical fluid delivery device of the present invention shown in FIG. 28.
Figure 30:
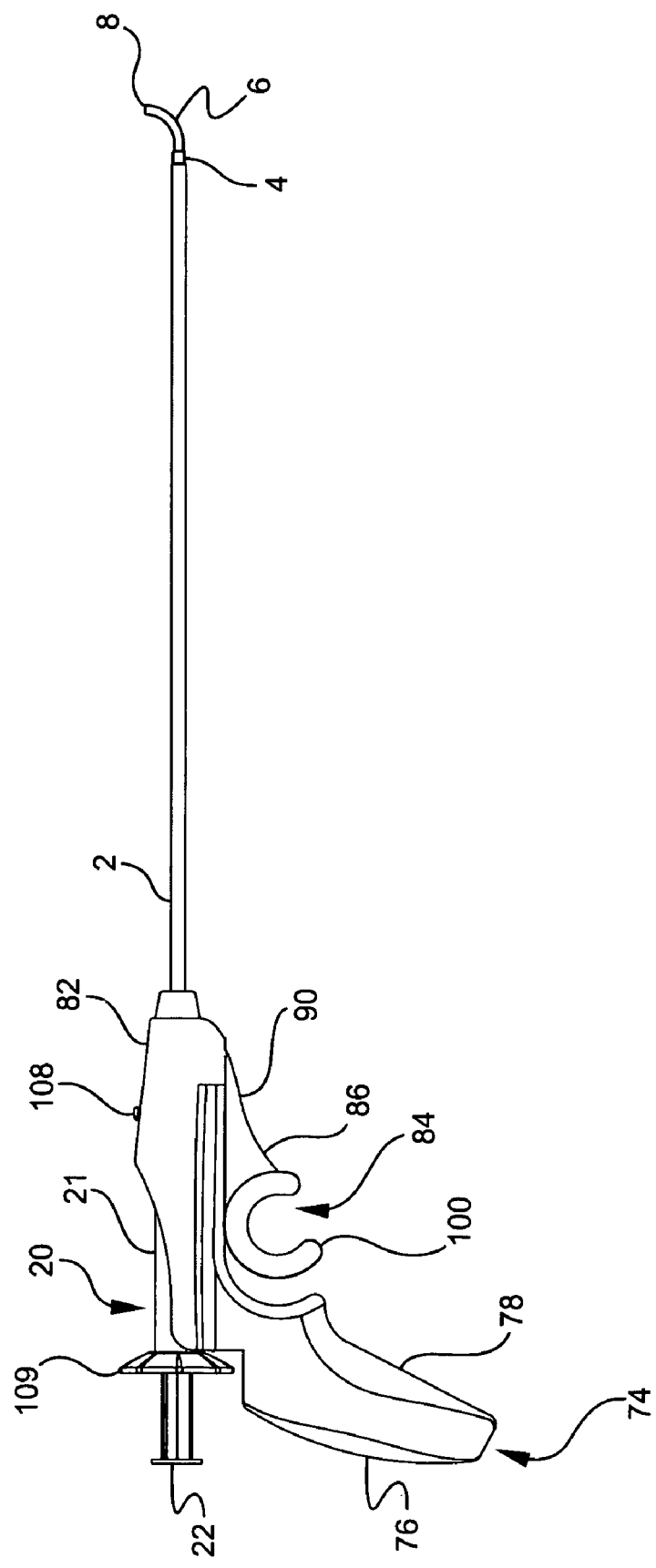
FIG. 30 is a side view of the laparoscopic medical fluid delivery device of the present invention shown in FIGS. 28 and 29.
Figure 31:
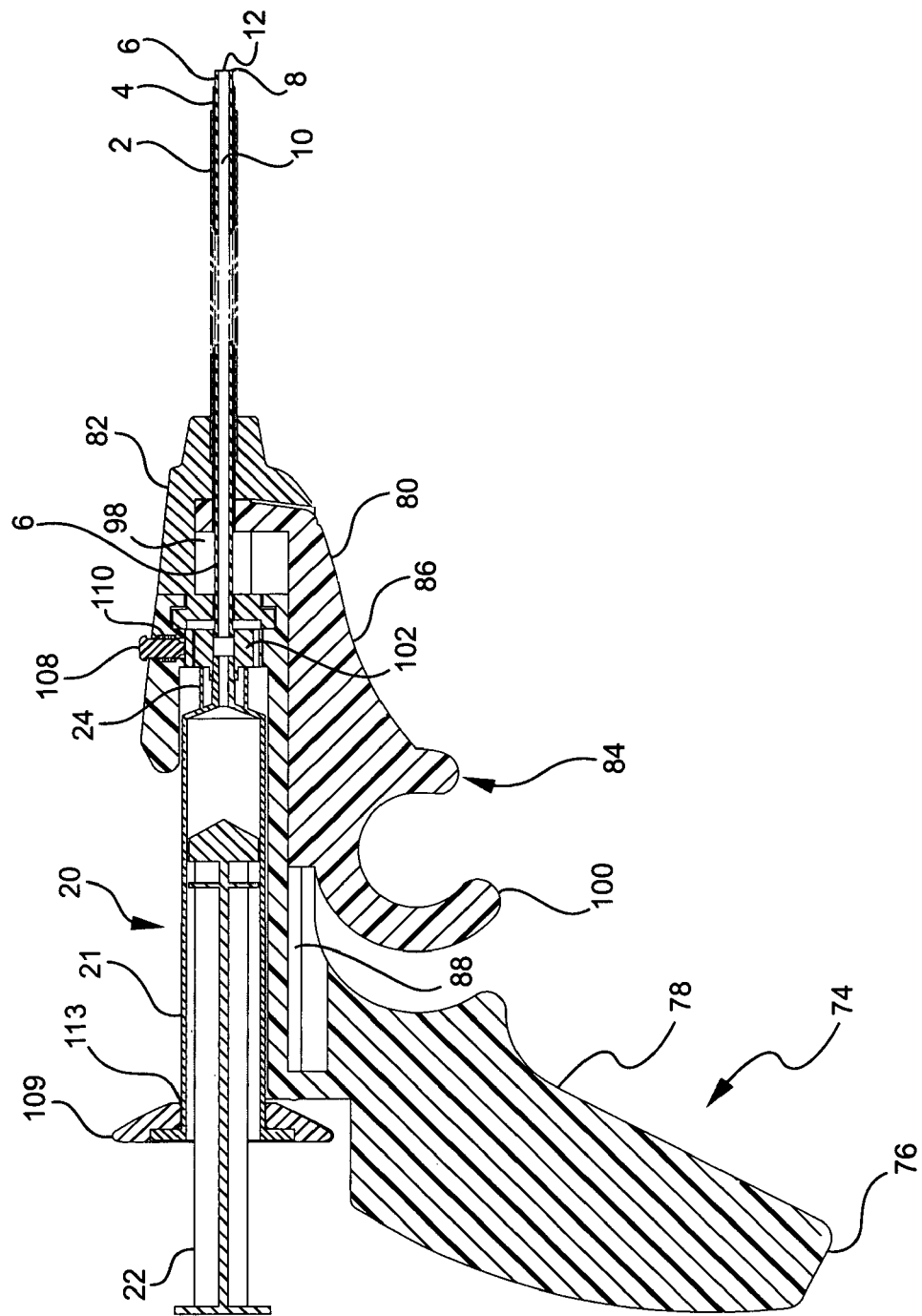
FIG. 31 is a longitudinal cross-sectional view of the laparoscopic medical fluid delivery device of the present invention shown in FIGS. 28-30.
Figure 32:
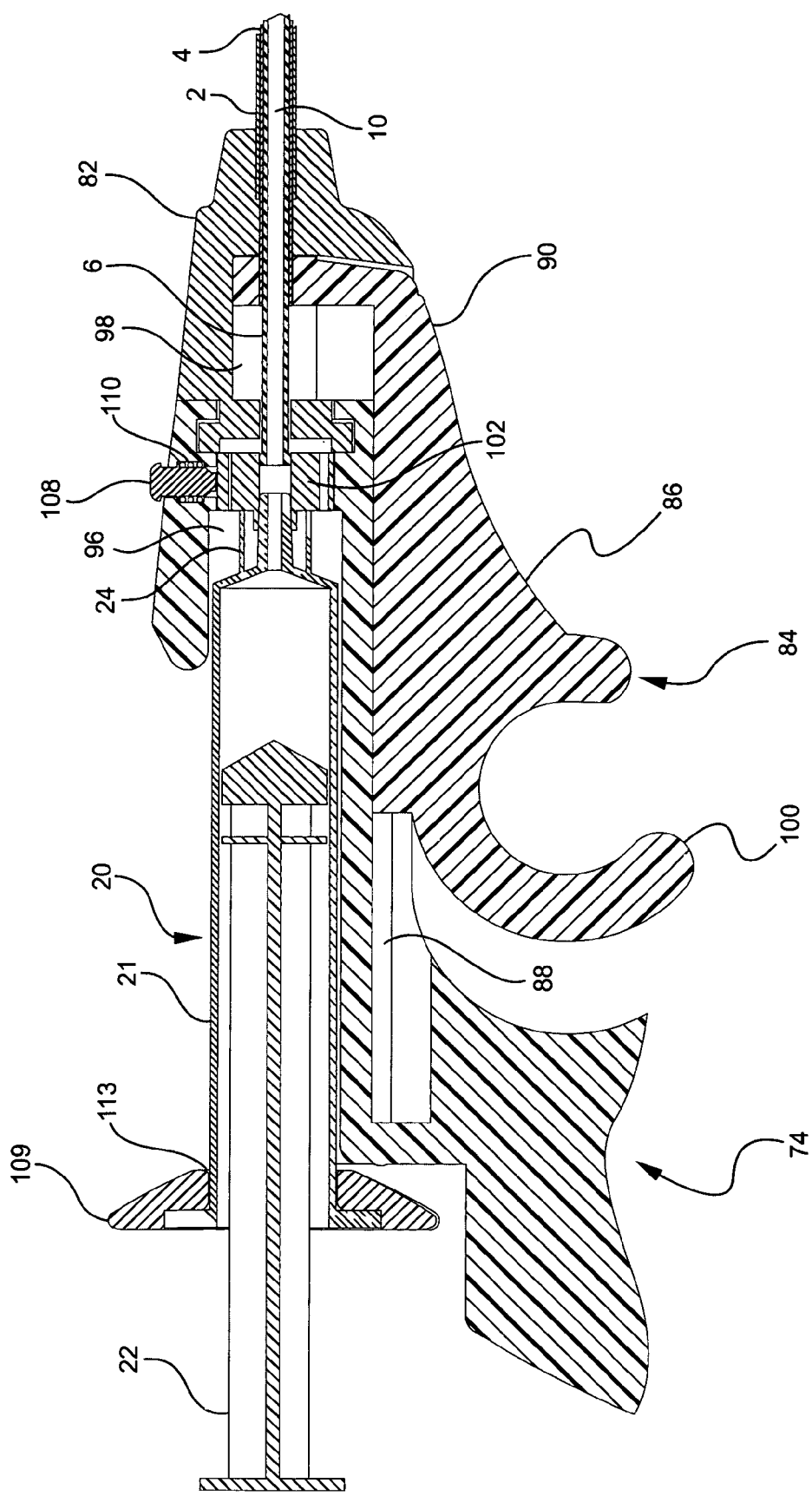
FIG. 32 is an enlarged, longitudinal cross-sectional view of the laparoscopic medical fluid delivery device of the present invention shown in FIGS. 28-31.
Figure 33:
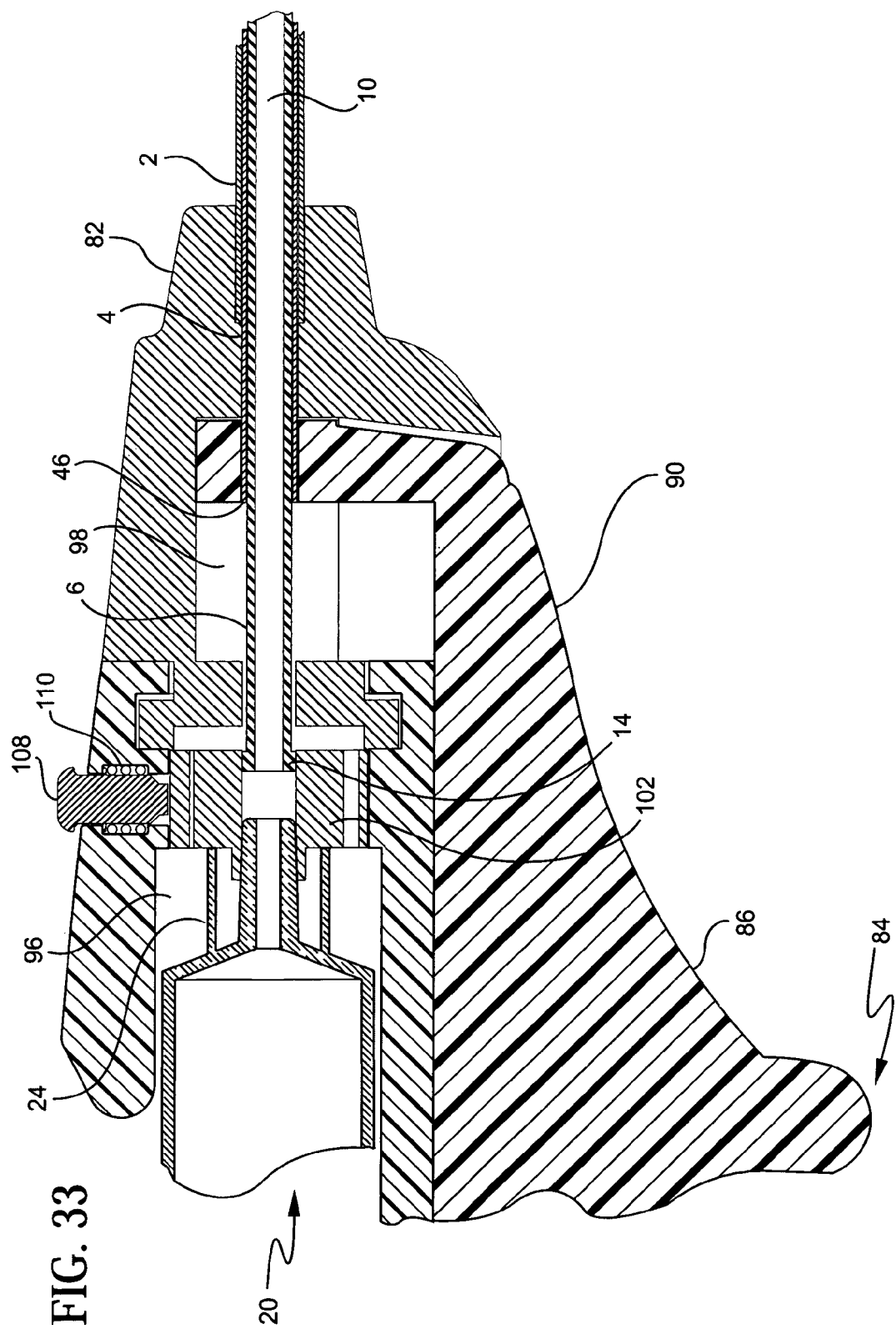
FIG. 33 is an enlarged, longitudinal cross-sectional view of a portion of the laparoscopic medical fluid delivery device of the present invention shown in FIGS. 28-32.
Figure 34:
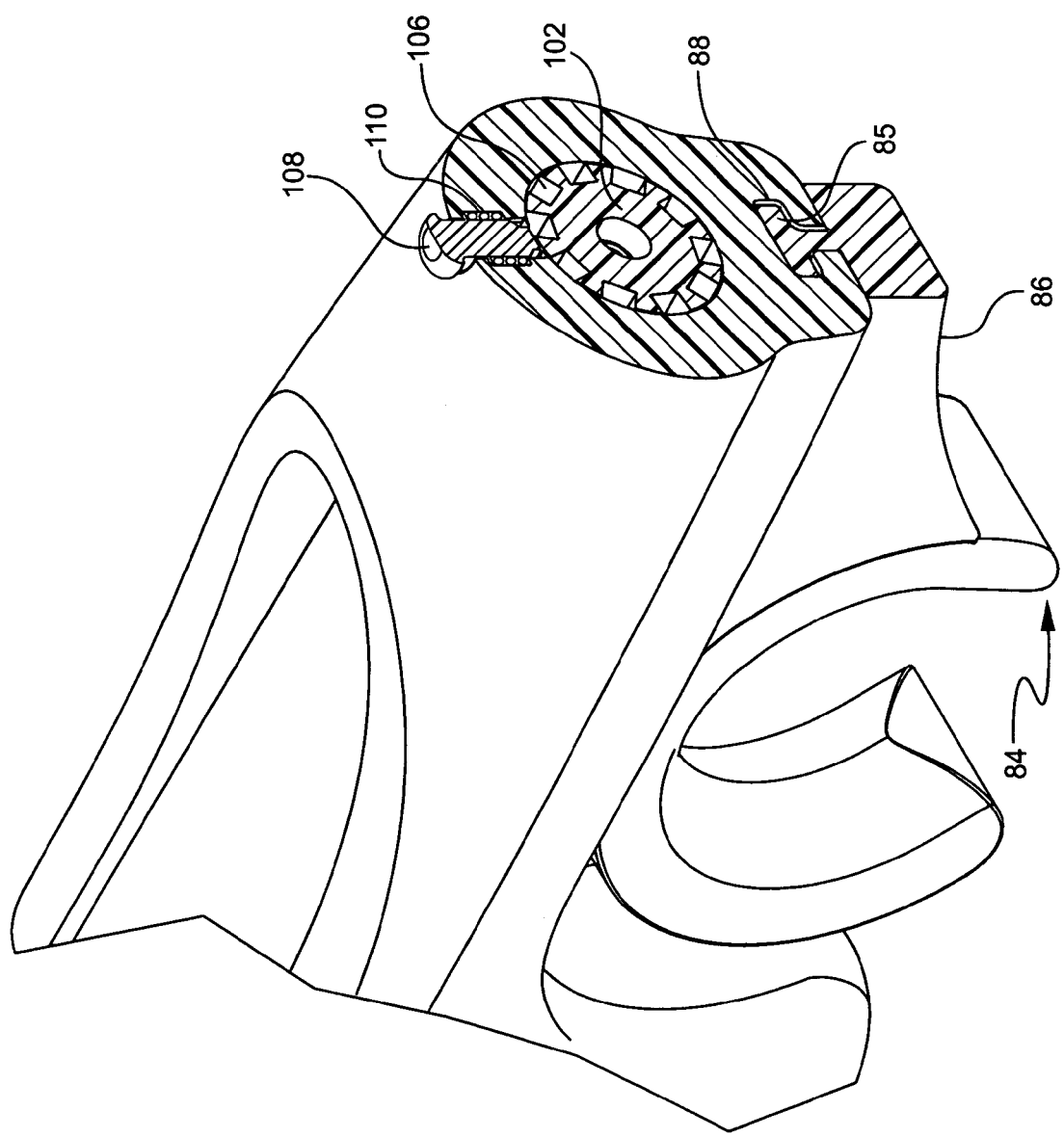
FIG. 34 is an isometric view of a portion of the laparoscopic medical fluid delivery device of the present invention shown in FIGS. 28-33, with a portion thereof cut away.
Figure 35:
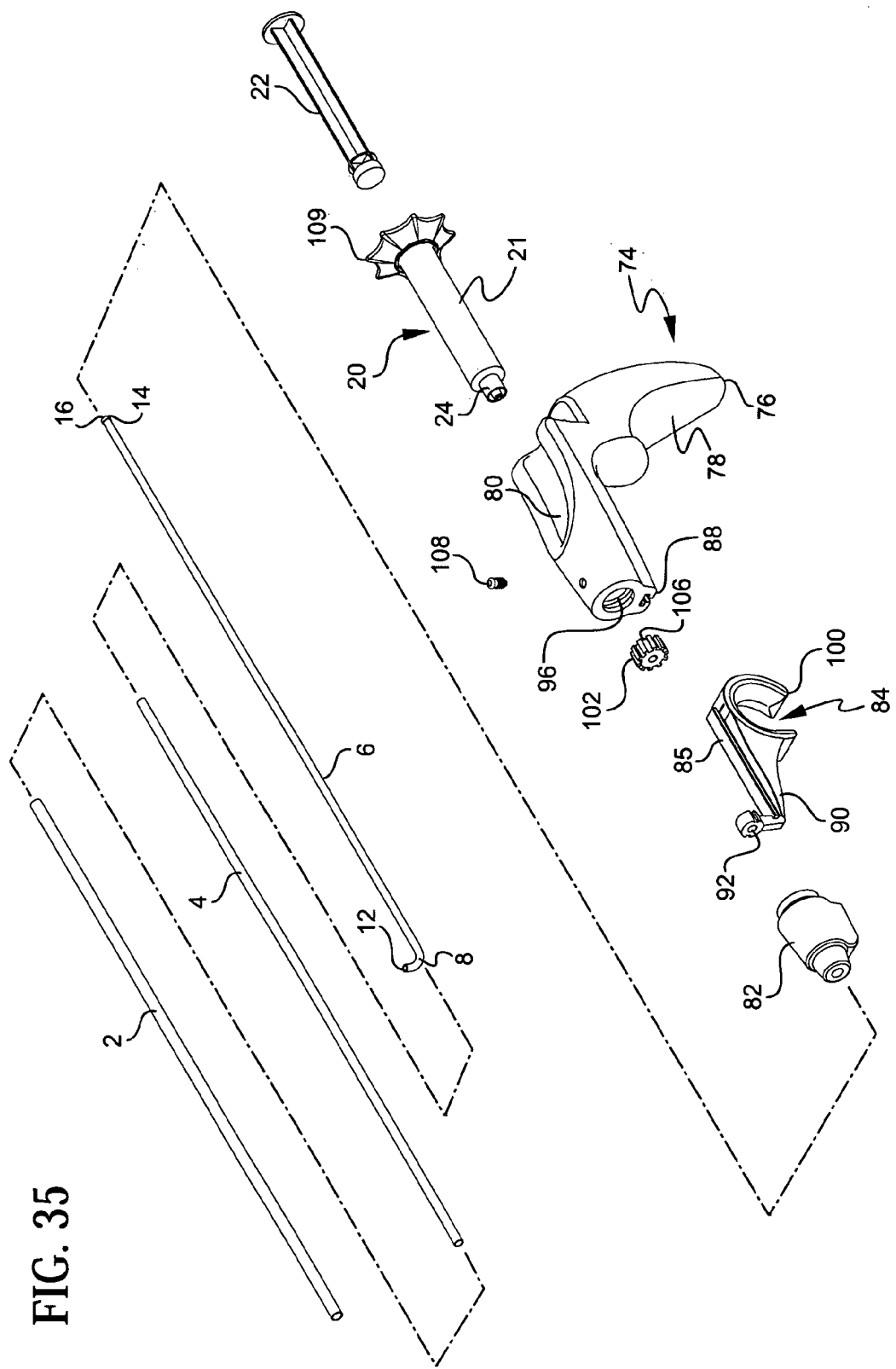
FIG. 35 is an exploded isometric view of the laparoscopic medical fluid delivery device of the present invention shown in FIGS. 28-34.
Figure 36:
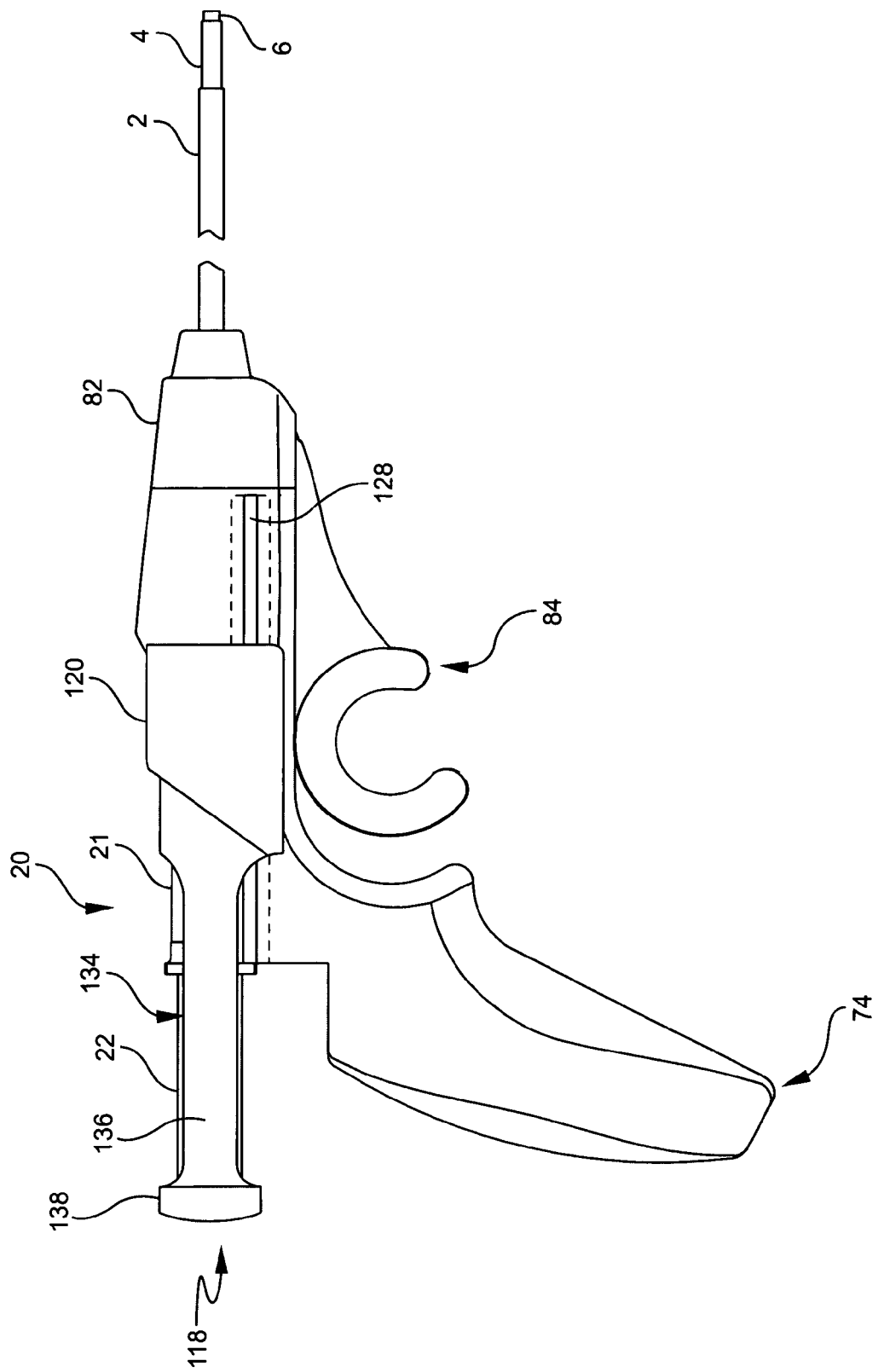
FIG. 36 is a side view of a laparoscopic medical fluid delivery device constructed in accordance with a further variation of the third embodiment of the present invention, and illustrating the trigger arm thereof in a first position.
Figure 37:
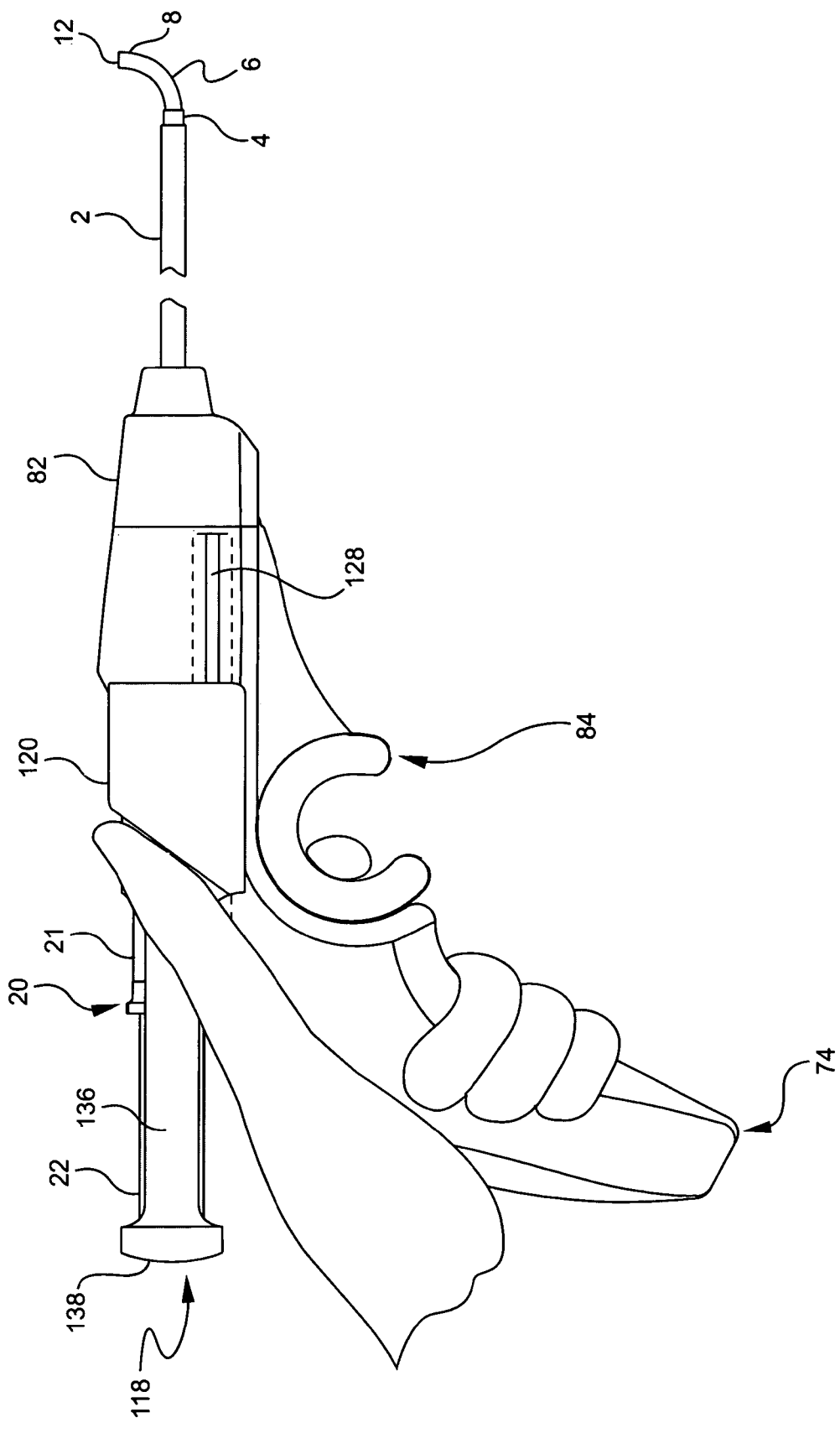
FIG. 37 is a side view of the laparoscopic medical fluid delivery device of the present invention shown in FIG. 36, and illustrating the trigger arm thereof in a second position to cause the distal end tip portion of the catheter to articulate.
Figure 38:
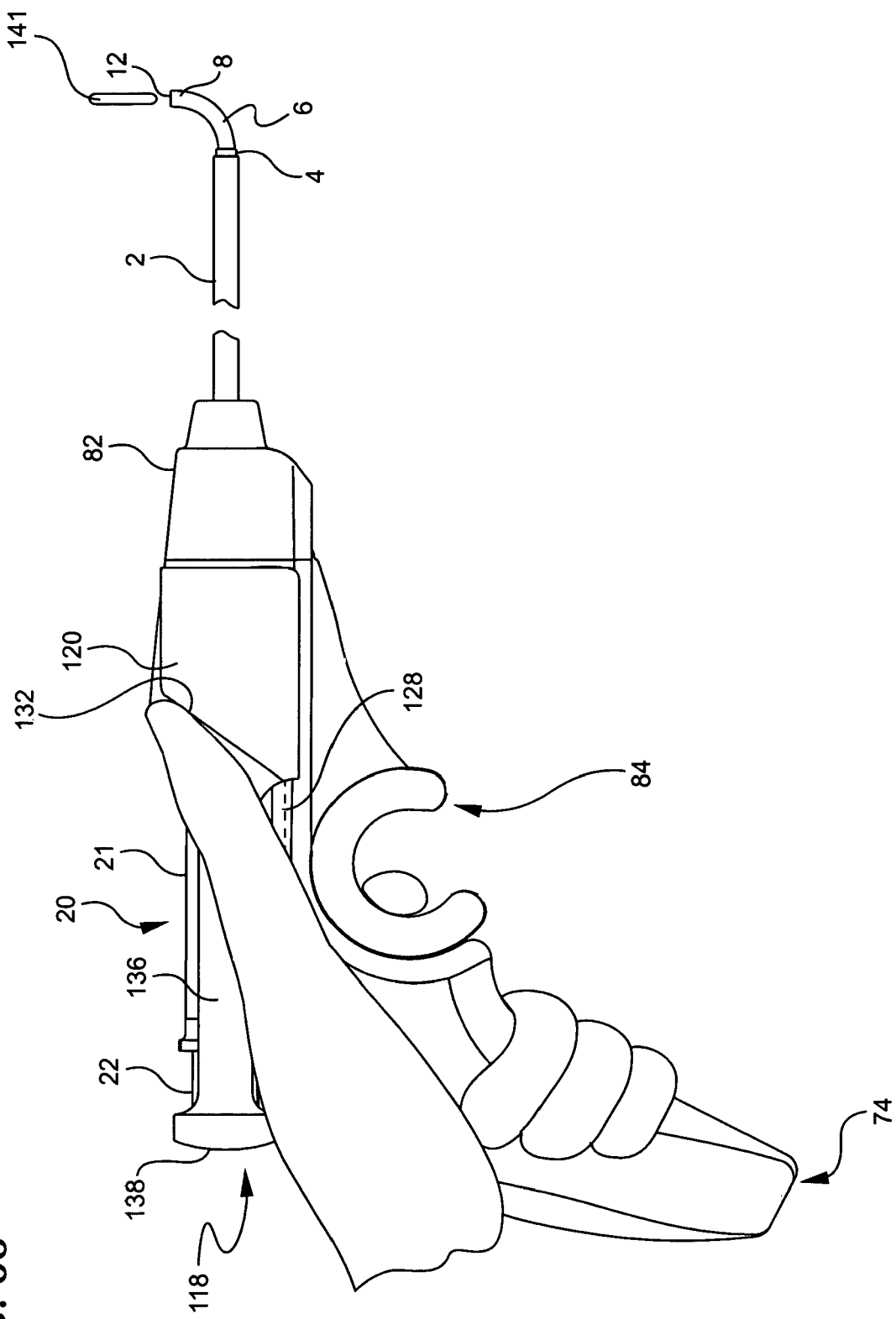
FIG. 38 is a side view of the laparoscopic medical fluid delivery device of the present invention shown in FIGS. 36 and 37, and illustrating the plunger of the syringe received thereby being forced to expel fluid from the articulated tip of the medical fluid delivery device.

As shown in FIGS. 14-15 a pressure release fluid seal 21, such as a one-way, "duck bill" valve, may be secured (for example, by an adhesive) to or integrally formed with the distal end of the catheter 6 so that the fluid seal 21 is in communication with the lumen 10 thereof to selectively prevent the flow of medical fluid through the catheter lumen 10 and to allow medical fluid to flow therethrough upon a predetermined pressure being exerted on the medical fluid by the syringe plunger. The fluid seal 21 is provided to assure that no medical fluid contained in the syringe 20 or the catheter lumen 10 is unintentionally dispensed, especially if low viscosity fluids are used. Alternatively, the releaseable fluid seal 21 may be incorporated within the catheter lumen or lumens 10.

Return now to FIGS. 7-9, it will be seen that the proximal end 14 of the catheter 6, and the opening 16 formed at the axial end thereof, are in fluid communication with a syringe 20 having a bore for receiving and containing a medical fluid, and a plunger 22 received by the bore of the syringe 20 for dispensing the medical fluid contained therein. Preferably, the syringe 20 includes a standard luer lock connector or fitting 24, and the catheter 6 of the laparoscopic fluid delivery device of the present invention includes a cooperating and mating luer lock connector or fitting 26 engageable with the syringe 20 at its connector or fitting 24. When the syringe connector 24 and the connector 26 of the laparoscopic fluid delivery device catheter 6 are joined, the lumen 10 and opening 16 in the proximal end of the catheter are preferably co-axially situated with respect to the syringe tip opening that leads to and communicates with the syringe bore to effect the transfer of medical fluid from the syringe bore to the lumen 10 of the catheter 6.

In the embodiment of the laparoscopic fluid delivery device of the present invention, the moveable inner tubular member 4 is operatively linked to an actuator that includes a lap collar 28 which is grasped by the surgeon and which is used by the surgeon to move the inner tubular member 4 axially within the outer tubular member 2 to cover and uncover the articulating distal end tip portion 8 of the catheter 6. More specifically, the lap collar 28 is preferably formed as a unitary, generally cylindrical body 30 having a first flange 32 radially extending from the cylindrical body 30 and a second flange 34 radially extending from the cylindrical body 30 which is spaced apart axially from the first flange 32 to define a finger slot 36 therebetween. The surgeon places two fingers (preferably his or her index and middle finger) to straddle the finger slot 36 to maneuver the inner tubular member 4 with respect to the outer tubular member 2 and the catheter 6 by retracting the inner tubular member 4 towards the proximal end 14 of the catheter or pushing the inner tubular member towards the distal end of the catheter 6 to respectively uncover or cover a selectable axial length of the catheter tip portion 8, in order to vary the curvature of the articulating tip portion to that which is desired. The surgeon then removes his or her fingers from the finger slot 36 so as not to inadvertently change the selected curvature of the articulating tip 8, and may then place his or her fingers on the neck of the syringe 20. Then, the surgeon uses his or her thumb to depress the plunger 22 within the syringe 20 to force medical fluid contained therein through the proximal end opening 16, lumen 10 and distal tip opening 12 of the catheter 6 to precisely direct the medical fluid through the laparoscopic fluid delivery device to a targeted tissue site. This embodiment of the laparoscopic fluid delivery device is structured to permit one-handed operation by the physician in selecting the degree of articulation of the catheter tip 8 and the delivery of fluids to the targeted site.

In the embodiment of the laparoscopic fluid delivery device shown in FIGS. 1-15 of the drawings, the lap collar 28 is operatively linked to the moveable inner tubular member 4 in the manner described below, although it is envisioned to be within the scope of the present invention to have other structures which link the lap collar 28 or other actuating device with the moveable inner tubular member 4. The outer tubular member 2 includes a slot 38 formed in its sidewall running axially along a portion of the length thereof. An L-shaped wire, bracket, rod or other linkage 40 having a first leg 42 and a second leg 44 joined to the first leg 42 and bent ninety degrees (90°) with respect to the first leg 42 has its first leg (which is shown in the drawings as being longer than the second leg 44) affixed by welding or the like to the outer surface of the inner tubular member 4 axially along a portion of the proximal end 46 of the inner tubular member such that the wire protrusion 40 is received by and reciprocatingly slides within the slot 38 formed in the outer tubular member 2. The slot 38 in the outer tubular member has a length which is dimensioned to allow full movement of the wire protrusion 40 therein to effect the required covering and uncovering of the articulating distal tip 8 of the catheter when the lap collar 28 is moved by the surgeon. The shorter, second leg 44 of the wire protrusion 40 passes through a radially disposed opening 48 formed in the lap collar body 30, which second leg 44 is held in place by a set screw 50 also received by the radial opening 48. Alternatively, the wire protrusion 40 may be omitted, and the set screw 50 may directly engage the outer surface of the inner tubular member 4 through the slot 38 formed in the outer tubular member 2 to link the lap collar 28 to the inner tubular member 4.

In a second embodiment of the present invention, the articulating laparoscopic medical fluid delivery device of the present invention may include an actuator constituted as a handle with a trigger operatively linked to the inner tubular member 4 to move the inner tubular member with respect to the flexible catheter 6 and the outer tubular member 2. As shown in FIGS. 16-20 of the drawings, with this particular embodiment, the laparoscopic fluid delivery device generally includes a handle 52 for grasping by the surgeon, the top of which is formed with a barrel 54 for receiving and holding in place the syringe 20 containing the medical fluid to be delivered to the patient. More specifically, the handle 52 includes a housing 56 defining a handle portion 58 for grasping by the surgeon, and an upper portion 60 defining a barrel 54 for receiving therein the syringe 20. The barrel 54 is arranged on the handle 52 such that the syringe tip, with its luer lock fitting 24, is co-axially situated with the lumen 10 of the catheter 6 and its luer lock fitting 26 effect the passage of fluid from the syringe to the catheter. The handle housing 56 further defines an internal cavity 62. Within the cavity 62 defined by the handle housing is situated a trigger arm 64 in the form of an L-shaped member. One end of the trigger arm 64 is pivotally joined to the handle housing 56, and the opposite end of the trigger arm has an exposed finger portion 66 which extends through an opening formed in the handle housing 56 for engagement by a surgeon using his finger or fingers. A torsion spring 68 may be included within the housing cavity 62 to exert an opposing force on the trigger arm 64 to cause the inner tubular member 4 to cover the articulating tip 8 of the catheter 6 when the exposed finger portion 66 of the trigger arm is released by the surgeon. Alternatively, the torsion spring 68 may be attached to the trigger arm 64 to assist the physician in uncovering the articulating catheter tip 8. In such a case, the torsion spring 68 will help overcome any resistance in moving the inner tubular member 4 on the catheter 6, but does not provide so much force to the trigger arm 64 that the position of the inner tubular member 4 with respect to the catheter 6 is inadvertently changed from a desired position selected by the surgeon.

The trigger arm 64, near the end opposite from where it is pivotally mounted in the handle housing 56, is joined to one axial end of a rod 70 whose opposite other axial end is joined to a collar 72 which is operatively linked to the moveable inner tubular member 4 through a wire protrusion 40, such as described previously with respect to the embodiment shown in FIGS. 1-15. The collar 72 includes a bore through which at least is partially received the outer tubular member 2, with the collar 72 being axially moveable on the outer tubular member and affixed to the inner tubular member 4. The outer tubular member 2 may be slotted as described previously with the first embodiment shown in FIGS. 1-15 of the drawings, and the collar 72 may be joined to the inner tubular member 4 in the same manner as described previously, and as shown in FIGS. 1-15. Since the collar 72 in the second embodiment of the present invention is not grasped by the surgeon, there is no need for radially extending flanges 32, 34 or a finger slot 36 to be formed in the collar body.

With this second embodiment of the laparoscopic fluid delivery device of the present invention, the surgeon grasps the handle portion 58 with his hand, places his index finger (the second finger) on the exposed finger portion 66 of the trigger arm 64 to uncover the articulating tip 8 of the catheter and adjust the articulation thereof to any desired angle, and places his thumb on the plunger 22 of the syringe 20 located in the barrel 54 of the handle 52, exerting pressure on the plunger to force medical fluid from the syringe through the lumen 10 of the catheter 6 and out the distal tip opening 12 to precisely provide the medical fluid to the targeted tissue site. As with the previous embodiment of the present invention, the laparoscopic medical fluid delivery device shown in FIGS. 16-20 allows for single-handed operation in selecting the degree of articulation of the catheter tip 8 and delivery of fluids to the targeted tissue site.

A laparoscopic medical fluid delivery device constructed in accordance with a third embodiment of the present invention is shown in FIGS. 21-27. Again, this embodiment allows for single-handed operation in articulating the catheter tip 8 and delivery of medical fluids to a targeted site within a patient. This third embodiment, shown in FIGS. 21-27, includes an actuator comprising a handle 74 having a housing 76 that defines a lower handle portion 78 for grasping by the surgeon, an upper portion defining a barrel 80 for receiving a syringe 20 containing a medical fluid to be dispensed to a patient, and a nose piece 82 situated at the front of the handle 74 through which pass the proximal ends of the inner and outer tubular members 4, 2 and the catheter 6.

The handle 74 also includes a trigger arm 84 which moves in a linear fashion and is connected preferably directly (but may be connected indirectly) to the proximal end 46 of the inner tubular member 4 for moving the member axially with respect to the outer tubular member 2 and the catheter 6. More specifically, the trigger arm 84 includes a main body 86 which slides reciprocatingly within a slot 88 formed in the housing 76 of the handle 74, the trigger arm 84 preferably being held captive within the slot 88. For this purpose, the trigger arm 84 may include a rail 85 extending longitudinally along the top surface thereof, which is received by the slot 88 formed in the handle housing 76. The trigger arm 84 includes a forward portion 90 which extends longitudinally from the main body 86 thereof, which forward portion 90 has a bore 92 formed axially through the thickness thereof which closely receives the proximal end 46 of the moveable inner tubular member 4 and thus secures with adhesive, for example, the trigger arm 84 to the inner tubular member. The innermost catheter 6 passes through the bore 92 to a luer lock connector fitting 94 held in place within the handle housing cavity 96. The longitudinal front portion 90 of the trigger arm 84 moves within a cavity 98 defined by the nose piece 82 of the housing situated at the front of the handle 74. The outer tubular member 2 has its proximal end fixed to the nose piece 82 so that it cannot move in relation to the handle.

The rearward portion of the trigger arm 84 is formed with an open loop or C-shaped member 100 which acts as a finger piece so that the surgeon may rest his or her index finger thereon to effect movement of the inner tubular member 4 to cover and uncover the articulating distal end 8 of the catheter 6.

The proximal end 14 of the catheter is joined to a luer lock fitting or connector 94, which engages and cooperates with a mating luer lock fitting or connector 24 situated on the syringe 20 to effect a fluidtight seal between the catheter 6 and the syringe 20. Again, as in the previous embodiments described, the lumen 10 and proximal opening 16 of the catheter 6 are co-axially situated with the syringe tip opening to effect the passage of medical fluid from the syringe 20 through the proximal opening 16, lumen 10 and distal opening 12 of the catheter to the targeted tissue site.

An alternative version of the third embodiment of the laparoscopic medical fluid delivery device of the present invention is illustrated by FIGS. 28-35. Here, the device allows the articulating distal tip 8 of the catheter 6 to rotate three hundred, sixty degrees (360°) so that the surgeon can even more precisely direct medical fluid to the targeted tissue site within the patient. One form of the structure which allows the catheter tip 8 to rotate is illustrated by FIGS. 28-35 of the drawings and will be described below, although it is envisioned to be within the scope of the present invention to provide other structure that allows the catheter 6 and/or the articulating catheter tip 8 to rotate.

More specifically, the luer lock fitting or connector 102 which is mounted to the proximal end 14 of the catheter, or other syringe adaptor that mates with the syringe, is situated within the cavity 96 of the handle housing 76 and is free to rotate therein. The sidewall of the fitting or connector 102 includes one or more spaced apart openings 106 radially formed therein and arcuately spaced about the circumference of the fitting. A lock pin 108 is mounted on the housing of the handle 74 and is biased upwardly by a coil spring 110, leaf spring or other biasing means so that it is normally not received by one of the plurality of openings 106 formed in the fitting or connector 102. The syringe 20, which is connected by its luer lock fitting or connector 24 to the fitting or connector 102 situated on the proximal end of the catheter 6, is loosely received by the barrel 80 formed in the handle housing 76 so that it may rotate with its fitting 24, the fitting 102 on the catheter and the catheter 6 itself within the inner tubular member 4. Thus, preferably all four components, that is, the syringe 20, its fitting 24, the catheter fitting 102 and the catheter 6, can rotate in unison on the handle 74.

A starwheel 109, knurled knob or other structure that may be readily turned by the surgeon using his or her fingers is securely mounted on the syringe body 21, with the syringe body 21 being closely received by an opening 113 formed through the thickness of the starwheel 109. Alternatively, the syringe 20 may be formed with the starwheel 109 integrally joined to the syringe body 21. Thus the surgeon can easily turn the starwheel 109 which, in turn, will rotate the syringe 20, the fittings 102, 24 and the catheter 6 in order to direct the articulating catheter tip 8 to any desired position.

The lock pin 108 is normally disengaged from the catheter fitting 102. When the syringe 20 is inserted into the barrel 80 of the handle of the laparoscopic fluid delivery device, the lock pin 108 is depressed by the surgeon against the force of the coil spring 110 so that it engages one of the plurality of openings 106 formed in the fitting 102 at the proximal end of the catheter. This holds the catheter fitting 102 steady so that the syringe 20 may be inserted into the barrel 80 and connected to the catheter fitting. Pressure on the lock pin 108 is then released, and the coil spring 110 biases the lock pin upwardly and away from the circumference of the catheter fitting 102 so that the syringe 20, catheter fitting 102 and catheter 6, including the catheter tip 8, are free to rotate within the handle 74 and inner tubular member 4 of the device when the surgeon turns the starwheel 109.

In a modification to the starwheel embodiment described above, the catheter fitting 102 itself may extend at least partially out of a slot (not shown) formed in the handle housing 76 so that at least a portion of its circumference is exposed to the surgeon who can turn the fitting 102 to effect rotation of the articulating distal tip 8 of the catheter, without the need for including the starwheel 109.

With this third embodiment, and the alternative versions thereof, shown in FIGS. 28-35 of the drawings, the physician loads the syringe 20 into the barrel 80 of the handle 74, depresses the lock pin 108 on the nose piece 82 to keep the catheter fitting 102 from turning, and connects the syringe luer lock fitting 24 thereto. He then releases the lock pin 108 to allow the catheter 6 to be rotated to any desired position. The surgeon grasps the handle portion 78 with his middle, ring and baby finger (third, fourth and fifth fingers), places his index finger on the C-shaped loop member 100 of the trigger arm 84, axially slides the trigger arm on the handle housing 76 to move the inner tubular member 4 in order to cover and uncover the articulating catheter tip 8 to a desired degree of curvature, and adjusts the angular position of the catheter tip by rotating the starwheel 109 to which the syringe 20 is attached (or the exposed edge of the catheter fitting 102 in the alternative embodiment). With his thumb, the surgeon pushes on the plunger 22 of the syringe to force medical fluid contained therein through the proximal opening 16, lumen 10 and distal opening 12 of the catheter 6 in order to precisely deliver medical fluid to the targeted tissue site within the patient;

A further variation of the third embodiment of the laparoscopic fluid delivery device of the present invention is shown in FIGS. 36-40. In this variation, the handle 74 includes a plunger linkage 118 which engages the syringe plunger 22.

Figure 40:
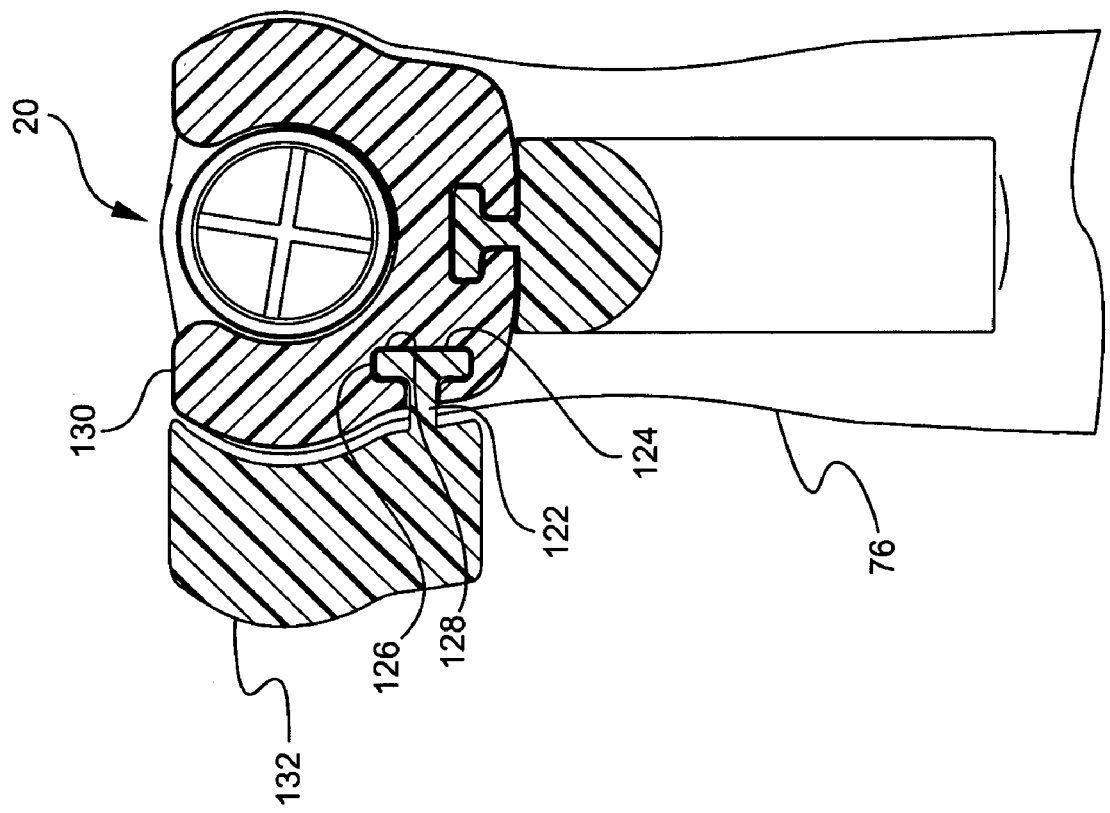
FIG. 40 is a cross-sectional view of the laparoscopic medical fluid delivery device of the present invention shown in FIGS. 36-39, taken along line 40-40 of FIG. 39.

More specifically, the plunger linkage 118 is an elongated member which is mounted to one side of the handle 74 of the laparoscopic fluid delivery device. It includes a main body 120 having an inner side surface which faces the outer surface of one side of the handle housing 76. A rail 122 extends outwardly from the inside surface of the main body 120 of the plunger linkage 118, which rail 122 includes either a bulbous or enlarged free end or a T-shaped free end 124, as shown in FIG. 40, with outwardly extending legs 126. The rail 122 is received in a cooperating slot 128 formed in a lateral sidewall 130 of the handle housing 76, which slot 128 extends substantially parallel to the axis of the second tubular member 2. The slot 128 allows the rail 122 to move reciprocatingly thereon axially along its length, with the enlarged free end or T-shaped end 124 situated within the body of the housing 76 so that the plunger linkage 118 is held captively against the sidewall 130 of the handle housing 76.

The plunger linkage 118 includes a thumb rest formed as a shoulder 132 extending outwardly from the opposite outside surface of the main body 120 thereof. The shoulder 132 may be sloped at an angle which is less than ninety degrees (90°) with respect to the axis of the outer tubular member 2 so that the surgeon may rest his or her hand thereon in a more comfortable position.

Figure 39:
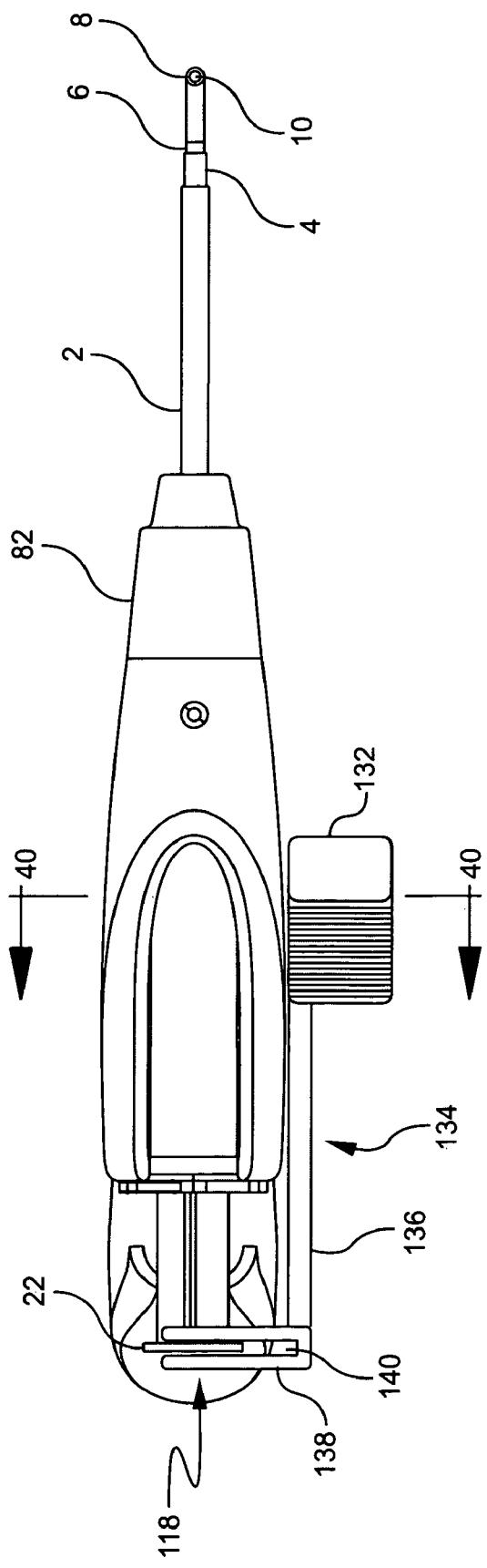
FIG. 39 is a top view of the laparoscopic medical fluid delivery device of the present invention shown in FIGS. 36-38.

An L-shaped member 134 extends axially rearwardly from the main body 120 of the plunger linkage 118. The L-shaped member 134 has a relatively long first leg portion 136 extending from the main body 120 of the plunger linkage, and a shorter second leg portion 138 attached to an end of the first leg portion 136 and extending transversely therefrom. The second leg portion 138 of the plunger linkage 118 engages and secures thereto the distal end of the plunger 22. For example, the second leg portion 138 of the plunger linkage may have a slot 140 formed therein to form an open pocket for receiving and captively holding the end of the plunger 22, as shown in FIG. 39 of the drawings. Other alternative structure for securing the plunger end to the linkage 118 is envisioned to be within the scope of the present invention.

As shown in FIGS. 36-40 of the drawings, the actuator, with its plunger linkage 118, of this third embodiment of the present invention allows the surgeon to move his thumb position more forward than in previous embodiments, rather than having his thumb rest on the plunger 22 of the syringe 20. This is a more natural hand position, and will allow the physician to more comfortably deliver medical fluids 141, such as sealants, adhesives or flowable haemostatic agents, to the surgical site. The surgeon presses on the thumb rest defined by the shoulder 132 on the plunger linkage 118 and pushes the linkage forward axially on the handle's side. This, in turn, causes the plunger 22, which is coupled to the second leg portion 138 of the plunger linkage 118, to axially move forward within the syringe 20, forcing medical fluid from the syringe into the lumen 10 and out the opening 12 in the articulating distal tip 8 of the catheter to the targeted tissue site. Again, this version of the laparoscopic medical fluid delivery device of the present invention allows for one-handed operation for both articulating the catheter tip 8 and for delivering medical fluid to the surgical site.

Figure 41:
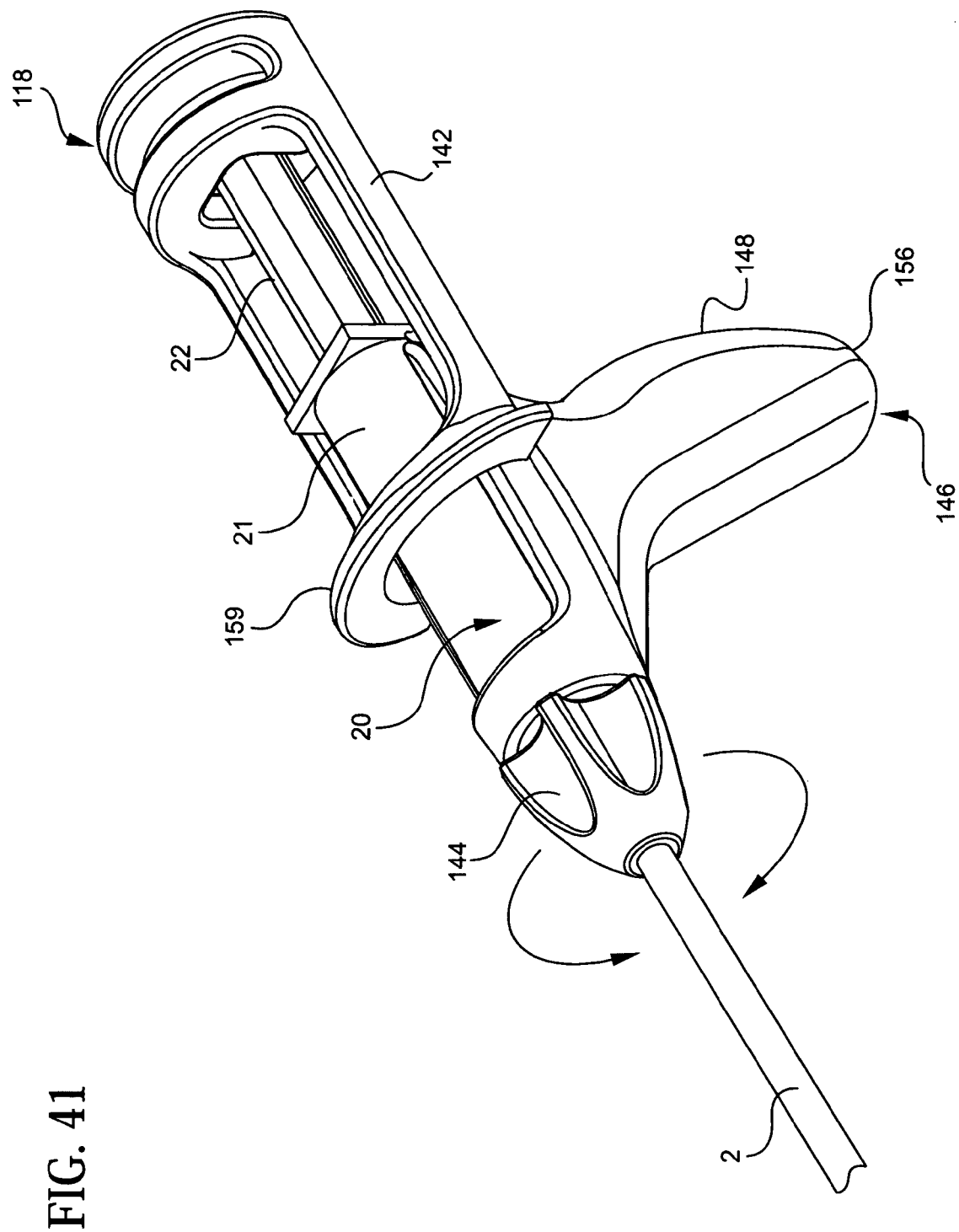
FIG. 41 is a front isometric view of a laparoscopic medical fluid delivery device constructed in accordance with a fourth embodiment of the present invention.
Figure 42:
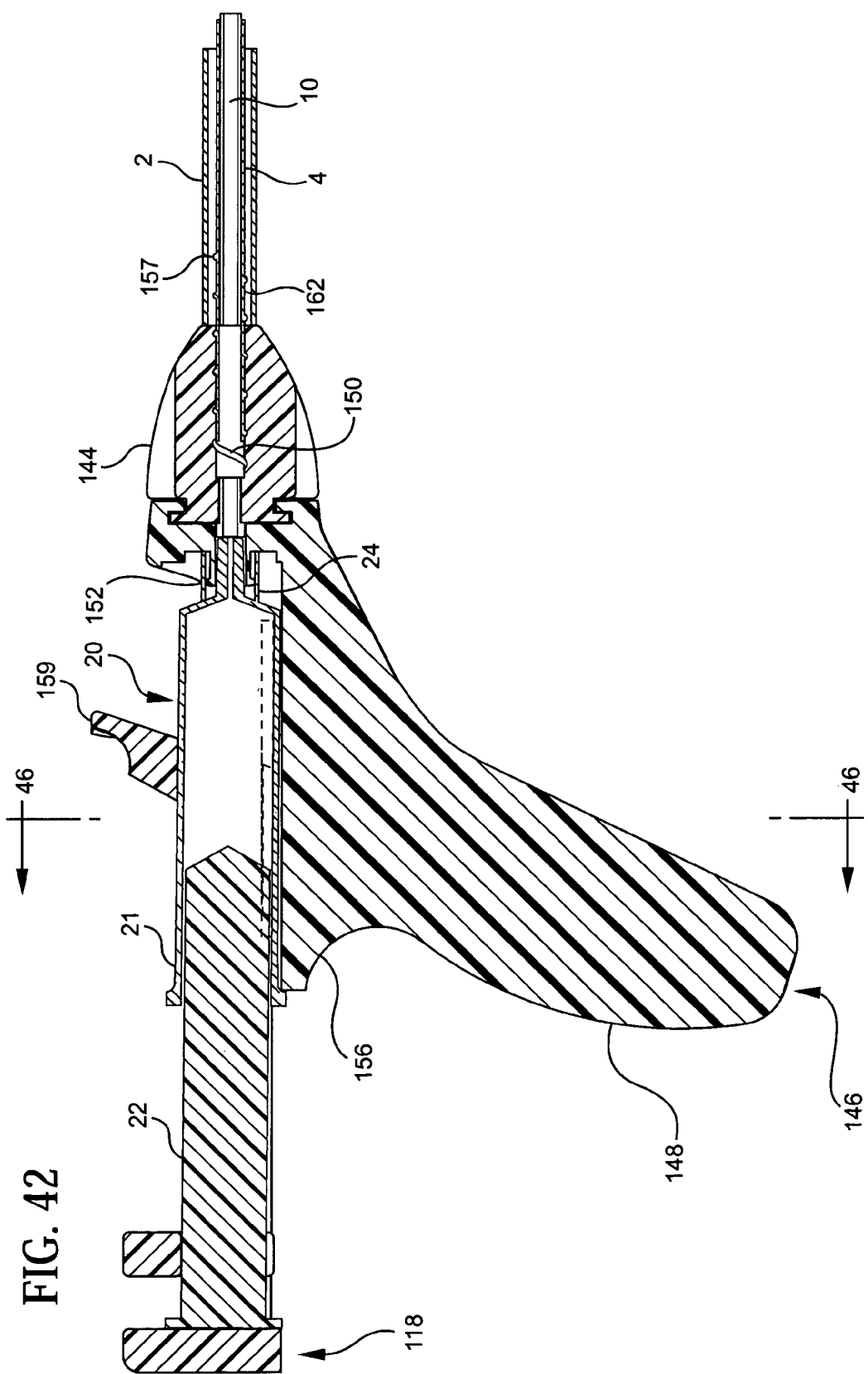
FIG. 42 is a longitudinal cross-sectional view of the laparoscopic medical fluid delivery device of the present invention shown in FIG. 41.
Figure 43:
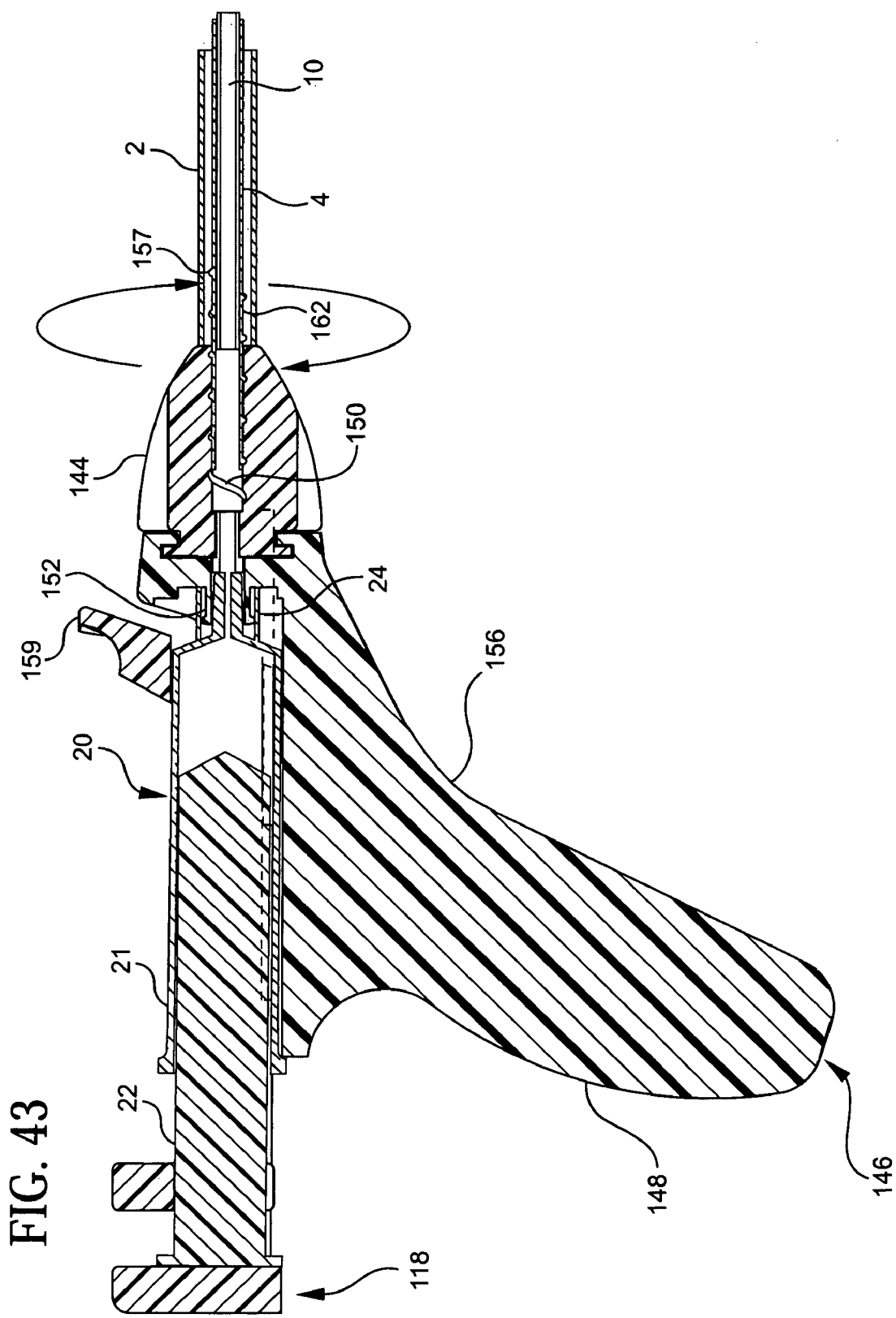
FIG. 43 is a longitudinal, cross-sectional view of the laparoscopic medical fluid delivery device shown in FIGS. 41 and 42, with the plunger of the syringe received by the device shown advanced in the syringe to expel fluid therefrom and through the medical fluid delivery device.
Figure 44:
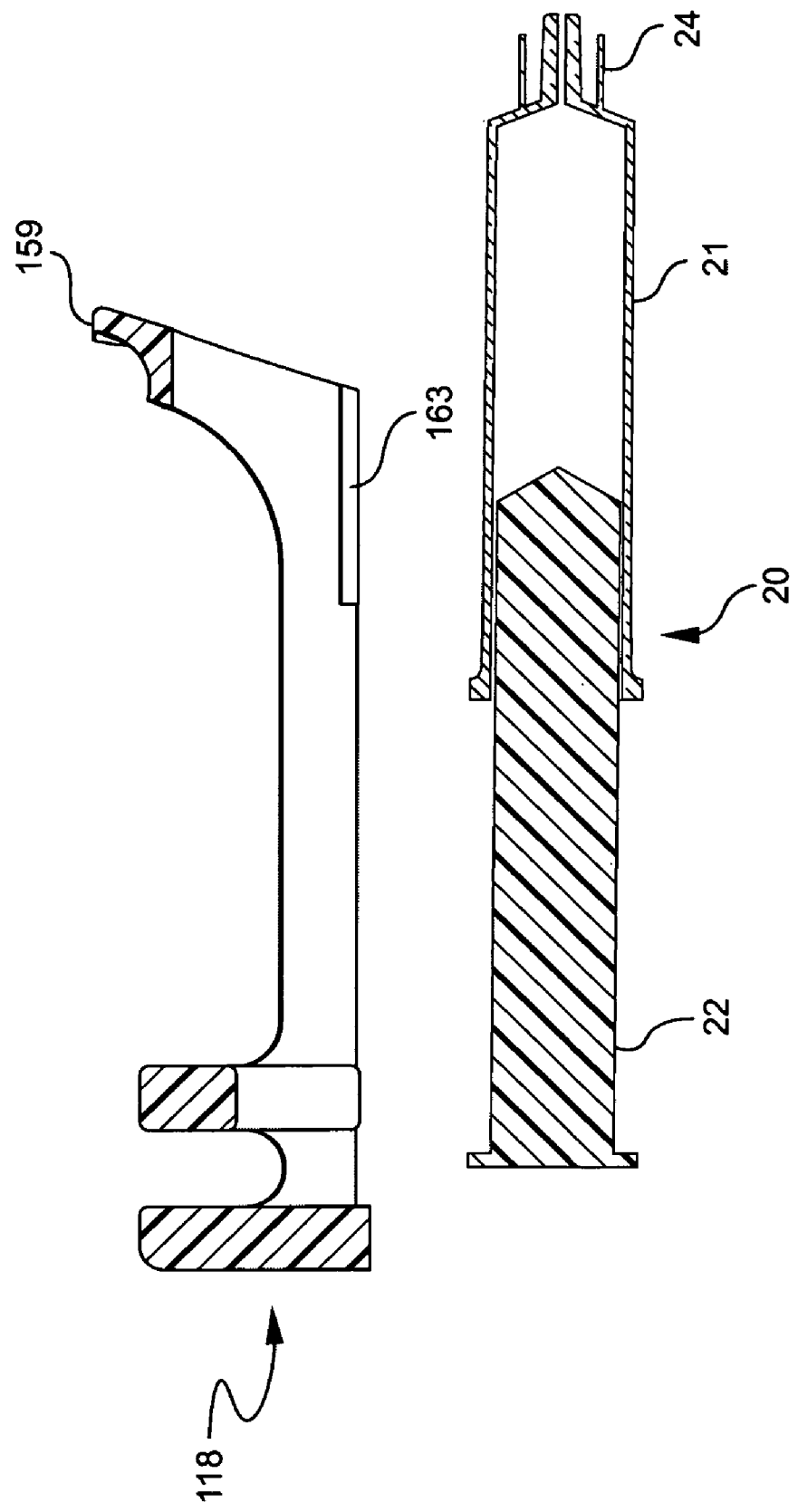
FIG. 44 is an exploded, cross-sectional view of portions of the laparoscopic medical fluid delivery device of the present invention shown in FIGS. 41-43, including a syringe for containing a medical fluid received by the device.
Figure 45:
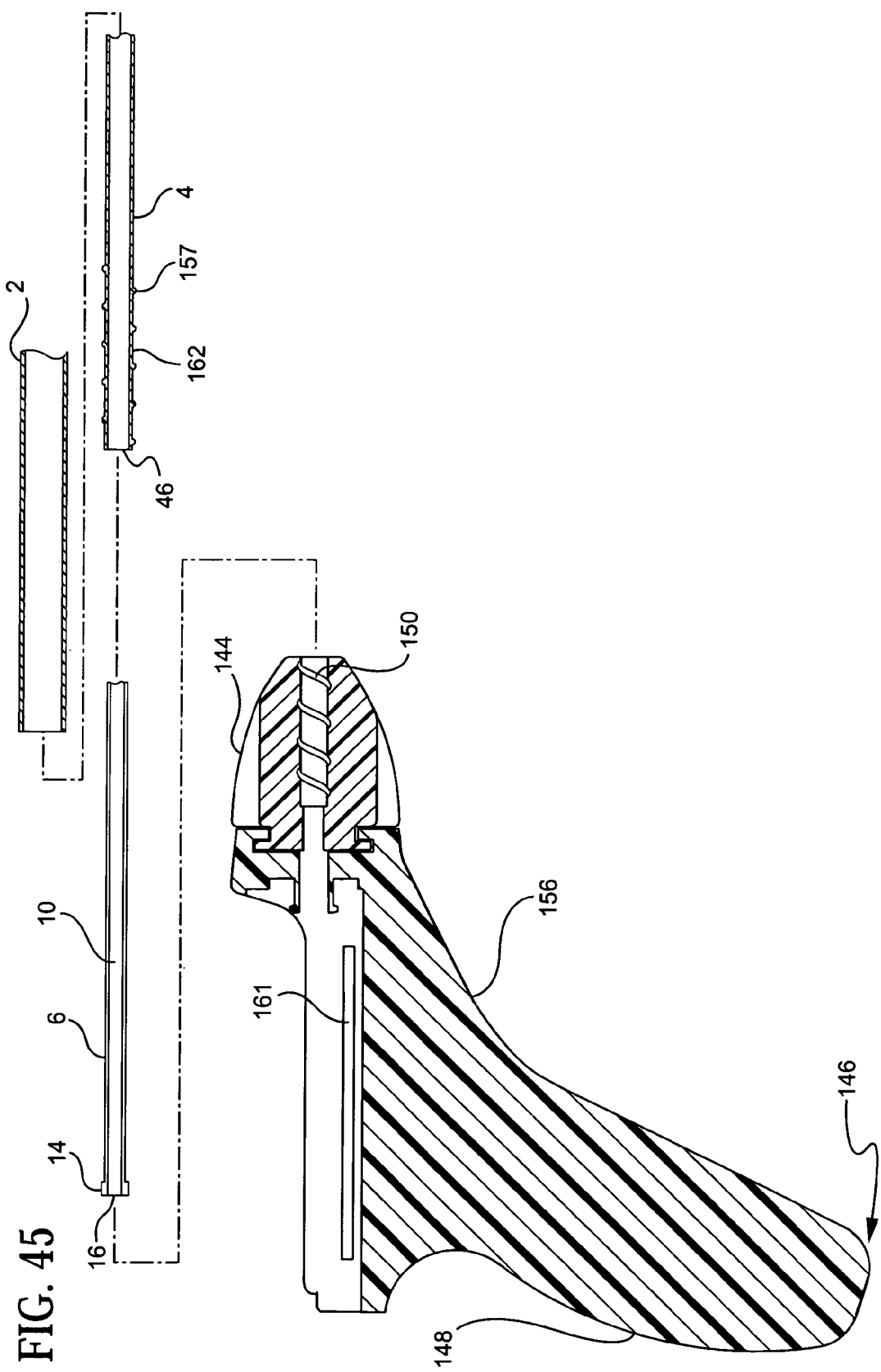
FIG. 45 is an exploded, cross-sectional view of the laparoscopic medical fluid delivery device of the present invention shown in FIGS. 41-44.
Figure 46:
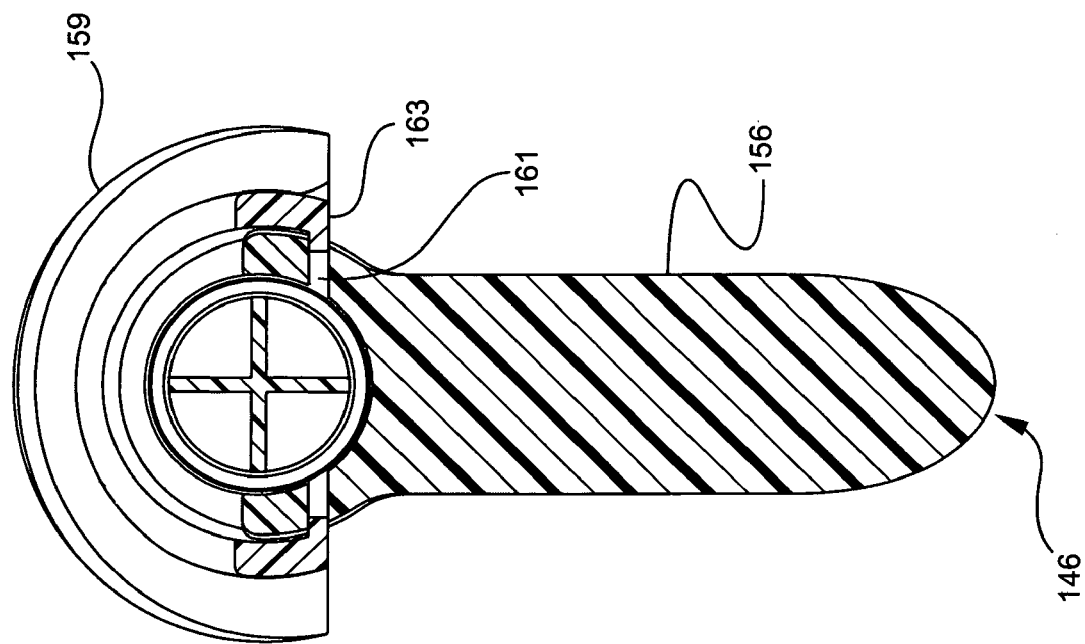
FIG. 46 is a transverse, cross-sectional view of the laparoscopic medical fluid delivery device of the present invention shown in FIGS. 41-45, taken along line 46-46 of FIG. 42.
Figure 47:
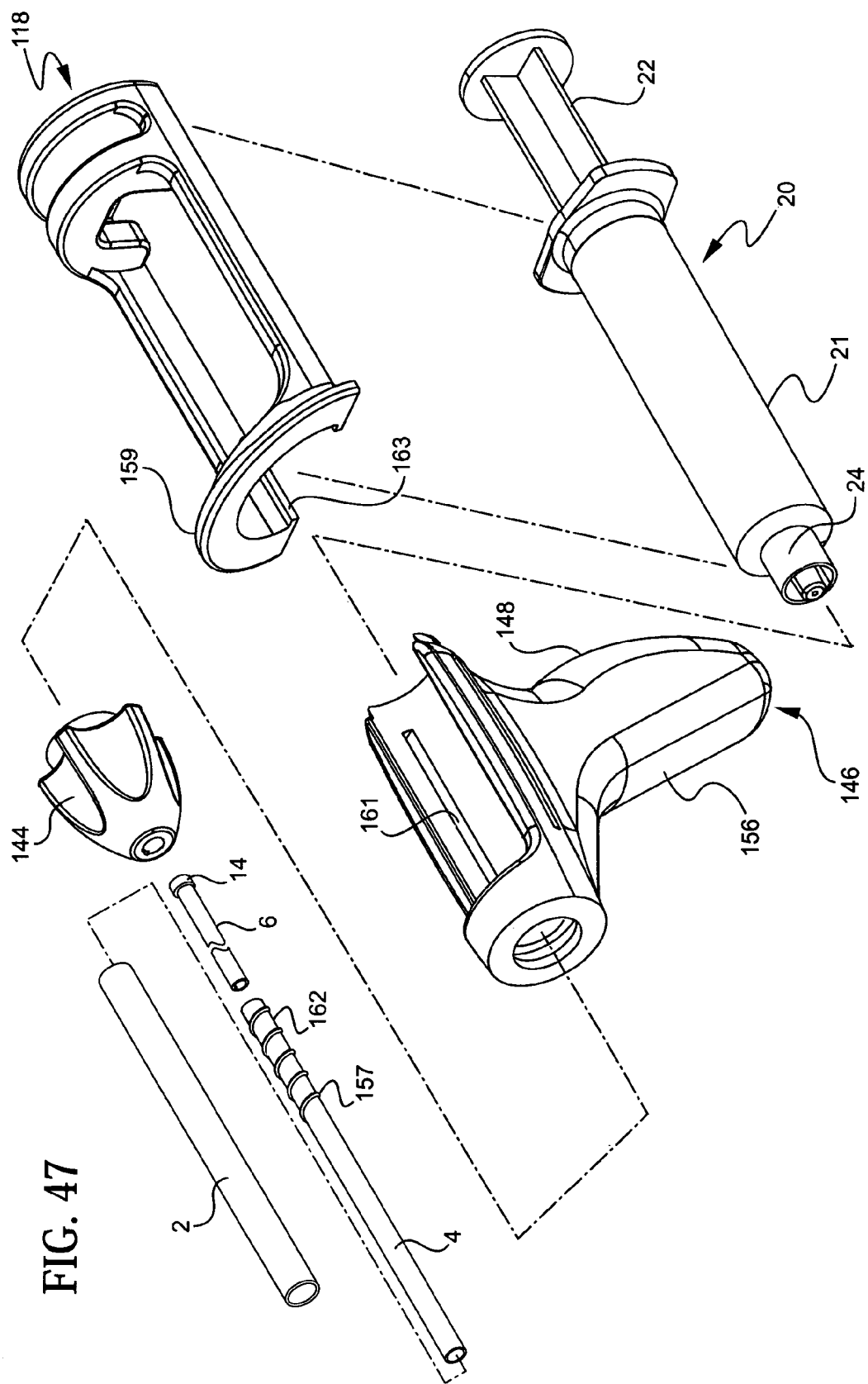
FIG. 47 is an exploded, isometric view of the laparoscopic medical fluid delivery device of the present invention shown in FIGS. 41-46.

The plunger linkage 118 may be situated on one lateral sidewall 130 of the handle housing 76, such as on the right side of the housing, as illustrated by FIGS. 36-40 of the drawings, or may be situated on the other opposite lateral sidewall, such as on the left side of the housing 76. Alternatively, the plunger linkage 118 may be situated on both sides of the handle housing 76, with two rails 122 of the linkage captively received respectively in slots 128 formed through the thickness of the opposite lateral sidewalls of the handle housing, and with a U-shaped plunger engagement structure 142 (such as formed from two interconnected L-shaped members 134 such as described previously) engaging the plunger 22 with the middle portion of the U-shaped structure 142 (see FIG. 41), such as where the middle portion defines a pocket for captively receiving the end of the syringe plunger 22.

A fourth embodiment of the laparoscopic medical fluid delivery device of the present invention is shown in FIGS. 41-47. In this embodiment, the inner tubular member 4 is retracted or advanced on the fluid delivery catheter 6 by rotating a nose piece 144. With this embodiment, the outer tubular member 2, moveable inner tubular member 4 and catheter 6, arranged as described previously in the other embodiments, are mounted to a handle 146, forming part of the actuator of the laparoscopic device, having a handle portion 148 which is graspable by the surgeon. The front end of the handle 146 is formed with a nose piece 144 that is rotatably mounted thereon. The nose piece 144 has a central bore 150 formed axially therethrough. This bore 150 is threaded. The outer tubular member 2 is affixed to the front of the nose piece 144 and rotates with it. The catheter 6 passes through the nose piece bore 150, and has a proximal end which is attached to a luer lock fitting or connector 152, which fitting or connector 152 is attachable to a corresponding luer lock fitting or connector 24 of a syringe 20 containing the medical fluid to be dispensed to the patient.

The proximal end of the inner tubular member 4 passes through the nose piece bore 150 and is axially slidably mounted to the handle housing 156 on which the nose piece 144 is mounted, or is slidably mounted to nose piece 144 which in turn is mounted to handle housing 156. It is prevented from rotating by any number of ways known to one skilled in the art, for example, by having a radially protruding leg (not shown) being slidably received by an axially extending slot (not shown) formed on the inside surface of the handle housing 156. However, a portion 162 of the inner tubular member 4 is formed with threads 157 on the outer surface thereof, which threads 157 engage the threaded bore 150 of the nose piece 144. Thus, by rotating the nose piece 144, the engagement of the nose piece threads and those of the inner tubular member 4 results in axial movement of the inner tubular member on the handle housing 156, as the inner tubular member 4 is prevented from rotating by the engagement of housing edges defining the slot (not shown) mentioned above with the radially extending leg (not shown) also mentioned above. The axial movement of the inner tubular member 4 by rotating the nose piece 144 covers and uncovers the articulating distal tip 8 of the catheter and allows the surgeon to select a desired curvature for the catheter tip with precision.

This fourth embodiment of the present invention may include a plunger linkage 118 having a thumb rest 159 which engages the plunger 22 of the syringe 20 in a manner and with structure similar to that described in relation to the variation of the third embodiment shown in FIGS. 36-40 and described previously. More specifically, the plunger linkage 118 may include mutually inwardly extending rails 163 which are respectively received in slots 161 formed in opposite sidewalls of the handle housing 156.

Figure 57:
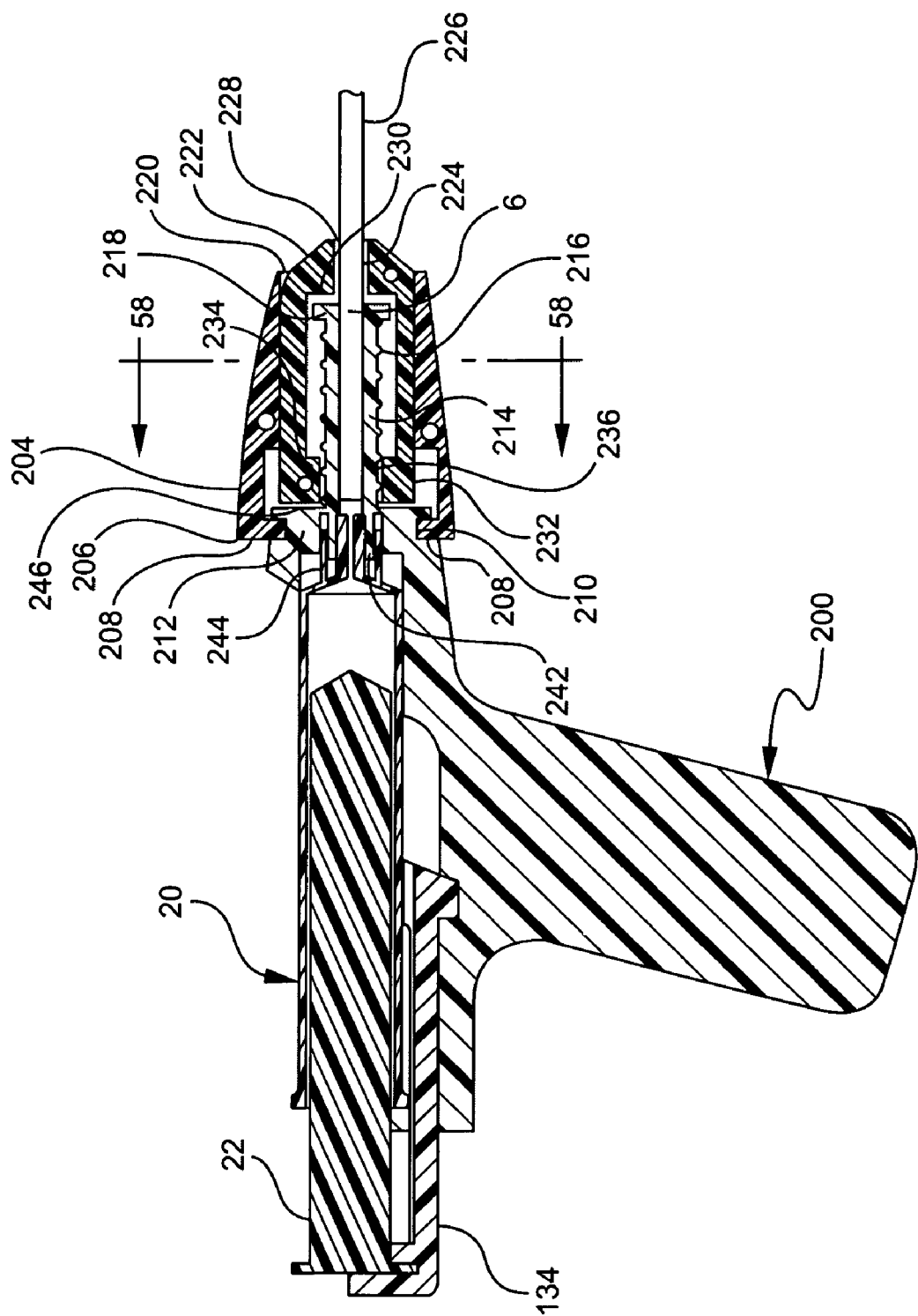
FIG. 57 is a longitudinal cross-sectional view of a laparoscopic medical fluid delivery device constructed in accordance with an alternate form of the present invention from that shown in FIGS. 41-47.
Figure 58:
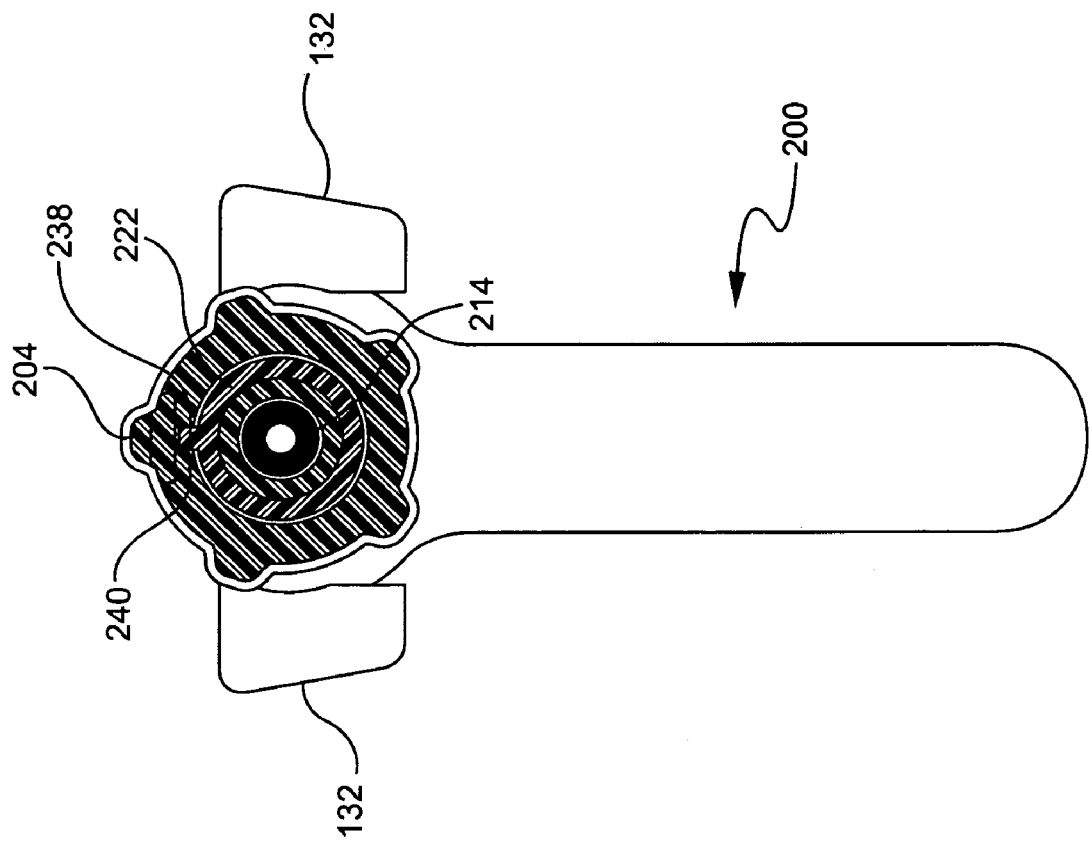
FIG. 58 is a transverse cross-sectional view of the laparoscopic medical fluid delivery device of the present invention shown in FIG. 57 and taken along line 58-58 of FIG. 57.

An alternative version of the laparoscopic medical fluid delivery device shown in FIGS. 41-48 is illustrated by FIGS. 57 and 58. The medical fluid delivery device includes a handle portion 200 having a rotatable nose piece or knob 202, with radially outwardly extending ridges or projections 204 to facilitate the manipulation and grasping of the nose piece by the surgeon. The nose piece 202 has a proximal axial end 206 formed with a radially inwardly extending flange 208 that is captively but rotatably received by a channel 210 formed circumferentially in the forward portion 212 of the handle portion 200 on which the nose piece 202 is rotatably mounted. The forward portion 212 of the handle portion 200 includes an axially extending inner tubular member 214 having a threaded outer surface 216, and a radially outwardly extending lip 218 situated at the free end thereof.

The nose piece 202 has an axial bore 220 in which is situated a generally cylindrical collar 222. The proximal axial end 224 of the inner sleeve 226 is closely received by a central bore 228 formed in the collar 222 so that the inner sleeve 226 is affixed to the distal axial end 230 of the collar 222 and movable with it. The opposite proximal end 232 of the collar 222 includes a radially inwardly extending boss 234 having an inner wall 236 that is complementary threaded to receive and engage the threads 216 of the inner tubular member 214.

A rib 238 extending radially from the outer surface of the collar 222 and at least partially axially along the length thereof is slidably received by a channel 240 formed axially in the inner surface of the rotatable nose piece 202 to operatively link the nose piece 202 to the collar 222 so that the nose piece 202 and collar 222 rotate together when the nose piece 202 is turned by the surgeon, but which allows the collar 222 to move axially forward and backward in the nose piece bore 220 when the nose piece 202 is turned. The front portion 212 of the handle portion 200 is formed with a luer lock fitting 242 or other connector which mates with the luer lock fitting 244 or connector of the syringe, as shown in FIG. 57.

The structure of the nose piece 202 and cooperating components of the laparoscopic medical fluid delivery device shown in FIGS. 57 and 58 allows the articulating tip portion of the catheter 6 to be covered and uncovered by the inner sleeve 226 when the nose piece 202 is turned. More specifically, rotating the nose piece 202 causes the collar 222 that is operatively coupled thereto to rotate with it. Since the boss 234 on the collar 222 threadingly engages the stationary threaded inner tubular member 214 of the handle portion 200, the collar 222 will move axially within the bore 220 of the nose piece 202. The forward movement of the collar 222 is arrested by the radially extending lip 218 of the tubular member 214 engaging the inner side surface of the collar boss 234, and rearward movement of the collar 222 is stopped when the outer surface of the collar boss 234 engages a front wall 246 of the forward portion 212 of the handle portion 200.

Since the proximal end 224 of the inner sleeve 226 is affixed to the collar 222, as the collar 222 moves axially, so will the inner sleeve 226 to cover and uncover the articulating tip portion of the catheter 6, depending on the direction of rotation of the nose piece 202.

The laparoscopic medical fluid delivery device shown in FIGS. 57 and 58 includes a thumb rest 132 situated on both lateral sides of the handle housing, as well as a plunger linkage 134 operatively coupled between the thumb rest 132 and the plunger 22 of the syringe 20 to effect movement of the plunger within the syringe when the surgeon presses on the thumb rest 132 with his finger, such as described previously with the embodiment of the present invention shown in FIGS. 36-40 and the embodiment shown in FIGS. 41-47.

The laparoscopic fluid delivery devices described herein generally have an overall length, including the handle portion, of between about 46 centimeters and about 63 centimeters, with the outer and inner tubular members extending from the handle or actuator portion of the device a distance of between about 28 centimeters and about 45 centimeters, although the device may be constructed in shorter versions that are perfectly suitable for use in open surgical procedures.

Figure 48:
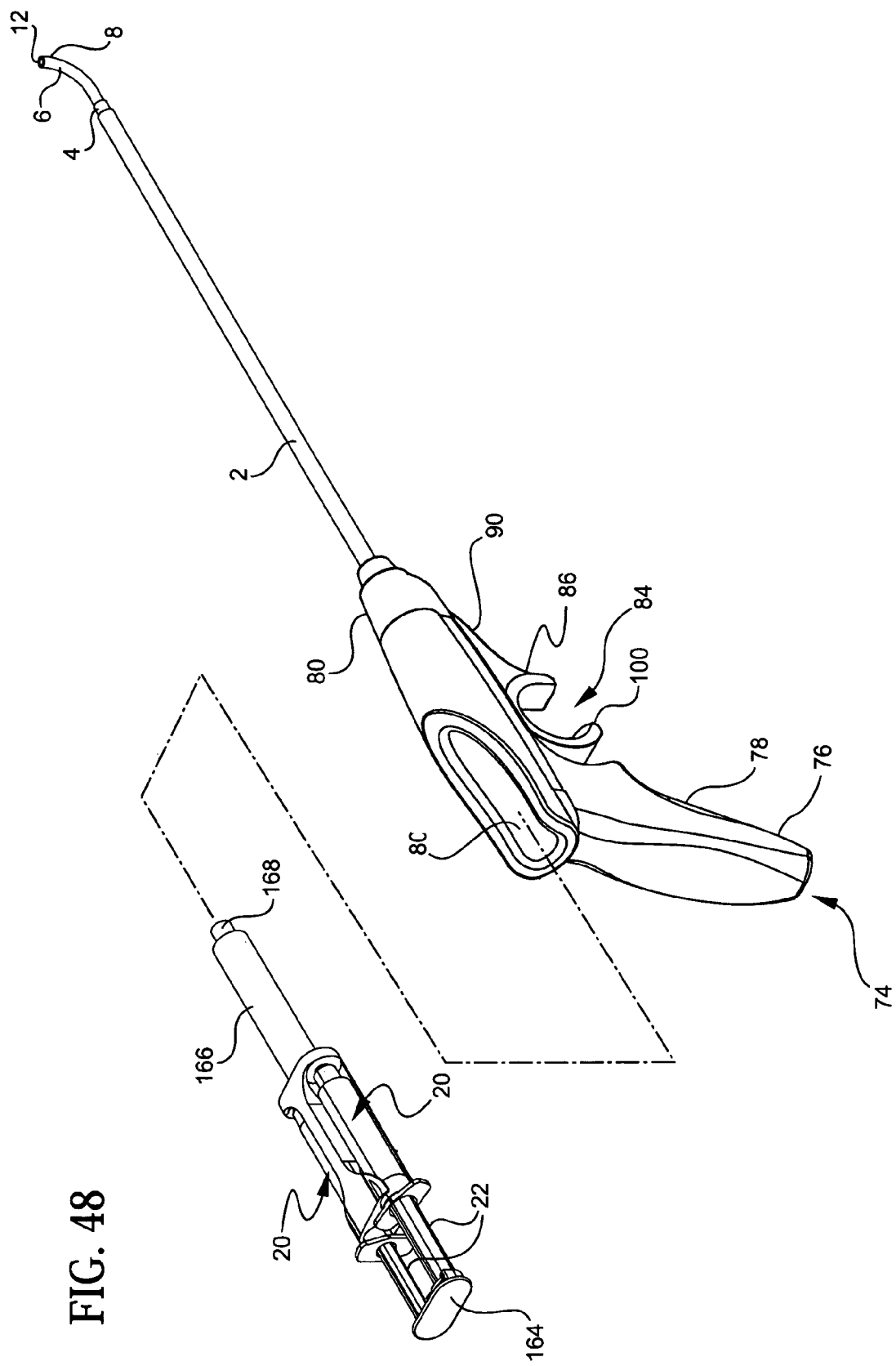
FIG. 48 is an exploded, isometric view of a laparoscopic medical fluid delivery device of the present invention and a dual syringe and mixer assembly being receivable thereby.
Figure 49:
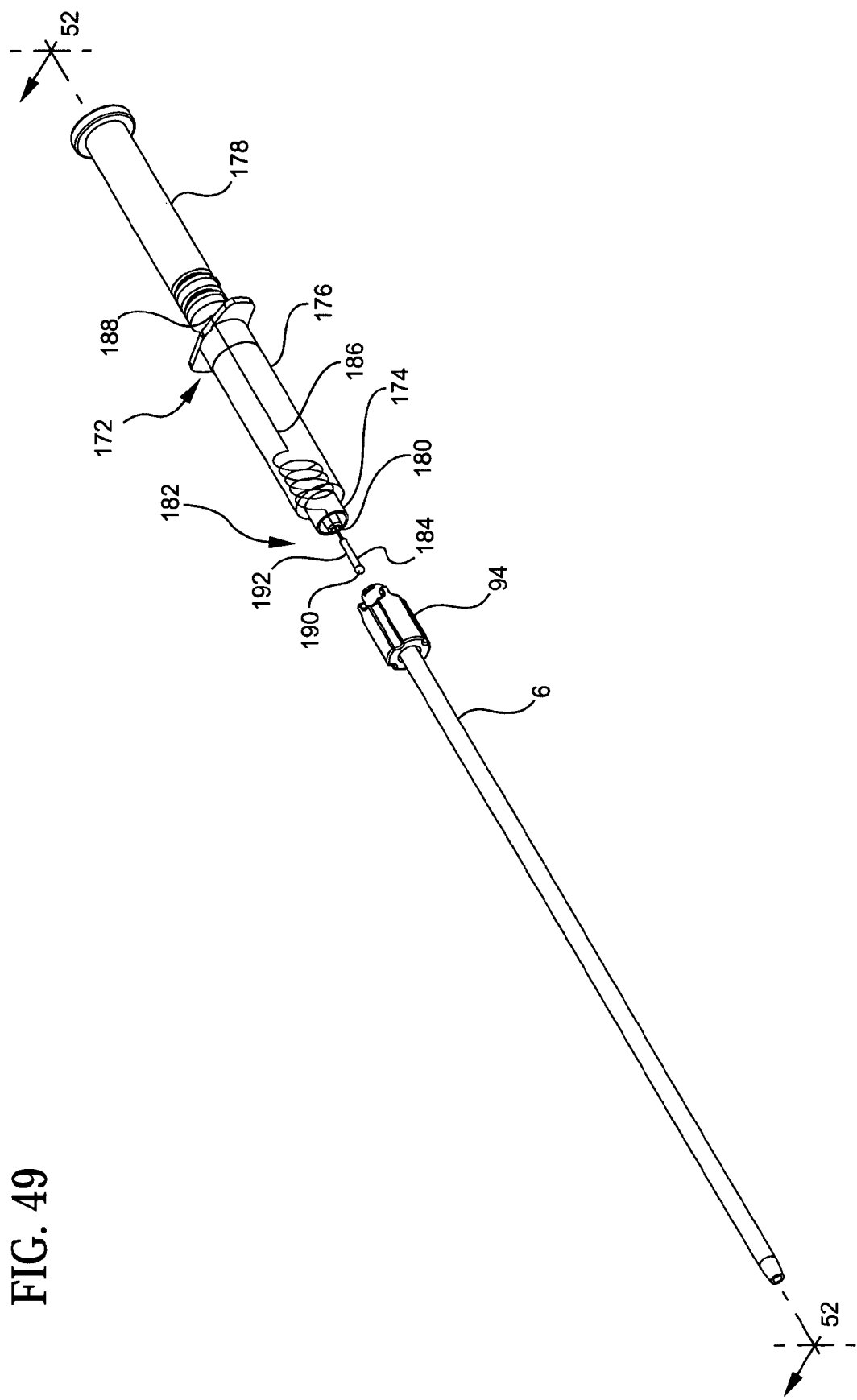
FIG. 49 is a partially exploded, isometric view of a specially designed syringe formed in accordance with the present invention to expel fluid entrapped in a catheter of a laparoscopic medical fluid delivery device.
Figure 50:
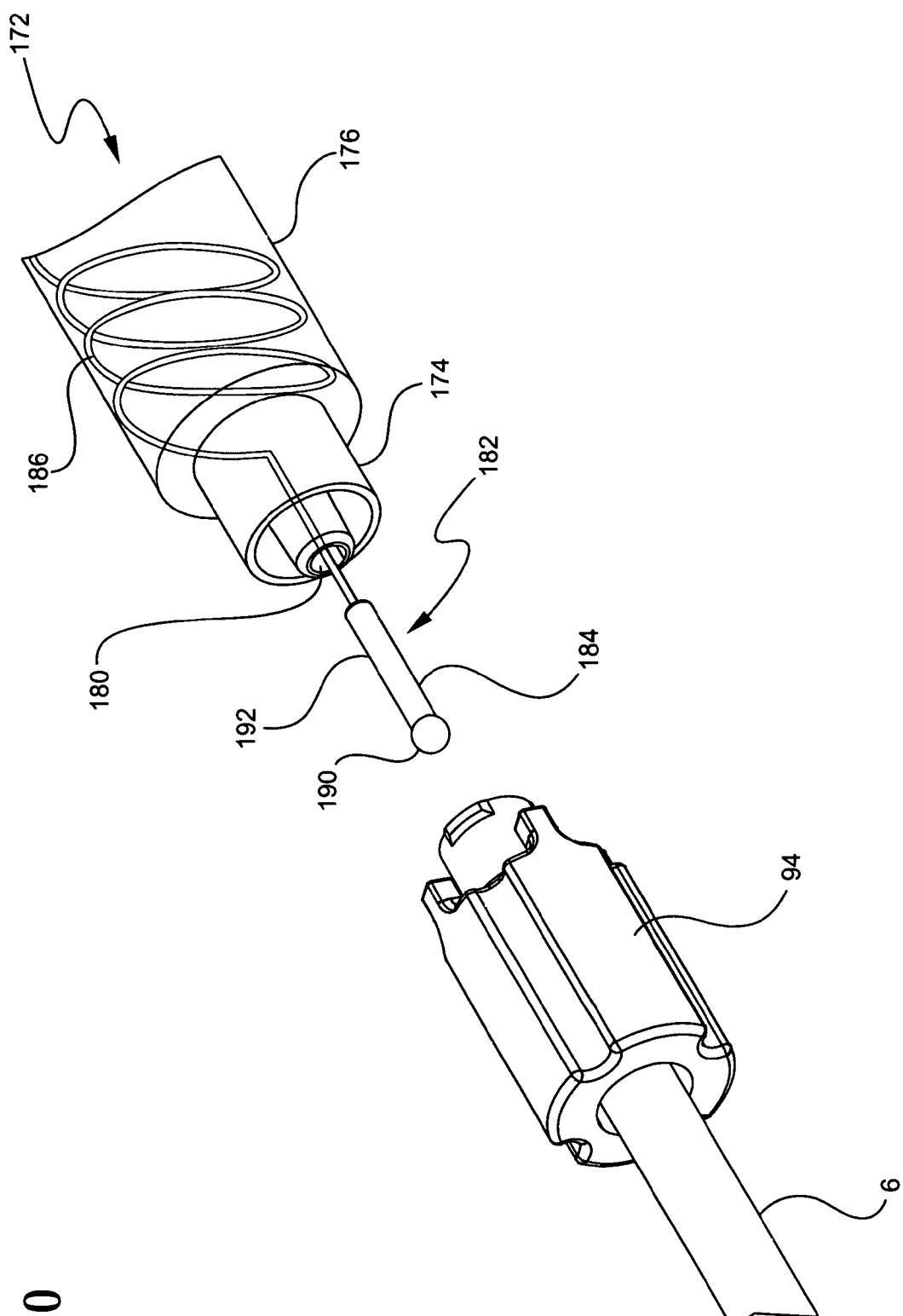
FIG. 50 is a partially exploded, enlarged, isometric view of portions of the specially designed syringe of the present invention used to expel entrapped fluid from a catheter of a laparoscopic medical fluid delivery device.
Figure 51:
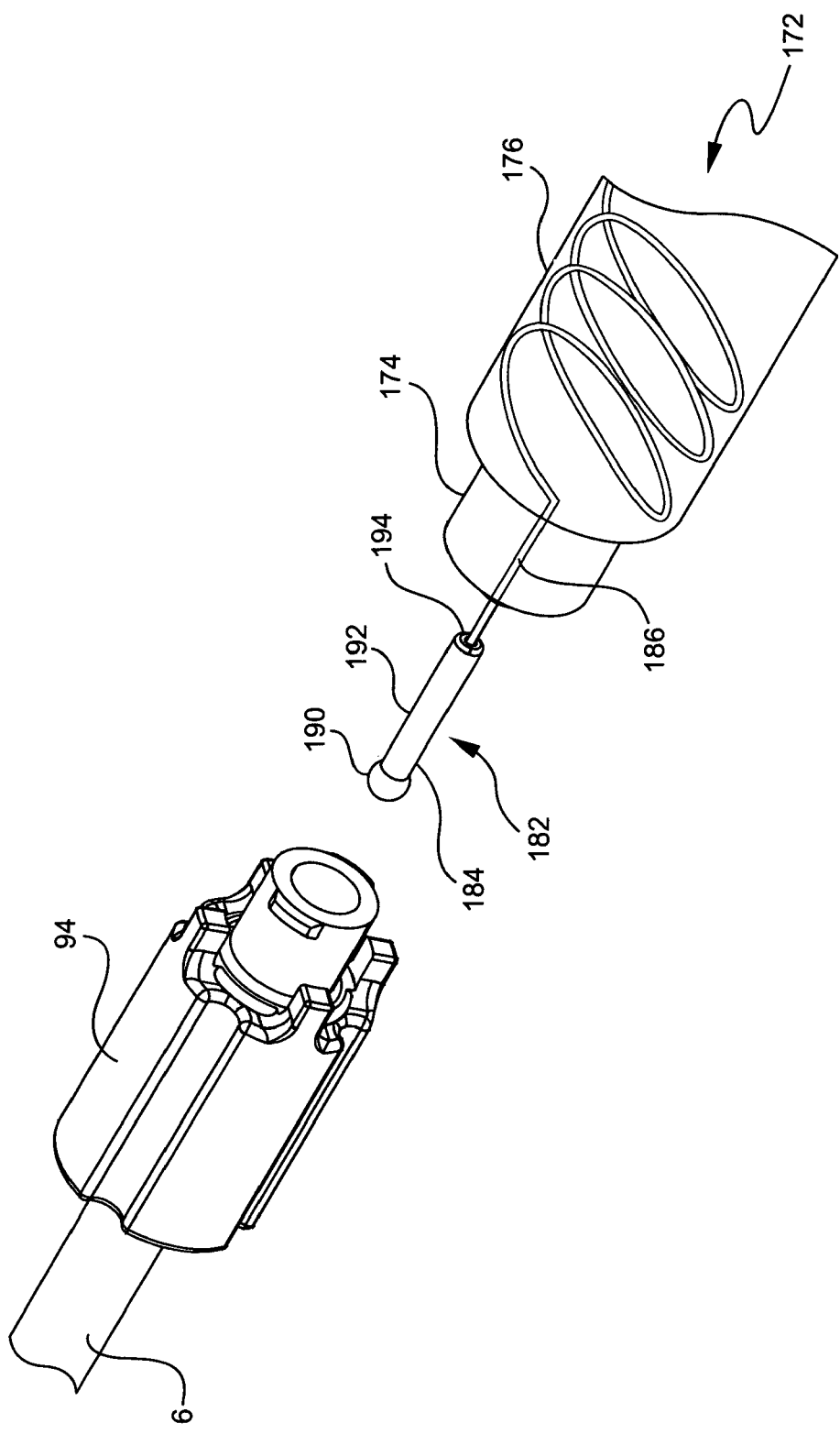
FIG. 51 is a partially exploded, enlarged, isometric view of portions of the specially designed syringe of the present invention for expelling entrapped fluid from a catheter of a laparoscopic medical fluid delivery device, taken from a different view from that shown in FIG. 50.
Figure 52:
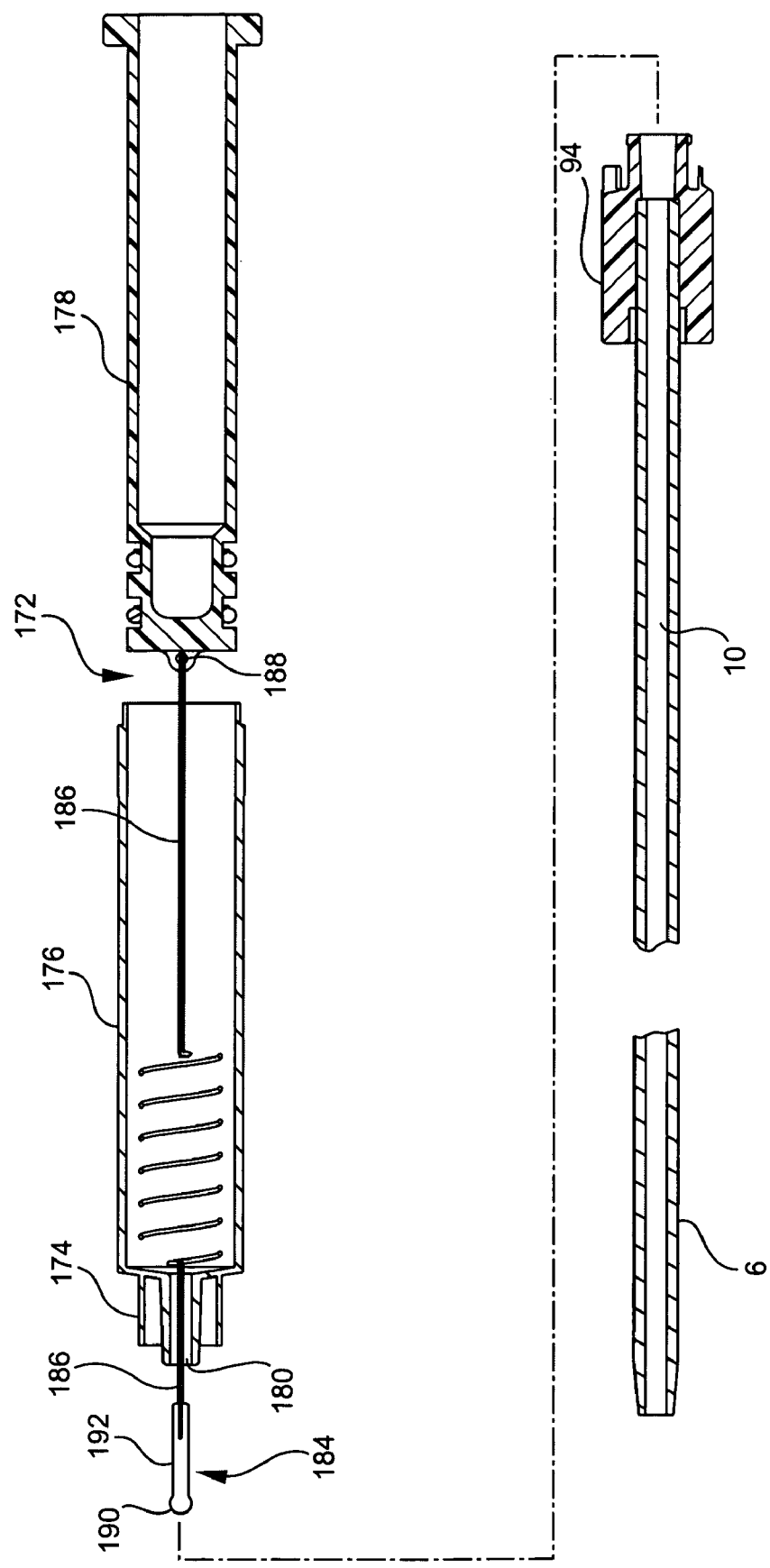
FIG. 52 is an exploded, cross-sectional view of the specially designed syringe of the present invention shown in FIGS. 49-51 and the catheter of a laparoscopic medical fluid delivery device.
Figure 53:
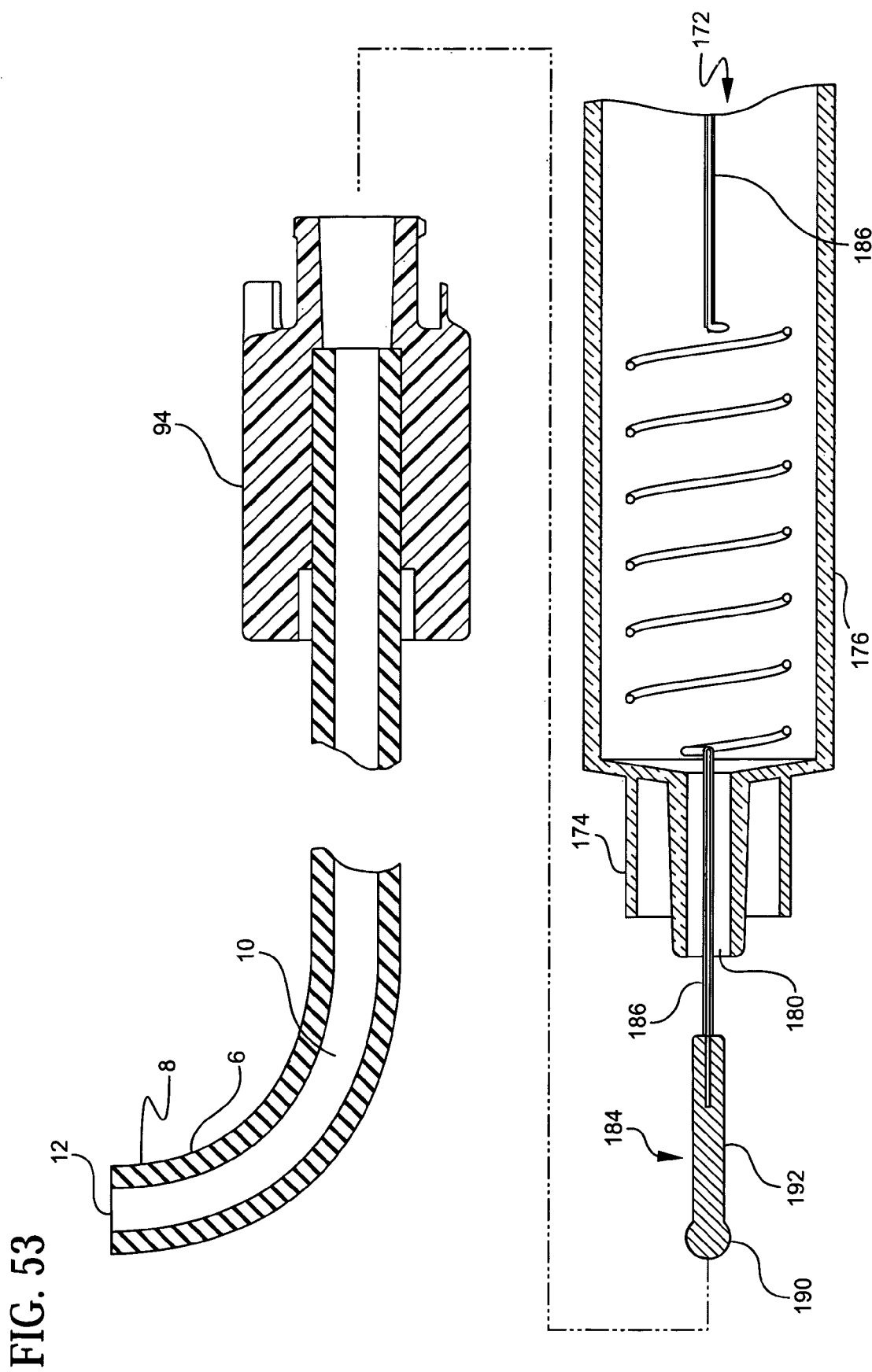
FIG. 53 is an exploded, enlarged, cross-sectional view of portions of the specially designed syringe of the present invention shown in FIGS. 49-52 and a catheter having an articulating tip of a laparoscopic medical fluid delivery device formed in accordance with the present invention.

It should be noted here that the various embodiments of the laparoscopic medical fluid delivery device of the present invention described herein are perfectly adaptable for receiving a single syringe 20 or a dual syringe system both with and without static mixers. This capability is illustrated in FIG. 48 of the drawings, and is described in greater detail below.

More specifically, sterilization and stability of medical fluids, such as a sealant combined with an anti-adhesion component, have been a challenge for chemists for many years. The two components cannot be mixed prematurely, and should be mixed just prior to delivery to a surgical site.

The barrel 54 of the laparoscopic fluid delivery device of the present invention can accept a single syringe 20 or a dual syringe system. The dual syringe system would include two syringes 20, each having plungers 22 that are ganged together by a linkage 164 for comparable axial movement within their respective syringe bodies. The syringe tips are joined to respective inlet ports of a static mixer 166, whose outlet is fitted with a luer lock fitting or connector 168 that mates with the luer lock fitting or connector 94 on the proximal end of the catheter 6 of the laparoscopic fluid delivery device.

Accordingly, the dual syringe system may have its static mixer 166 received by the barrel 80 formed in the handle housing 76 of the laparoscopic fluid delivery device of the present invention, and fluid may be expressed from each syringe 20 concurrently by thumb pressure or by using a plunger linkage 118, as described previously, mixed in the static mixer 166, and delivered to the surgical site through the lumen 10 and opening 12 in the articulating catheter tip 8 of the laparoscopic medical fluid delivery device of the present invention. Accordingly, the laparoscopic fluid delivery device of the present invention allows effective delivery of expensive components mixed during or just prior to their use.

Another problem which occurs with conventional laparoscopic devices is that the medical fluid remains trapped in the internal lumen 10 of the catheter 6. These medical fluids, such as sealants, adhesives, flowable haemostatic agents, antibiotics and the like, are usually relatively expensive, and it is the desire of surgeons to utilize all of the medical fluid in a delivery device with little waste.

As mentioned previously, a laparoscopic instrument is typically about 28 to about 45 centimeters long and, depending on the internal lumen diameter of the catheter 6, can trap a considerable amount of medical fluid. Accordingly, the method and structure of the present invention, now further described in greater detail, address this concern of physicians and solve the problem of medical fluids being trapped in the catheter lumen of a laparoscopic instrument.

As shown in FIGS. 49-53, a special syringe 172, constructed in accordance with the present invention, has been devised which liberates entrapped medical fluids within a catheter lumen, such as in the internal lumen 10 of the laparoscopic fluid delivery device of the present invention described previously. However, it should be realized that the method and apparatus described herein for liberating entrapped medical fluid are applicable to most, if not all, laparoscopic fluid delivery devices, and are not limited to the particular laparoscopic fluid delivery devices of the present invention described herein.

After medical fluid has been previously delivered to a patient by a laparoscopic fluid delivery device using a syringe 20 containing the medical fluid, the specially designed syringe 172 of the present invention may be substituted therefor. This syringe 172 is placed in the barrel 80 of the laparoscopic fluid delivery device formed in the top portion of the handle 74, such as described previously and shown in FIGS. 21-27. The syringe 172 includes a luer lock fitting or connector 174 so that it can mate with the corresponding luer lock fitting or connector 94 to which the proximal end of catheter 6 is attached.

The syringe 172 includes a barrel 176 having a bore formed axially therethrough, which receives a plunger 178 that may reciprocatingly slide axially in the barrel 176. The syringe 172 is filled with a gas, such as air, although it may contain a liquid, such as a saline solution, which is relatively incompressible to force more viscous medical fluids, e.g., adhesives and sealants, from the lumen 10 of the catheter 6 of the laparoscopic fluid delivery device. The syringe 172 further has a luer lock fitting 174 at the tip of the syringe, the luer lock fitting 174 having an orifice 180 which is in fluid communication with the barrel bore.

The syringe 172 includes a seal assembly 182, which preferably includes a lap seal 184 and a connecting line 186, such as a suture, which is affixed to the end of the lap seal 184 and to the syringe barrel 176 or tip or to the forward end of the plunger 178 that is received by the syringe barrel. For example, the forward end of the syringe plunger 178 received by the barrel 176 may include a mounting point, such as a protruding eyelet 188, through which the end of the connecting line 186 is passed and to which it is tied. Preferably, the lap seal 184 is formed with a bulbous head 190, having a diameter which is equal to or slightly less than the inner diameter of the catheter lumen 10. A rod 192 extends radially from the bulbous head 190, the rod 192 having a diameter which is equal to or slightly less than the inner diameter of the syringe tip orifice 180 defined by the luer lock fitting or connector 174 situated thereon. The free end of the rod 192 is attached to the connecting line 186 (e.g., the suture). For example, the free end of the rod may have a bore 194 formed axially at least partially therethrough to which the end of the connecting suture 186 is received and adhesively secured therein. The lap seal 184 is preferably situated on the syringe 172, with the rod 192 being seated in the syringe tip, and with the bulbous head 190 of the lap seal resting thereon. The connecting line 186, or suture, is coiled within the barrel bore of the syringe 20 prior to use. Although the preferred form of the lap seal 184 includes a bulbous head 190 and a rod 192 connected thereto as described above, it is envisioned to be within the scope of the present invention to form the lap seal with other shapes and configurations, such as a sphere, elliptical capsule and the like.

During use, the specially designed syringe 172 is loaded into the barrel 80 of the laparoscopic device, and its luer lock fitting 174 is mated to the luer lock fitting 94 of the catheter 6. The surgeon uses the laparoscopic fluid delivery device of the present invention in the manner described previously, or another laparoscopic delivery device, by forcing the plunger 178 of the syringe into the barrel 176 thereof to express the fluid or gas contained within the syringe. Since the fluid or gas is upstream of the adhesive, sealant or other medical fluid entrapped in the catheter lumen 10 of the delivery device, and separated therefrom by the lap seal 184, the fluid or gas does not come in direct contact with the entrapped medical fluid.

When the plunger 178 of the syringe 172 is actuated, the lap seal 184 is pushed by air or other fluid into the catheter lumen 10 of the laparoscopic fluid delivery device. Because of the relatively large diameter of the bulbous head 190 of the lap seal closely engaging the interior walls of the catheter 6 defining the lumen 10, the lap seal 184, under pressure from the gas or fluid forced out of the syringe 172, will travel down the length of the catheter lumen 10, pushing out the trapped sealant or other medical fluid therefrom.

The connecting line 186 or suture has a length which is selected to ensure that the lap seal 184 does not escape out the distal opening 12 in the catheter tip 8 of the laparoscopic fluid delivery device and into the patient's body cavity. The connecting line 186, which is attached to the free end of the rod 192 of the lap seal, will uncoil from inside the syringe barrel 176 and feed through the syringe tip and lumen 10 as the lap seal 184 travels axially along the length of the catheter lumen. The syringe 172 contains enough air or fluid to push the lap seal 184 to the distal end of the catheter tip of the laparoscopic fluid delivery device, and the length of the connecting line 186 limits the travel of the lap seal 184 through the catheter lumen 10.

Figure 54:
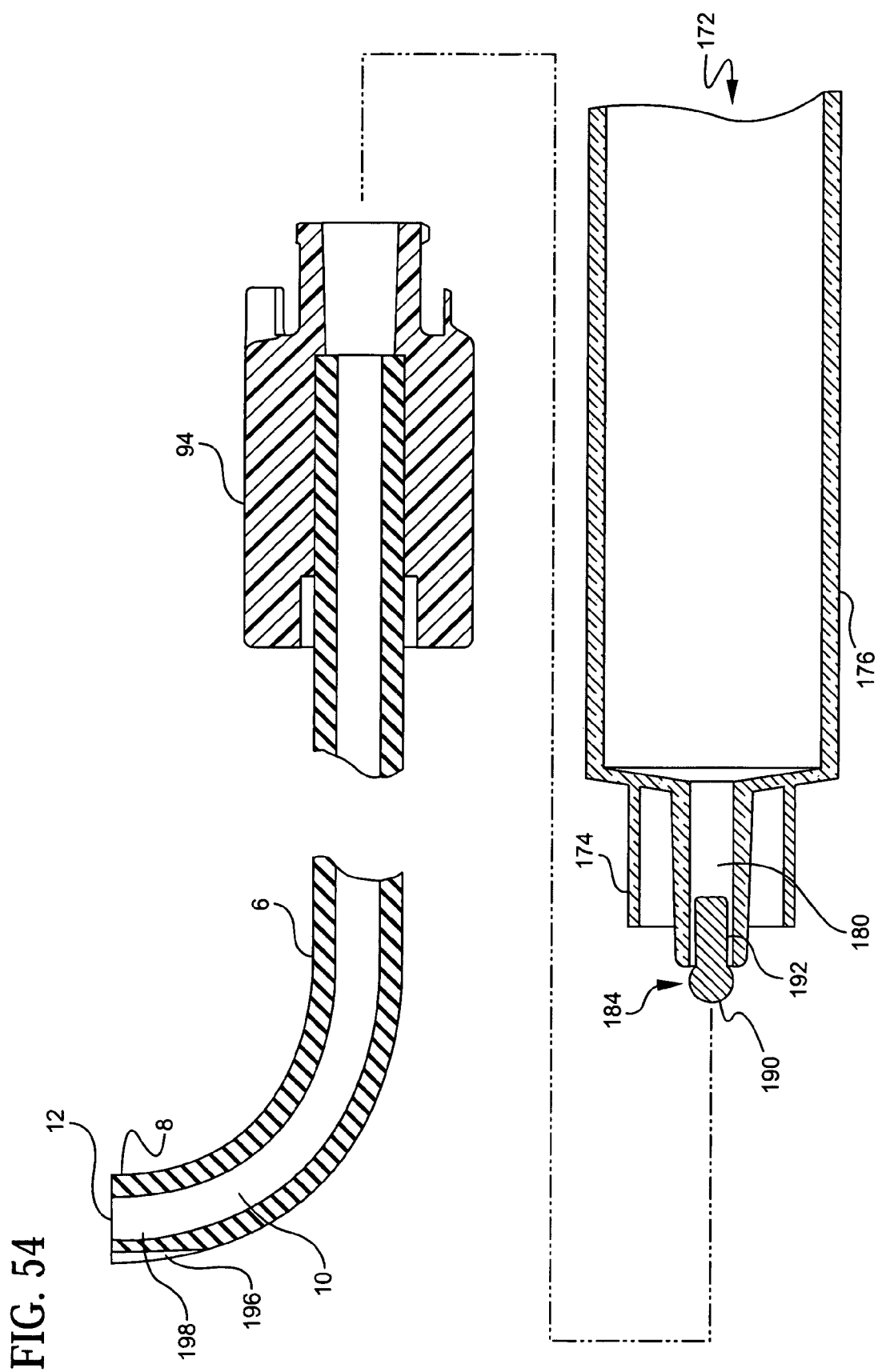
FIG. 54 is an exploded, enlarged, cross-sectional view of portions of a specially designed syringe constructed in accordance with a second form of the present invention for expelling fluid from a catheter of a laparoscopic medical fluid delivery device, and illustrating the catheter of the laparoscopic medical fluid delivery device formed in accordance with the present invention.

In accordance with a second embodiment of the present invention, and as shown in FIGS. 54-56, a syringe 172, as described previously, may be used to express sealant, adhesive or other medical fluid remaining in a laparoscopic fluid delivery device. Again, as with the previous embodiment, the syringe 172 may contain a fluid, liquid or gas, and may include a lap seal 184, as described previously. However, in this particular embodiment, the lap seal 184 need not be tethered to the syringe plunger 178 by the connecting line 186, but rather is blocked from entering the patient's body cavity by a deformation formed at the distal end of the catheter tip.

More specifically, and as shown in FIGS. 54-56 of the drawings, the distal end of the articulating catheter tip 8 may have formed therein a deformation 196 on its outer sidewall, which causes a protrusion 198 to extend slightly radially inwardly of the inner catheter sidewall defining the lumen 10, effectively narrowing the overall diameter of the catheter lumen at the articulating tip 8 of the catheter 6 to that which is smaller than the diameter of the bulbous head 190 of the lap seal 184. Thus, the lap seal 184 may travel through most of the catheter lumen 10, but when it reaches the distal end of the catheter tip, the diameter of the bulbous head 190 of the lap seal is greater than the inner diameter of the lumen 10 at the catheter tip 8 and, therefore, is prevented by the smaller diameter of the catheter tip from being expelled under pressure from the catheter tip opening 12 into the patient's body cavity.

Of course, it is envisioned to be within the scope of the present invention to provide other structure to prevent the lap seal 184 from being expelled from the catheter tip opening 12. A thin wire (not shown) may be positioned diametrically across the inner sidewall of the catheter tip defining the lumen thereat, which wire is small enough so as not to impede the flow of medical fluid therethrough but prevent the lap seal 184 from passing through the distal end opening 12 of the catheter tip 8. Alternatively, the catheter tip 8 may be formed with a slightly smaller inner diameter of its lumen 10 at the catheter tip as opposed to over other portions of the lumen, thus preventing the lap seal 184 from being expressed under pressure through the distal end opening 12 of the catheter tip 8.

It is preferred that the lap seal 184, and in particular the length and diameter of the rod 192 and the diameter and overall size of the bulbous head 190 thereof, is dimensioned such that the lap seal 184 does not become lodged in the articulating tip 8 of the catheter due to its curvature.

The laparoscopic fluid delivery device of the present invention, in the form of the various embodiments described herein, and with its pre-shaped catheter, is simple to manufacture and uncomplicated in structure. It omits the need for ganged pieces defining a multi-slotted catheter tip controlled by one or more wires to effect the articulation of the tip found in the rather complicated structure of conventional laparoscopic devices. The laparoscopic delivery device of the present invention provides one-handed operation for the surgeon to precisely dispense medical fluid at a desired tissue site in the patient, and decreases the likelihood of depositing fluid inadvertently on non-targeted areas.

The laparoscopic fluid delivery device of the present invention has the capability of rotating the articulating catheter tip 8 three hundred, sixty degrees (360°) for precise deposition of medical fluids. It also has the ability to handle single syringes 20 filled with medical fluid, as well as dual syringe systems both with and without static mixers 166, thus addressing the problems of sterilization and stability of medical fluids, such as a sealant with an anti-adhesion component, that have challenged chemists in the past. The present invention also allows for the effective delivery of expensive medical fluid components mixed during or just prior to use. Also, although the catheter 6 is described and shown as having a single lumen 10, it may be formed with multiple, parallelly extending lumens, and such a structure would be quite advantageous when using multiple component fluids that only come into contact with one another when dispensed at the surgical site.

The subsequent-use special syringe 172 for expelling entrapped sealants, adhesives or other medical fluids from the catheter lumen 10 also advantageously minimizes any waste of such expensive fluids. The fluid-expelling syringe 172 of the present invention is a cost effective approach for dispensing trapped medical fluid. The syringe 172 is relatively small, unlike the conventional ramrod device. Furthermore, it does not change the tactile feel of the laparoscopic fluid delivery device when used to expel trapped medical fluid in the catheter lumen 10, and the surgeon is enabled to precisely deliver a medical fluid to a targeted tissue site without having to vary or change his grasp or operation of the laparoscopic fluid delivery device.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A medical fluid delivery device, which comprises:
 a catheter, the catheter having at least one lumen formed axially therethrough for the passage therein of a medical fluid, the catheter further having an articulating tip formed with shape memory properties and having a pre-shaped curvature;
 an elongated first tubular member, the first tubular member having an axial bore formed therein, the catheter residing at least partially within the axial bore of the first tubular member, the first tubular member being reciprocatingly slidable axially on the catheter to selectively cover and uncover portions of the articulating tip to thereby selectively vary a degree of curvature of the articulating tip, the pre-shaped articulating tip of the catheter being constrained by the first tubular member from articulating to the pre-shaped curvature when the first tubular member covers the articulating tip, the pre-shaped articulating tip of the catheter bending to a selected degree of curvature when the articulating tip is at least partially uncovered by the first tubular member;

an actuator operatively coupled to the first tubular member to selectively move the first tubular member reciprocatingly on the catheter; and an elongated second tubular member, the elongated second tubular member having an axial bore formed therein, the first tubular member being at least partially received by the axial bore of the second tubular member and being reciprocatingly slidable therein, wherein each of the first tubular member and the second tubular member is a straight, non-flexible member, and wherein the catheter and the second tubular member are fixed from axial movement relative to one another and the first tubular member is adapted for axial movement relative to both the fixed catheter and the fixed second tubular member.

2. A medical fluid delivery device as defined by claim 1, wherein the catheter has a distal end and a proximal end situated axially opposite the distal end, the articulating tip of the catheter being situated at the distal end thereof; and wherein the device further includes a luer fitting mounted on the proximal end of the catheter for connection to a syringe containing a medical fluid therein.

3. A medical fluid delivery device as defined by claim 1, wherein the articulating tip is formed from a pre-shaped elastomeric material.

4. A medical fluid delivery device as defined by claim 1, wherein the articulating tip is formed from a shape-memory alloy comprising an intermetallic compound of nickel and titanium.

5. A medical fluid delivery device as defined by claim 1, wherein the actuator includes a collar, the collar being slidably situated on the second tubular member and being operatively linked to the first tubular member to move the first tubular member reciprocatingly in the second tubular member and on the catheter to cover and uncover the articulating tip of the catheter.

6. A medical fluid delivery device as defined by claim 5, wherein the collar includes a main body, a first flange radially extending outwardly from the main body, and a second flange radially extending outwardly from the main body, the first and second flanges being spaced apart axially from each other to define a finger slot therebetween.

7. A medical fluid delivery device as defined by claim 6, wherein the second tubular member has a distal end and a proximal end situated axially opposite the distal end, the distal end of the second tubular member being situated generally near the articulating tip of the catheter, the proximal end of the second tubular member having a slot formed axially therein, the collar being slidably mounted on the proximal end of the second tubular member; and wherein the collar further includes a linkage, the linkage being reciprocatingly slidable in the slot formed in the proximal end of the second tubular member, the linkage being joined to the main body of the collar and the first tubular member, wherein axial movement of the collar on the second tubular member causes axial movement of the first tubular member to cover and uncover the articulating tip of the catheter.

8. A medical fluid delivery device as defined by claim 7, wherein the first tubular member has a distal end and a proximal end situated axially opposite the distal end, the distal end of the first tubular member being situated in proximity to the articulating tip of the catheter, the first tubular member including a sidewall having an outer surface; and wherein the linkage is affixed to the outer surface of the sidewall of the first tubular member at the proximal end thereof.

9. A medical fluid delivery device as defined by claim 8, wherein the linkage includes an L-shaped member having a first leg and a second leg joined to the first leg, the first leg being affixed to the outer surface of the sidewall of the first tubular member and reciprocatingly slidably received by the slot formed in the proximal end of the second tubular member, the second leg of the L-shaped member being joined to the main body of the collar.

10. A medical fluid delivery device as defined by claim 8, wherein the linkage includes a set screw, the set screw being received in a threaded hole formed in the main body of the collar.

11. A medical fluid delivery device as defined by claim 1, wherein the actuator includes:

a handle portion, the handle portion having a housing defining a handle for grasping by a person manipulating the device, and further defining a barrel for receiving therein a syringe containing a medical fluid;

a collar, the collar being situated on the second tubular member and being operatively linked to the first tubular member; and a trigger arm, the trigger arm being pivotally mounted to the housing of the handle portion, the trigger arm having a finger portion that is contactable by a person manipulating the device, the trigger arm being operatively linked to the collar to effect axial movement of the first tubular member in the second tubular member and axial movement of the first tubular member on the catheter to cover and uncover the articulating tip of the catheter.

12. A medical fluid delivery device as defined by claim 11, wherein the actuator further includes a torsion spring, the torsion spring being joined to the handle housing and the trigger arm and biasing the trigger arm in a direction to assist the person manipulating the device and to at least help cause the axial movement of the first tubular member in covering and uncovering the articulating tip of the catheter.

13. A medical fluid delivery device as defined by claim 11, wherein the actuator further includes a linkage, the linkage being joined to the collar and to the trigger arm, whereby movement of the trigger arm effects axial movement of the collar which causes the first tubular member to move axially on the catheter to uncover the articulating tip of the catheter.

14. A medical fluid delivery device as defined by claim 1, wherein the actuator includes:

a handle portion, the handle portion having a housing defining a handle for grasping by a person manipulating the device, and further defining a barrel for receiving therein a syringe containing a medical fluid;

a collar, the collar being slidably situated on the second tubular member and being operatively linked to the first tubular member; and a trigger arm, the trigger arm being movably mounted on the housing of the handle portion, the trigger arm having a finger portion that is contactable by a person manipulating the device, the trigger arm being operatively coupled to the first tubular member to effect axial movement of the first tubular member in the second tubular member and axial movement of the first tubular member on the catheter to cover and uncover the articulating tip of the catheter.

15. A medical fluid delivery device as defined by claim 1, wherein the actuator includes:
 a handle portion, the handle portion having a housing defining a handle for grasping by a person manipulating the device, and further defining a barrel for receiving therein a syringe containing a medical fluid;
 wherein the catheter has a distal end and a proximal end situated axially opposite the distal end, the articulating tip of the catheter being situated at the distal end thereof;
 and wherein the actuator further includes a fitting mounted on the proximal end of the catheter for connection to the syringe containing a medical fluid therein, the fitting being rotatable with respect to the handle housing, the catheter being rotatable within the first tubular member, whereby rotation of the fitting causes rotation of the catheter and the articulating tip of the catheter.

16. A medical fluid delivery device as defined by claim 15, wherein the actuator further includes means for locking the fitting to prevent rotation thereof and to prevent rotation of the articulating tip of the catheter.

17. A medical fluid delivery device as defined by claim 16, wherein the fitting includes an outer surface having at least one opening formed radially therein; and wherein the fitting locking means includes a lock pin, the lock pin selectively being received by the at least one opening formed in the fitting to prevent rotation thereof.

18. A medical fluid delivery device as defined by claim 17, wherein the fitting locking means further includes means for biasing the lock pin, the lock pin biasing means engaging the lock pin to bias the lock pin non-receivably by the at least one opening formed in the fitting.

19. A medical fluid delivery device as defined by claim 18, wherein the lock pin biasing means includes a spring, the spring engaging the handle housing and the lock pin.

20. A medical fluid delivery device as defined by claim 1, wherein the actuator includes:
 a handle portion, the handle portion having a housing defining a handle for grasping by a person manipulating the device, and further defining a barrel for receiving therein a syringe containing a medical fluid, the syringe having a barrel and a plunger slidably receivable by the syringe barrel; and
 a plunger linkage for remotely effecting movement of the syringe plunger, the plunger linkage being reciprocatingly slidable on the handle housing, the linkage having a main body, a shoulder extending outwardly from the main body, the shoulder defining a finger rest and being provided for contacting by the finger of a person manipulating the device and for the person exerting a force thereon to move the syringe plunger with respect to the syringe, and a plunger engaging piece extending from the main body and engaging the syringe plunger, whereby finger pressure exerted by the person on the shoulder defining the finger rest causes the plunger to move axially within the syringe barrel.

21. A medical fluid delivery device as defined by claim 20, wherein the shoulder defining the finger rest of the plunger linkage is sloped at an angle which is less than 90° with respect to the axis of the second tubular member.

22. A medical fluid delivery device as defined by claim 20, wherein the handle housing has a first lateral sidewall and an opposite second lateral sidewall; wherein at least one of the first lateral sidewall and the second lateral sidewall has a slot formed therein, the slot extending substantially parallel to the axis of the second tubular member; and wherein the main body of the plunger linkage includes a protrusion extending from a surface thereof, the protrusion being reciprocatingly slidably received by the slot, whereby the plunger linkage is movably mounted on the at least one of the first lateral sidewall and the second lateral sidewall of the handle housing.

23. A medical fluid delivery device as defined by claim 1, wherein the first tubular member includes a distal end and a proximal end situated axially opposite the distal end, the distal end being situated in proximity to the articulating tip of the catheter, the proximal end of the first tubular member having a threaded portion; and wherein the actuator includes:
 a handle portion, the handle portion having a housing defining a handle for grasping by a person manipulating the device, and further defining a barrel for receiving therein a syringe containing a medical fluid, the handle portion further having a nose piece rotatably mounted on the handle housing and having a threaded central bore formed axially therein, the threaded central bore engagably receiving the threaded portion of the first tubular member, the first tubular member being non-rotatably mounted to the handle housing, whereby rotation of the nose piece causes axial movement of the first tubular member on the catheter to cover and uncover the articulating tip of the catheter.

24. A medical fluid delivery device as defined by claim 1, which further comprises:
 a fluid seal, the fluid seal being situated on the catheter and being in communication with the at least one lumen thereof to selectively prevent the flow of medical fluid through the at least one catheter lumen and to allow the flow of medical fluid therethrough upon a predetermined pressure being exerted on the medical fluid.

25. A medical fluid delivery device as defined by claim 1, wherein the first tubular member includes a distal end and a proximal end situated axially opposite the distal end, the distal end being situated in proximity to the articulating tip of the catheter; and wherein the actuator includes:
 a handle portion, the handle portion having a housing defining a handle for grasping by a person manipulating the device, and further defining a barrel for receiving therein a syringe containing a medical fluid, the handle portion further having a nose piece rotatably mounted on the handle housing and having an axial bore formed therein, and a collar received by the axial bore of the nose piece and axially moveable within the nose piece bore, the handle housing including a portion thereof having a threaded outer surface, the collar including a portion thereof having a threaded inner surface, the threaded inner surface of the collar threadingly engaging the threaded outer surface of the handle housing portion, the collar being operatively coupled to the nose piece and rotatable therewith and axially movable thereon within the axial bore of the nose piece, wherein rotation of the nose piece causes rotation of the collar, and engagement of the threaded outer surface of the handle housing portion and the threaded inner surface of the collar causes axial movement of the collar when the nose piece is rotated, the proximal end of the first tubular member being affixed to the collar, whereupon rotation of the nose piece causes axial movement of the first tubular member on the catheter to cover and uncover the articulating tip of the catheter.

26. A medical fluid delivery device as defined by claim 25, wherein the nose piece includes a radially inner surface, the radially inner surface having at least one channel formed therein and extending at least partially axially along the length of the nose piece; and wherein the collar has an outer surface and a rib extending radially outwardly from the outer surface and axially along at least a portion of the longitudinal length thereof, the rib of the collar being slidably received by the channel of the nose piece to operatively couple the nose piece to the collar.

27. A medical fluid delivery device comprising:
- a catheter having a proximal end, a distal end, and at least one lumen extending between the proximal and distal ends thereof, said catheter including an articulating tip adjacent the distal end thereof having a pre-shaped curvature;
- a first rigid tubular member having a first axial bore formed therein, said catheter being at least partially disposed within the first axial bore of said first rigid tubular member;
- a second rigid tubular member having a proximal end, a distal end, a longitudinal axis extending between the proximal and distal ends, and a second axial bore formed therein and extending along the longitudinal axis, said first rigid tubular member being at least partially disposed within the second axial bore of said second rigid tubular member; and
- an actuator coupled with said first rigid tubular member to selectively move said first rigid tubular member relative to said catheter and said second rigid tubular member to selectively vary a degree of curvature of said articulating tip, wherein said curved articulating tip of said catheter is constrained by said first rigid tubular member from articulating to the pre-shaped curvature when said first rigid tubular member covers said articulating tip, and said pre-shaped articulating tip of said catheter is free to bend to a selected degree of curvature when said articulating tip is at least partially uncovered by said first rigid tubular member, wherein said catheter and said second rigid tubular member are fixed from axial movement relative to one another and said first rigid tubular member is adapted for axial movement relative to both said catheter and said second rigid tubular member.

28. The medical fluid delivery device as defined by claim 27, wherein said first and second rigid tubular members are substantially straight.

29. The medical fluid delivery device as defined by claim 27, wherein said catheter comprises a shape memory material.

30. A laparoscopic device comprising:
- a rigid outer tube having a proximal end, a distal end, a longitudinal axis extending between the proximal and distal ends, and a bore extending between the proximal and distal ends and along the longitudinal axis of said rigid outer tube;
- a rigid inner tube having a proximal end, a distal end, and an inner bore extending between the proximal and distal ends of said rigid inner tube, wherein said rigid inner tube is at least partially disposed within said bore of said rigid outer tube and is adapted to slide along the longitudinal axis of said rigid outer tube;
- a catheter having a proximal end, a distal end, and at least one lumen extending between the proximal and distal ends thereof, wherein said catheter is at least partially disposed within the inner bore of said rigid inner tube and includes an articulating tip adjacent the distal end thereof having a pre-shaped curvature; and
- an actuator coupled with said rigid inner tube for selectively moving said rigid inner tube relative to said catheter and said rigid outer tube, wherein said pre-shaped articulating tip of said catheter is constrained by said rigid inner tube from articulating to the pre-shaped curvature when said rigid inner tube covers said articulating tip, and said pre-shaped articulating tip of said catheter is free to bend to a selected degree of curvature when said articulating tip is at least partially uncovered by said rigid inner tube, wherein said catheter and said rigid outer tube are fixed from axial movement relative to one another and said rigid inner tube is adapted for axial movement relative to both said catheter and said rigid outer tube.

31. The laparoscopic device as defined by claim 30, wherein said rigid inner and outer tubes are substantially straight.

* * * * *